United States Patent
Ichikawa et al.

(10) Patent No.: US 8,614,046 B2
(45) Date of Patent: Dec. 24, 2013

(54) SALT AND PHOTORESIST COMPOSITION CONTAINING THE SAME

(75) Inventors: Koji Ichikawa, Toyonaka (JP); Masako Sugihara, Nishinomiya (JP); Yuko Yamashita, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 484 days.

(21) Appl. No.: 12/833,457

(22) Filed: Jul. 9, 2010

(65) Prior Publication Data

US 2011/0014566 A1   Jan. 20, 2011

(30) Foreign Application Priority Data

Jul. 14, 2009   (JP) ................... 2009-165357

(51) Int. Cl.
| | |
|---|---|
| G03F 7/004 | (2006.01) |
| G03F 7/30 | (2006.01) |
| C07C 22/02 | (2006.01) |
| C07C 57/28 | (2006.01) |
| C07C 61/35 | (2006.01) |
| C07C 63/64 | (2006.01) |
| C07C 63/66 | (2006.01) |
| G03F 7/039 | (2006.01) |
| C08F 22/02 | (2006.01) |

(52) U.S. Cl.
CPC ............ *G03F 7/0045* (2013.01); *G03F 7/0397* (2013.01); *G03F 7/30* (2013.01); *C07C 63/64* (2013.01); *C08F 22/02* (2013.01); *C07C 63/66* (2013.01); *C07C 57/28* (2013.01); *Y10S 430/122* (2013.01); *Y10S 430/123* (2013.01)
USPC ........ 430/270.1; 430/326; 430/330; 430/921; 430/922; 526/318; 562/495; 562/510; 562/598

(58) Field of Classification Search
CPC ........... G03F 7/045; G03F 7/039; G03F 7/30; C08F 22/02; C07C 63/64; C07C 63/66; C07C 61/35; C07C 57/28
USPC ...................... 430/270.1, 326, 921, 922, 330; 526/318; 562/510, 495, 598
See application file for complete search history.

(56) References Cited

U.S. PATENT DOCUMENTS

| | | | |
|---|---|---|---|
| 5,945,250 A | 8/1999 | Aoai et al. | |
| 6,136,500 A | 10/2000 | Kobayashi et al. | |
| 6,908,722 B2 | 6/2005 | Ebata et al. | |
| 7,442,485 B2 * | 10/2008 | Oshima et al. | 430/138 |
| 7,932,334 B2 | 4/2011 | Ando et al. | |
| 2002/0051933 A1 | 5/2002 | Kodama et al. | |
| 2003/0224285 A1 | 12/2003 | Nakao et al. | |
| 2004/0018445 A1 | 1/2004 | Akita et al. | |
| 2006/0042949 A1 | 3/2006 | McCollum et al. | |
| 2006/0046190 A1 * | 3/2006 | Sato | 430/270.1 |
| 2006/0194982 A1 | 8/2006 | Harada et al. | |
| 2008/0085468 A1 | 4/2008 | Kamimura et al. | |
| 2011/0014567 A1 | 1/2011 | Ichikawa et al. | |

FOREIGN PATENT DOCUMENTS

| | | |
|---|---|---|
| JP | 11-52575 A | 2/1999 |
| JP | 2000-26446 A | 1/2000 |
| JP | 2002-91002 A | 3/2002 |
| JP | 2008-56668 A | 3/2008 |
| JP | 2008-65114 A | 3/2008 |

OTHER PUBLICATIONS

ITO, "Evolution and Progress of Deep UV Resist Materials", Journal of Photopolymer Science and Technology, vol. 11, No. 3, pp. 379-394, 1998.
Stewart et al., "Acid catalyst mobility in resist resins", J. Vac. Sci. Technol. B, vol. 20, No. 6, pp. 2946-2952, Nov./Dec. 2002.
US Notice of Allowance, dated Jan. 5, 2011, for U.S. Appl. No. 11/642,628.
US Office Action, dated Aug. 24, 2010, for U.S. Appl. No. 11/642,628.
US Office Action, dated Jan. 20, 2010, for U.S. Appl. No. 11/642,628.
US Office Action, dated Jul. 9, 2010, for U.S. Appl. No. 11/642,628.
Wu et al., "Novel Positive-Tone Chemically Amplified Resists with Photoacid Generator in the Polymer Chains", Advanced Materials, vol. 13, No. 9, pp. 670-672, May 3, 2001.
Howelis et al., "Trifluoromethanesulfonic Acid and Derivatives," Chemical Reviews, vol. 77, No. 1, pp. 69-92, 1977.

* cited by examiner

*Primary Examiner* — John Chu
(74) *Attorney, Agent, or Firm* — Birch, Stewart, Kolasch & Birch, LLP

(57) ABSTRACT

A salt represented by the formula (I-Pa):

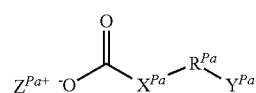

(I-Pa)

wherein $X^{Pa}$ represents a single bond or a C1-C4 alkylene group,
$R^{Pa}$ represents a single bond, a C4-C36 divalent alicyclic hydrocarbon group or a C6-C36 divalent aromatic hydrocarbon group, and one or more methylene groups in the divalent alicyclic hydrocarbon group can be replaced by —O— or —CO—,
$Y^{Pa}$ represents a polymerizable group, and
$Z^{Pa+}$ represents an organic cation.

11 Claims, No Drawings

US 8,614,046 B2

SALT AND PHOTORESIST COMPOSITION CONTAINING THE SAME

This nonprovisional application claims priority under 35 U.S.C. §119(a) on Patent Application No. 2009-165357 filed in JAPAN on Jul. 14, 2009, the entire contents of which are hereby incorporated by reference.

FIELD OF THE INVENTION

The present invention relates to a salt and a photoresist composition containing the same.

BACKGROUND OF THE INVENTION

A chemically amplified positive resist composition used for semiconductor microfabrication employing a lithography process contains an acid generator comprising a compound generating an acid by irradiation.

US 2006/0194982 A1 discloses triphenylsulfonium 1-(3-hydroxyadamantyl)methoxycarbonyldifluoromethanesulfonate and a photoresist composition comprising a resin and triphenylsulfonium 1-(3-hydroxyadamantyl)methoxycarbonyldifluoromethane as an acid generator.

US 2004/0018445 A1 disclose a combination of triphenylsulfonium triisopropylbenzenesulfonate and N-(ethylsulfonyloxy) succinimide, and a photoresist composition comprising a resin and a combination of triphenylsulfonium triisopropylbenzenesulfonate and N-(ethylsulfonyloxy)succinimide as an acid generator.

SUMMARY OF THE INVENTION

An object of the present invention is to provide a novel salt, a novel polymer derived from the salt and a photoresist composition containing the same.

The present invention relates to the followings:

<1> A salt represented by the formula (I-Pa):

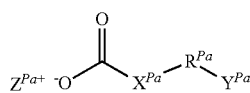

wherein $X^{pa}$ represents a single bond or a C1-C4 alkylene group, $R^{pa}$ represents a single bond, a C4-C36 divalent alicyclic hydrocarbon group or a C6-C36 divalent aromatic hydrocarbon group, and one or more methylene groups in the divalent alicyclic hydrocarbon group can be replaced by —O— or —CO—, $Y^{pa}$ represents a polymerizable group, and $Z^{pa+}$ represents an organic cation;

<2> The salt according to <1>, wherein the polymerizable group is a vinyl group, an acryloyl group, a methacryloyl group, an acryloyloxy group or a methacryloyloxy group, and the vinyl, acryloyl, methacryloyl, acryloyloxy and methacryloyloxy groups can have one or more substituents;

<3> The salt according to <1> or <2>, wherein $Z^{pa+}$ is a cation represented by the formula (IXa):

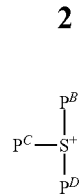

wherein $P^B$, $P^C$ and $P^D$ independently each represent a C1-C10 aliphatic hydrocarbon group which can have one or more substituents, a C4-C36 alicyclic hydrocarbon group which can have one or more substituents, a C6-C36 aromatic hydrocarbon group which can have one or more substituents or a C3-C36 heterocyclic group which can have one or more substituents, and any two of $P^B$, $P^C$ and $P^D$ can be bonded each other to form a ring, and one or more methylene groups in the aliphatic hydrocarbon group and the alicyclic hydrocarbon group can be replaced by —CO— or —O—;

<4> The salt according to <1>, <2> or <3>, wherein $R^{pa}$ is a single bond or an adamantanediyl group;

<5> A polymer comprising a structural unit derived from the salt according to any one of <1> to <4>;

<6> A photoresist composition comprising the polymer according to <5> and an acid generator, <7> A photoresist composition comprising the salt according to any one of <1> to <4>, an acid generator and a resin comprising a structural unit having an acid-labile group and being insoluble or poorly soluble in an aqueous alkali solution but becoming soluble in an aqueous alkali solution by the action of an acid;

<8> The photoresist composition according to <6> or <7>, wherein the photoresist composition further contains a basic compound;

<9> A process for producing a photoresist pattern comprising the following steps (1) to (5):
 (1) a step of applying the photoresist composition according to <6>, <7> or <8> on a substrate,
 (2) a step of forming a photoresist film by conducting drying,
 (3) a step of exposing the photoresist film to radiation,
 (4) a step of baking the exposed photoresist film, and
 (5) a step of developing the baked photoresist film with an alkaline developer, thereby forming a photoresist pattern.

DESCRIPTION OF PREFERRED EMBODIMENTS

The salt of the present invention is represented by the formula (I-Pa):

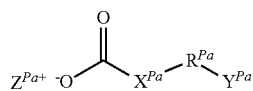

wherein $X^{pa}$ represents a single bond or a C1-C4 alkylene group, $R^{pa}$ represents a single bond, a C4-C36 divalent alicyclic hydrocarbon group or a C6-C36 divalent aromatic hydrocarbon group, and one or more methylene groups in the divalent alicyclic hydrocarbon group can be replaced by —O— or —CO—, $Y^{pa}$ represents a polymerizable group, and $Z^{pa+}$ represents an organic cation.

First, an anion part of the salt represented by the formula (I-Pa) will be illustrated.

Examples of the C1-C4 alkylene group include a methylene group, an ethylene group, a trimethylene group, a tetramethylene group, an isopropylene group, a sec-butylene group and tert-butylene group.

Examples of the C4-C36 divalent alicyclic hydrocarbon group include a cycloalkylene group such as a cyclobutylene group, a cyclopentylene group, a cyclohexylene group, a cycloheptylene group, a cyclooctylene group, a cyclononylene group, a cyclodecylene group, a norbornylene group, an adamantanediyl group and an isobornylene group. One or more methylene groups in the divalent alicyclic hydrocarbon group can be replaced by —O— or —CO—.

Examples of the C6-C36 divalent aromatic hydrocarbon group include a phenylene group, a naphthylene group and an anthrylene group.

$X^{pa}$ is preferably a single bond.

$R^{pa}$ is preferably a single bond, a cyclohexylene group or an adamantanediyl group, and is more preferably a single bond or an adamantanediyl group.

Examples of the polymerizable group include a vinyl group, an acryloyl group, a methacryloyl group, an acryloyloxy group and a methacryloyloxy group. Among them, a vinyl group, an acryloyloxy group and a methacryloyloxy group are preferable. The vinyl, acryloyl, a methacryloyl, acryloyloxy and methacryloyloxy groups can have one or more substituents.

Examples of the anion part of the salt represented by the formula (I-Pa) include the followings.

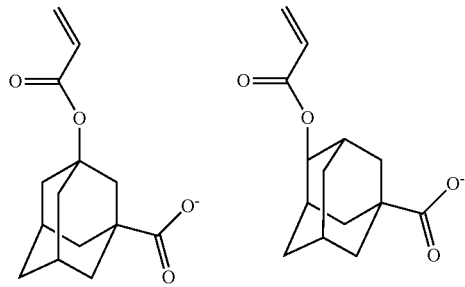
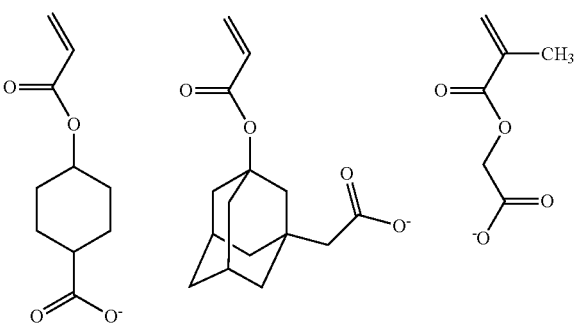
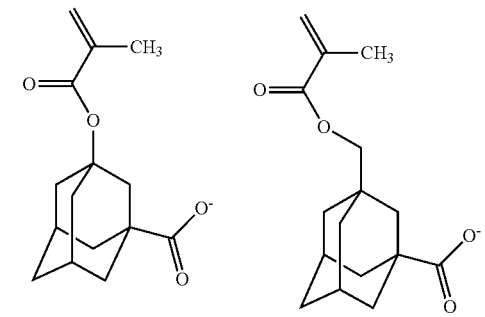
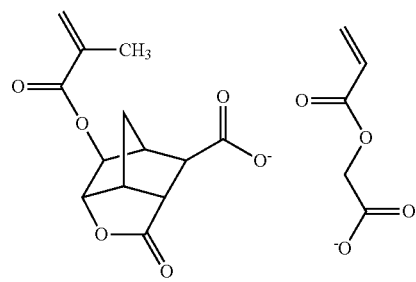
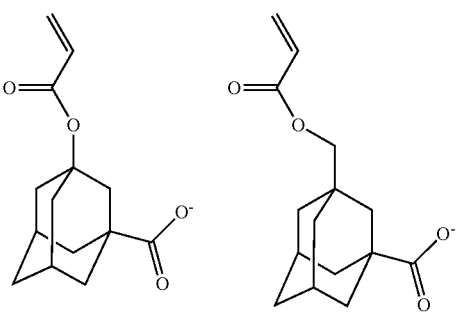

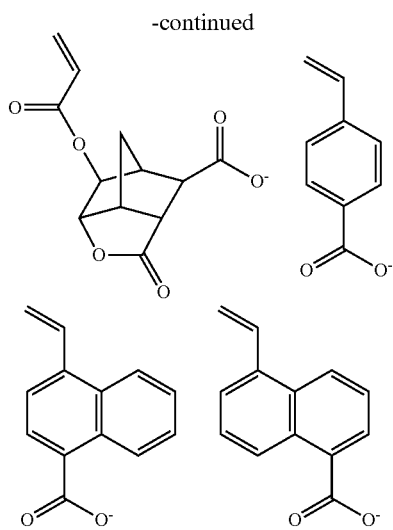

The salt represented by the formula (I-Pa) is preferably a sulfonium salt, an iodonium salt or a carboxyimide compound, and is more preferably a sulfonium salt.

Next, a cation part of the salt represented by the formula (I-Pa) will be illustrated.

Examples of the cation part represented by $Z^{Pa+}$ of the salt represented by the formula (I-Pa) include cations represented by the formulae (IXa), (IXb), (IXc) and (IXd), and a cation represented by the formula (IXa) is preferable.

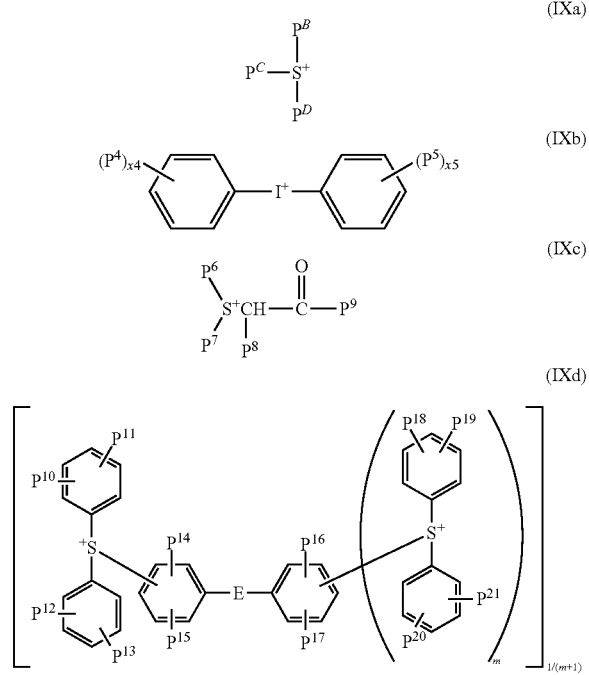

wherein $P^B$, $P^C$ and $P^D$ each independently represent a C1-C10 aliphatic hydrocarbon group which can have one or more substituents, a C4-C36 alicyclic hydrocarbon group which can have one or more substituents, a C6-C36 aromatic hydrocarbon group which can have one or more substituents or a C3-C36 heterocyclic group which can have one or more substituents, and $P^B$ and $P^C$ can be bonded each other to form a ring, and one or more methylene groups in the aliphatic hydrocarbon group and the alicyclic hydrocarbon group can be replaced by —S—, —CO— or —O—, $P^4$ and $P^5$ are independently in each occurrence a hydrogen atom, a hydroxyl group, a C1-C12 alkyl group or a C1-C12 alkoxy group, x4 and x5 independently represents an integer of 1 to 5, and $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and one or more —CH$_2$— in the divalent acyclic hydrocarbon group may be replaced by —CO—, —O— or —S—, and $P^8$ represents a hydrogen atom, $P^9$ represents a C1-C12 alkyl group, a C3-C12 cycloalkyl group or a C6-C20 aromatic group which may be substituted, or $P^8$ and $P^9$ are bonded each other to form a divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, E represents a sulfur atom or an oxygen atom and m represents 0 or 1.

Examples of the aliphatic hydrocarbon group include an alkyl group such as a methyl group, an ethyl group, a propyl group, an isopropyl group, a butyl group, a sec-butyl group, a tert-butyl group, a pentyl group, a hexyl group, a heptyl group, an octyl group, a 2-ethylhexyl group, a nonyl group and a decyl group.

Examples of the alicyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group and an isobornyl group.

Examples of the aromatic hydrocarbon group include a phenyl group, a naphthyl group and an anthryl group.

Examples of the heterocyclic group include the following groups:

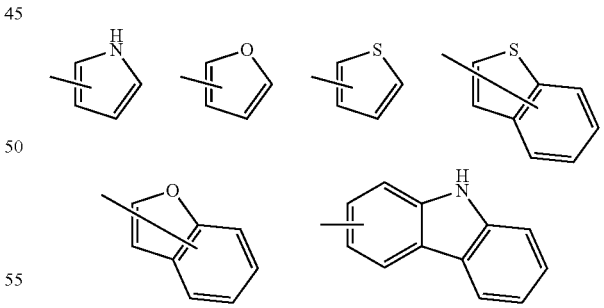

Examples of the ring formed by bonding any two of $P^B$ and $P^C$ each other include an aliphatic ring containing at least one sulfur atom such as a tetrahydrothiophenium ring and an aromatic ring containing at least one sulfur atom.

Examples of the substitute of the aliphatic hydrocarbon group, the alicyclic hydrocarbon group, the aromatic hydrocarbon group and the heterocyclic group include a halogen atom, a hydroxyl group, a C1-C12 alkyl group, a C1-C12 alkoxy group, a C6-C12 aryl group, a C7-C12 aralkyl group, a glycidyloxy group, and a C2-C4 acyl group, and a halogen atom such as a fluorine atom, a hydroxyl group, a C1-C12 alkyl group and a C1-C12 alkoxy group are preferable.

Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the C6-C20 aromatic group include a phenyl group, a tolyl group, a xylyl group, a tert-butylphenyl group and a naphthyl group. Examples of the divalent acyclic hydrocarbon group formed by bonding $P^8$ and $P^9$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (IXaa) is preferable.

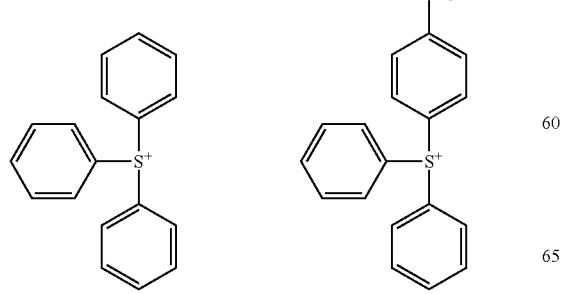

(IXaa)

wherein $P^1$, $P^2$ and $P^3$ each independently represent a hydrogen atom, a hydroxyl group, a C1-C12 alkyl group or a C1-C12 alkoxy group, and $P^1$ and $P^2$, or $P^2$ and $P^3$, or $P^1$ and $P^3$ can be bonded each other to form a ring, and x1, x2 and x3 independently represent an integer 1 to 5.

The ring formed by bonding $P^1$ and $P^2$, or $P^2$ and $P^3$, or $P^1$ and $P^3$ each other may be an aliphatic ring or an aromatic ring.

Examples of the cation represented by the formula (IXaa) include the followings.

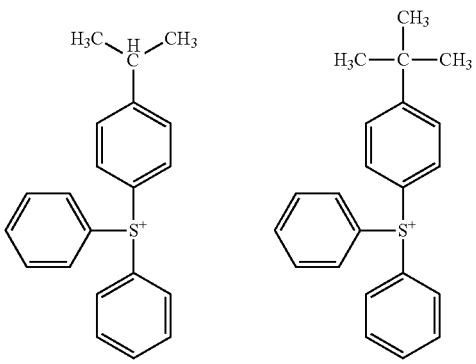

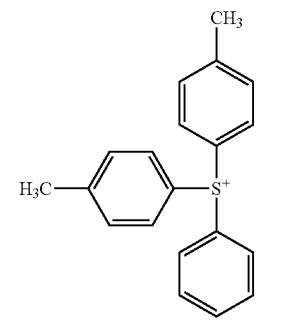

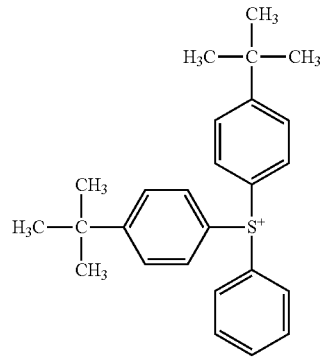

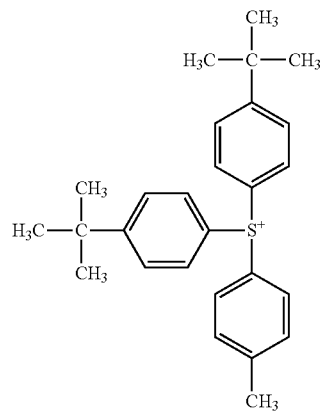

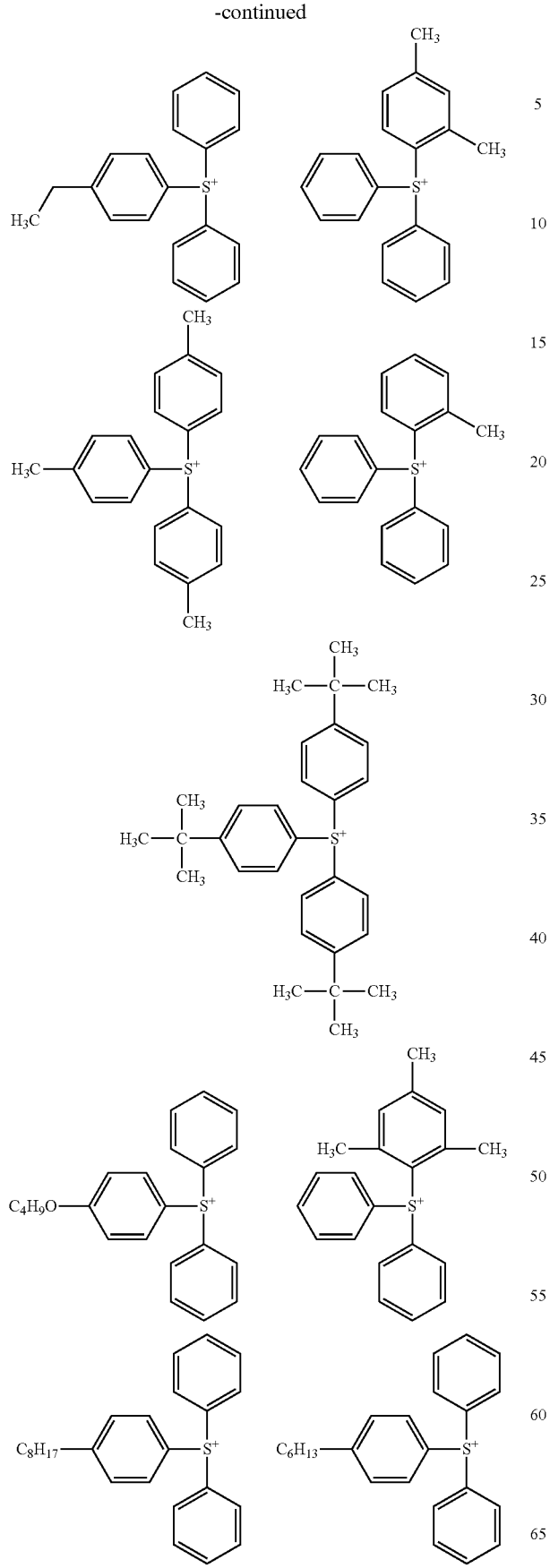

Among the cations represented by the formula (IXaa), the cation represented by the formula (IXaaa) is preferable because of its easy production.

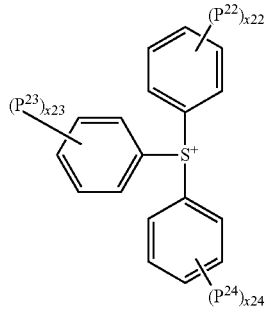

(IXaaa)

wherein $P^{22}$, $P^{23}$ and $P^{24}$ independently each represent a hydrogen atom, a hydroxyl group, a C1-C12 alkyl group or a C1-C12 alkoxy group, and $P^{22}$ and $P^{23}$, or $P^{23}$ and $P^{24}$, or $P^{22}$ and $P^{24}$ can be bonded each other to form a ring, and x22, x23 and x24 independently each represent an integer of 0 to 5.

The ring may be aliphatic ring or an aromatic ring.

Examples of the cation represented by the formula (IXb) include the following.

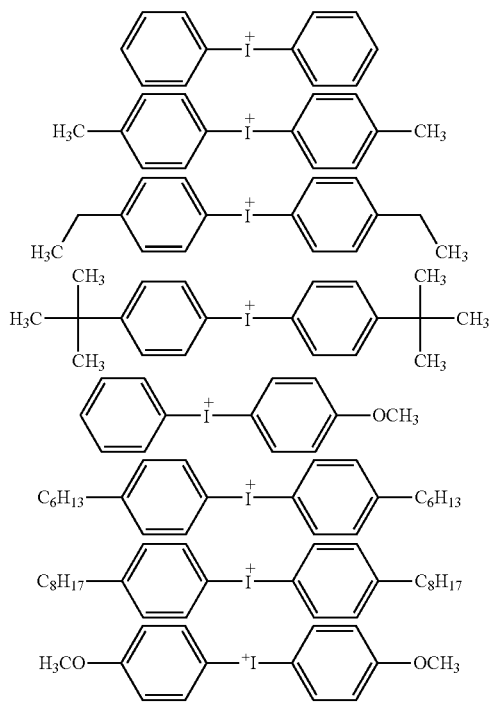

Examples of the cation represented by the formula (IXc) include the following.

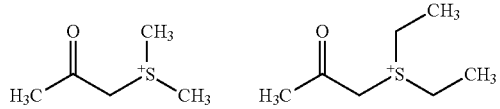

-continued

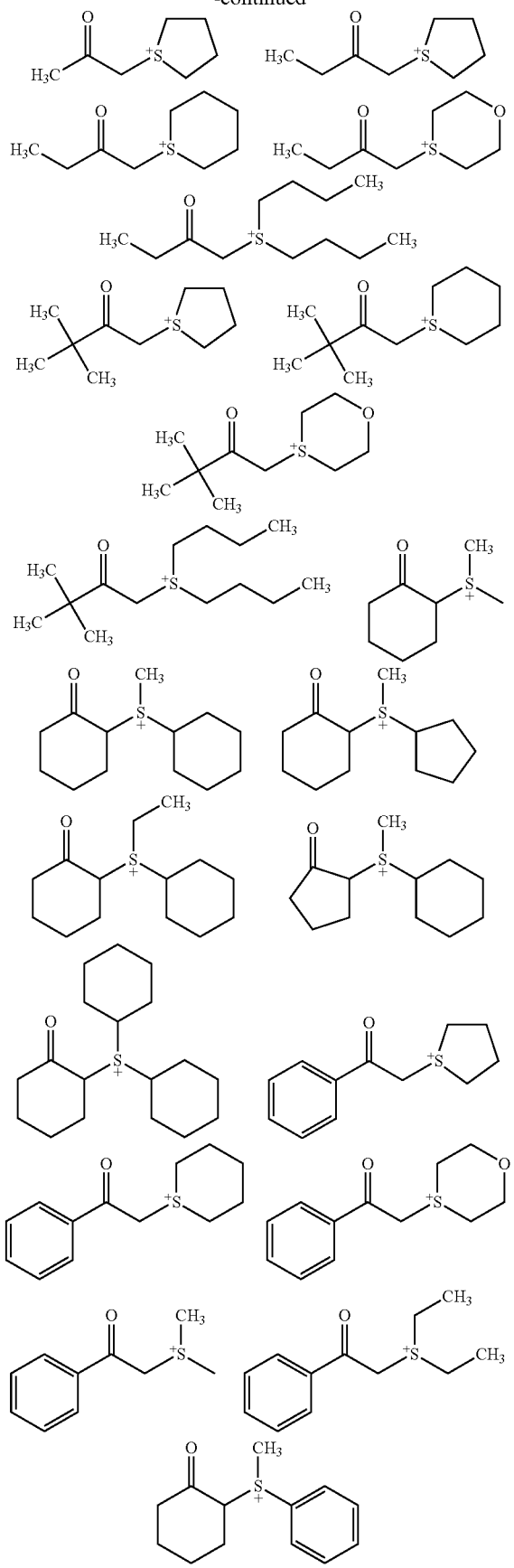

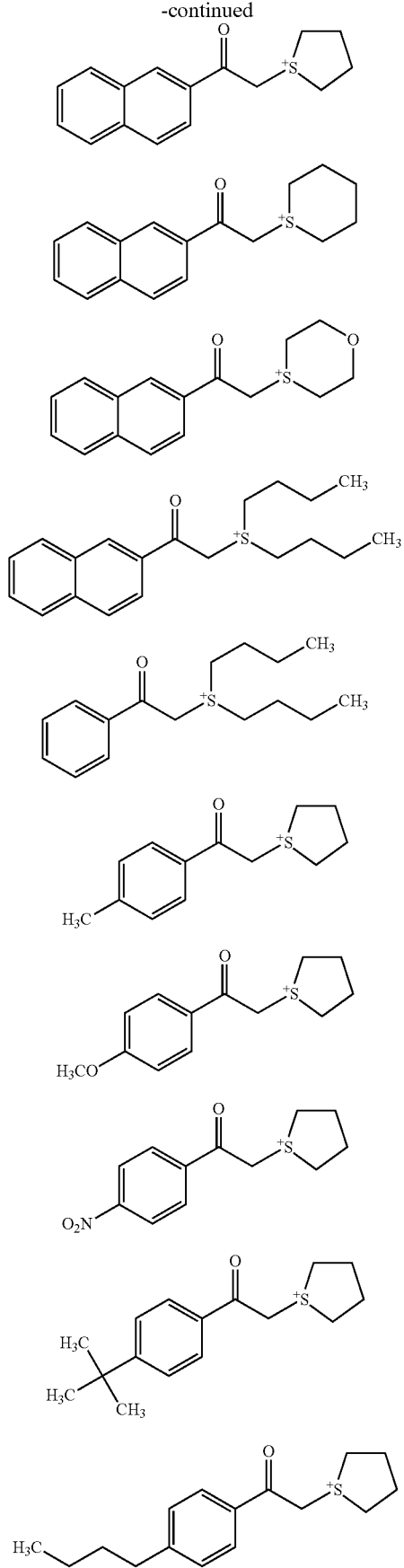
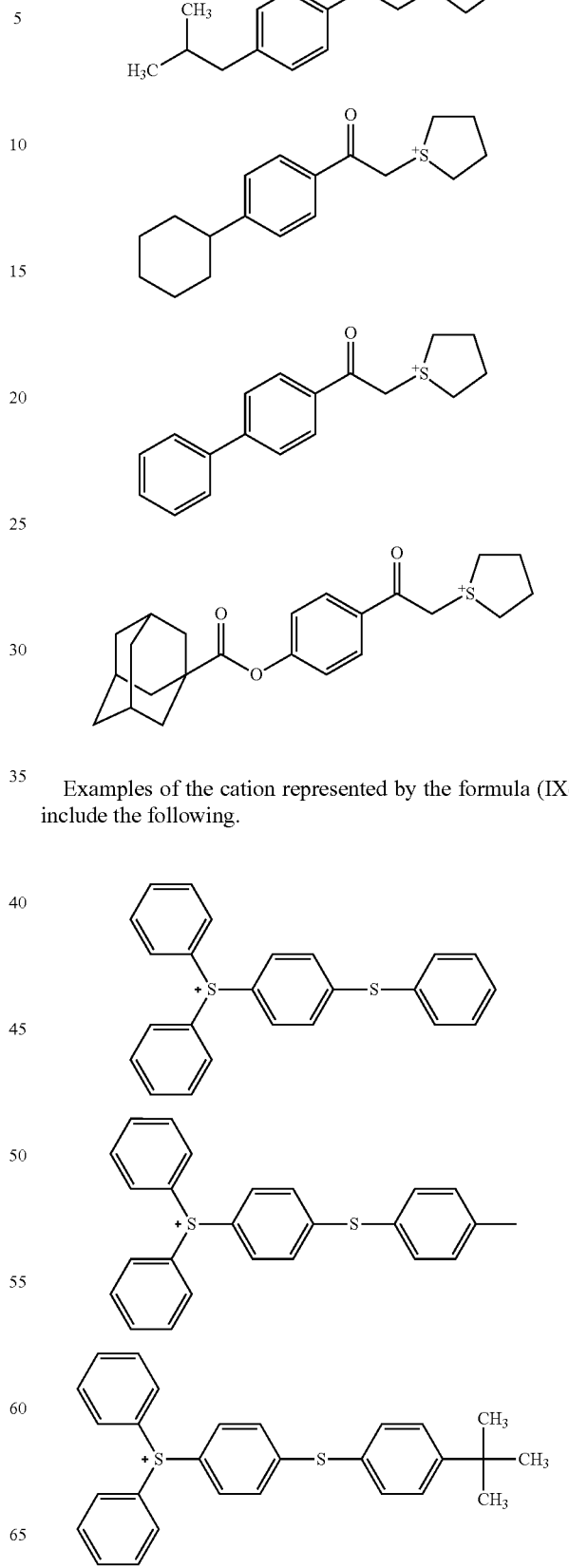
Examples of the cation represented by the formula (IXd) include the following.
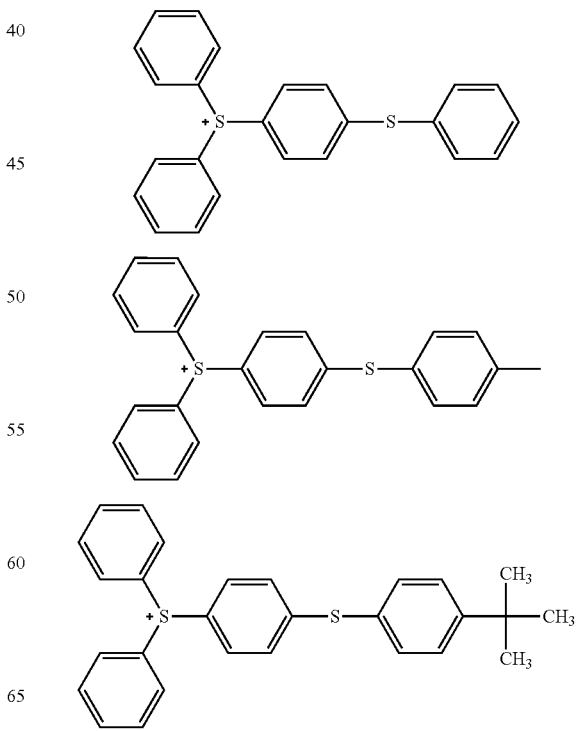

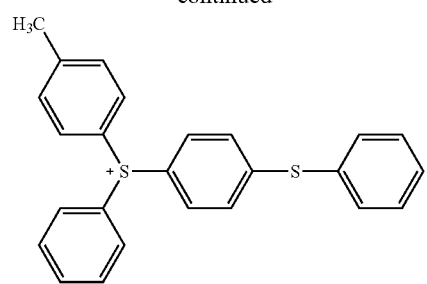
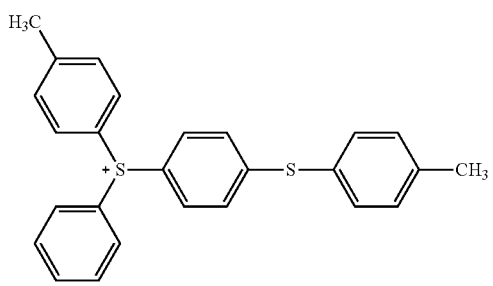
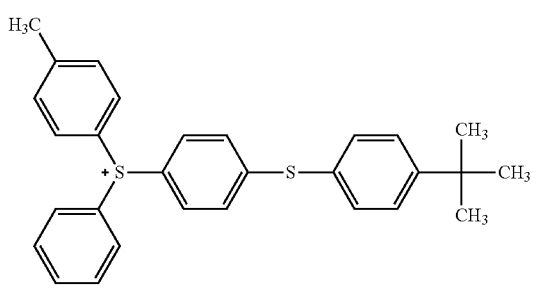
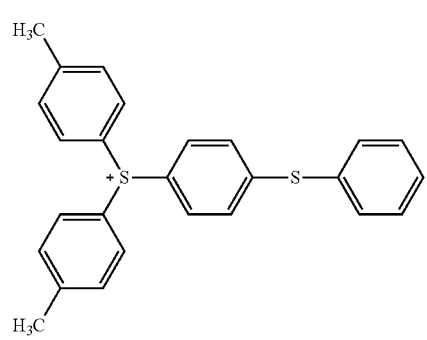
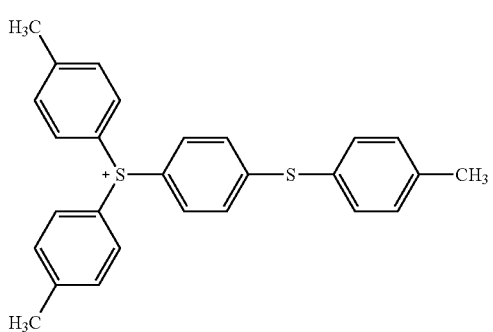
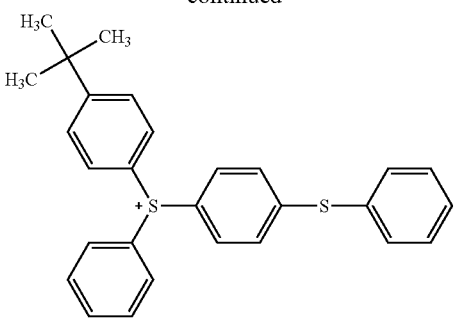
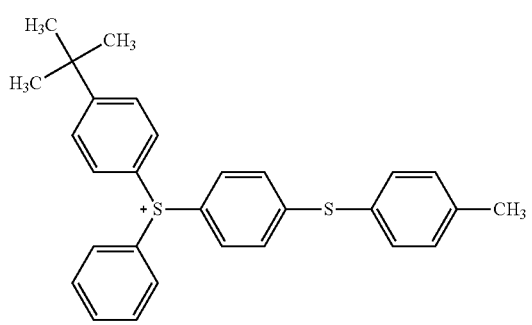
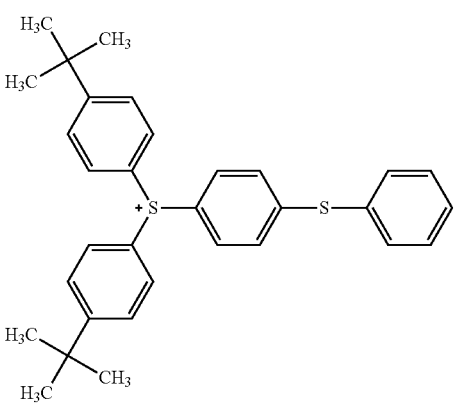
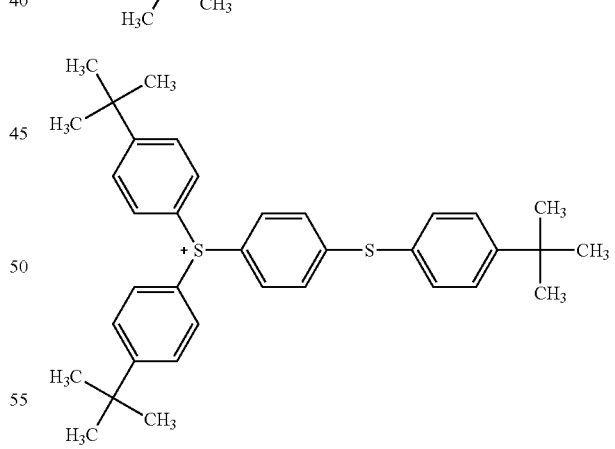
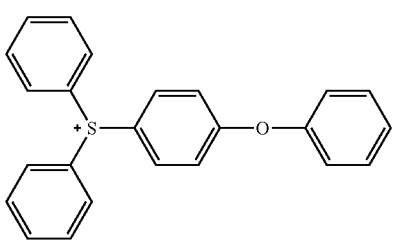

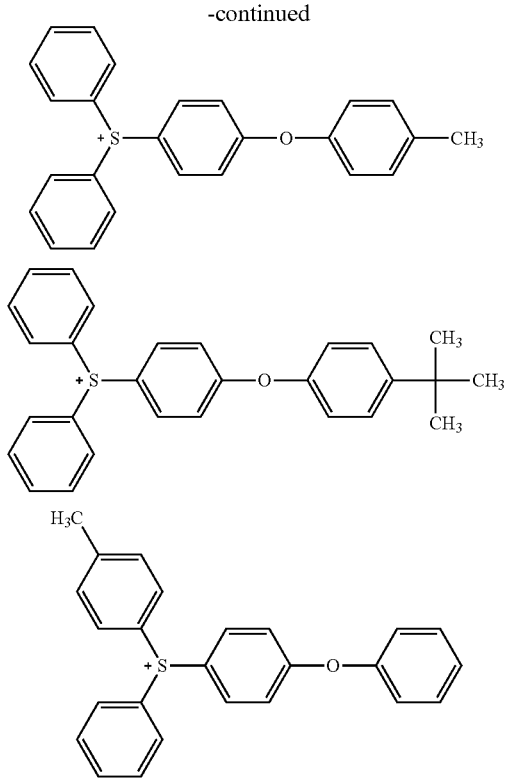
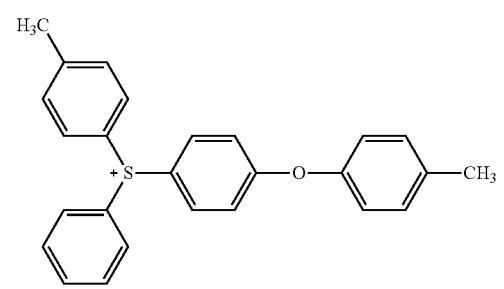
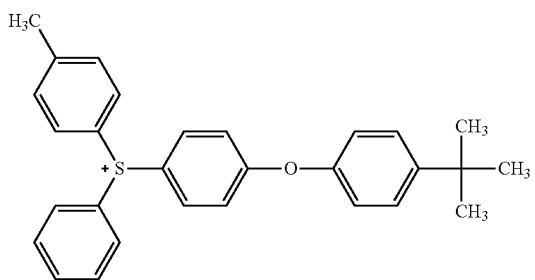
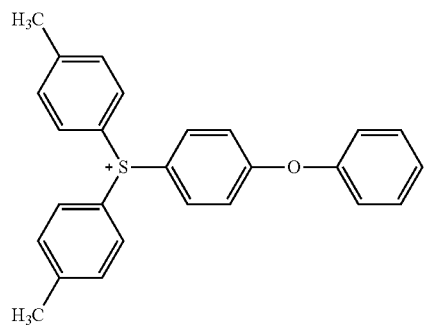
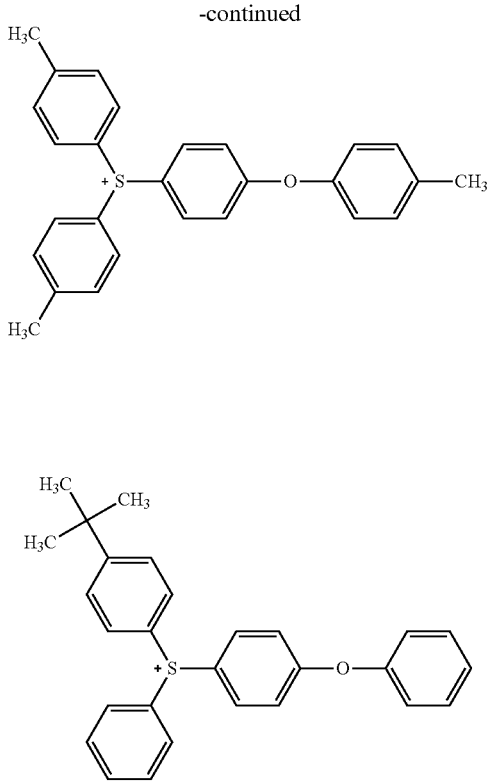
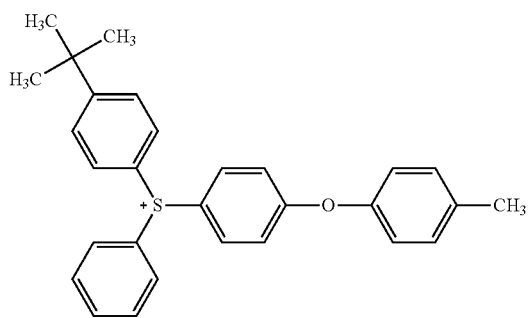
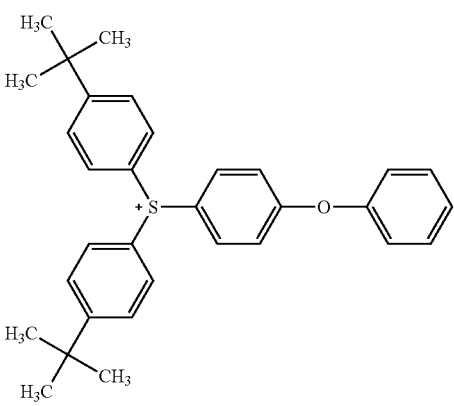

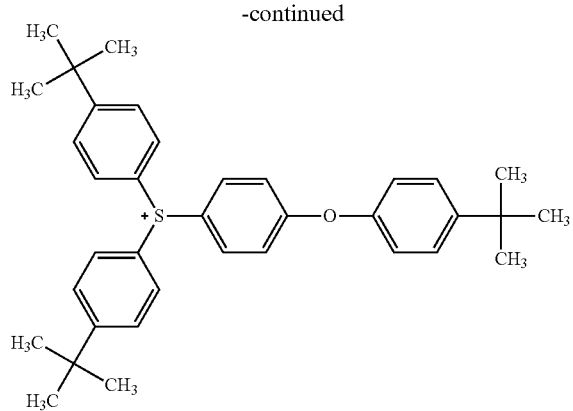
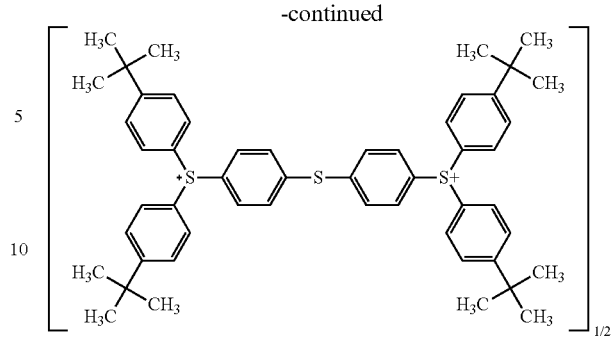
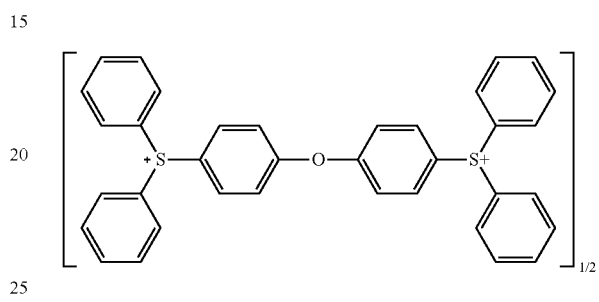
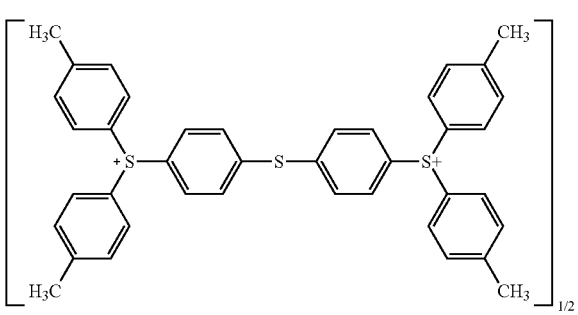
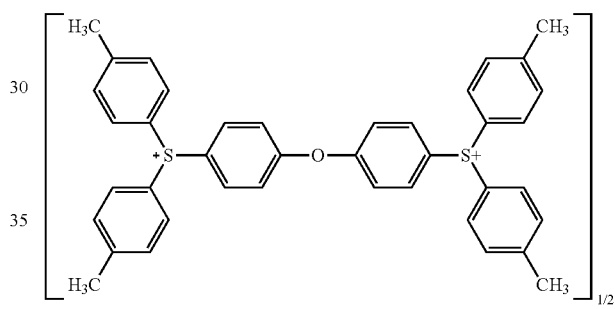
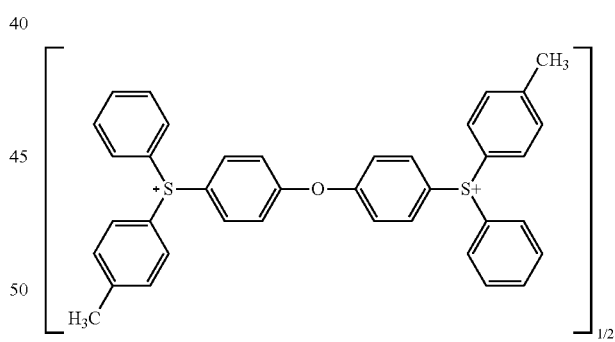
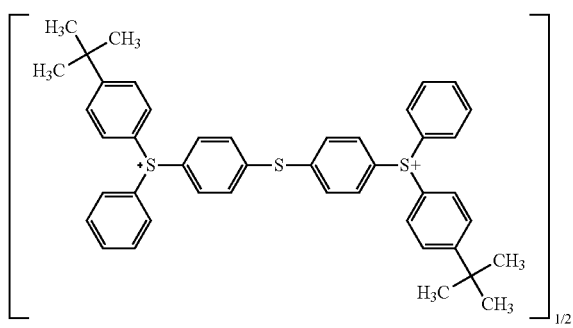
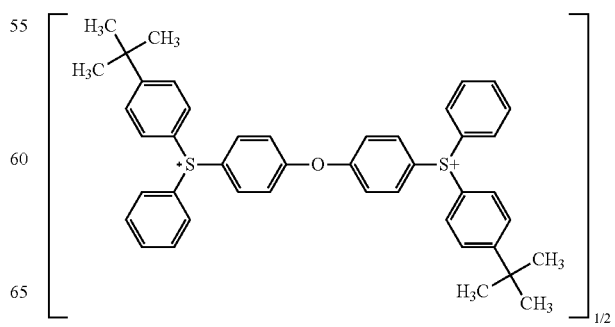

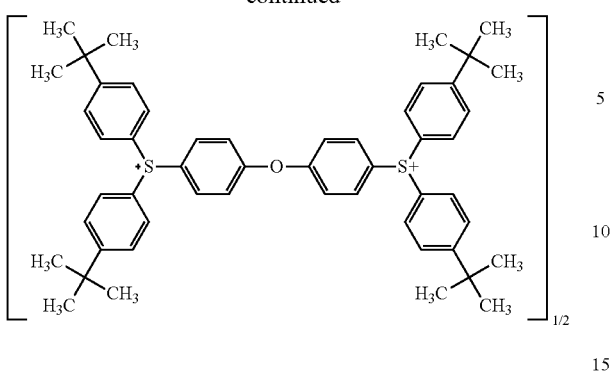
Among them, a triarylsulfonium cation is preferable.
The cations represented by the formulae (IIB-1) to (IIB-96) are more preferable.
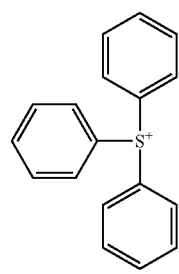
(IIB-1)
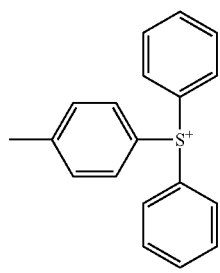
(IIB-2)
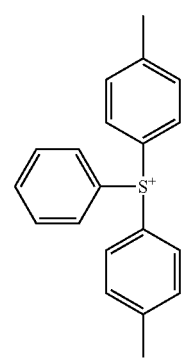
(IIB-3)
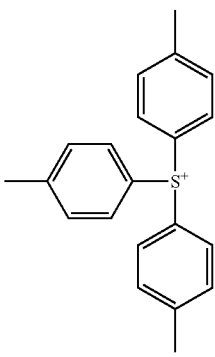
(IIB-4)
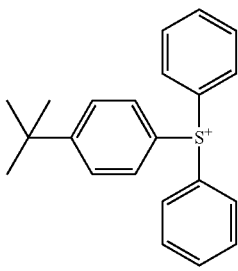
(IIB-5)
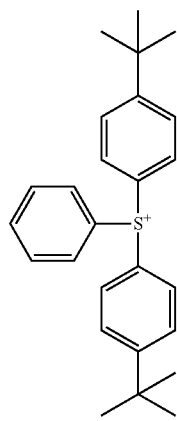
(IIB-6)
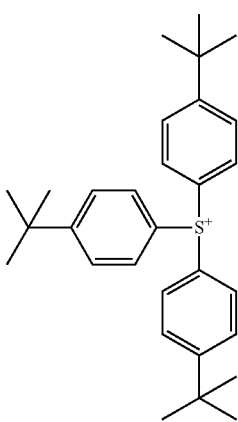
(IIB-7)

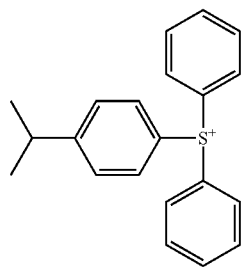 (IIB-8)
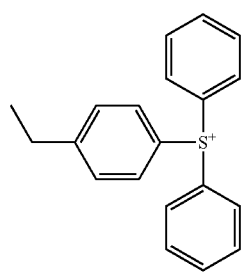 (IIB-9)
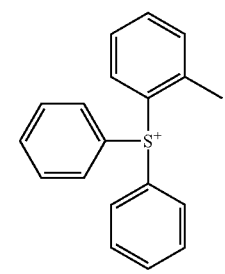 (IIB-10)
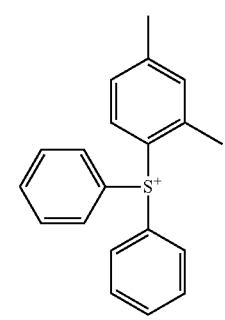 (IIB-11)
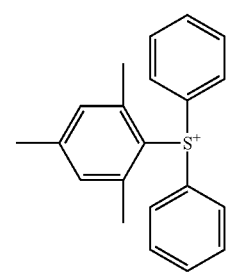 (IIB-12)
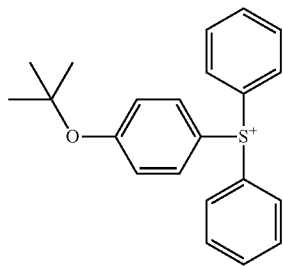 (IIB-13)
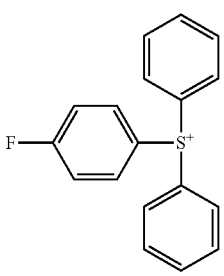 (IIB-14)
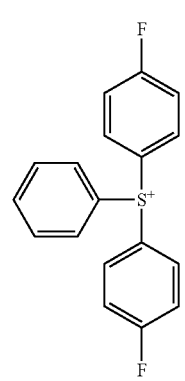 (IIB-15)
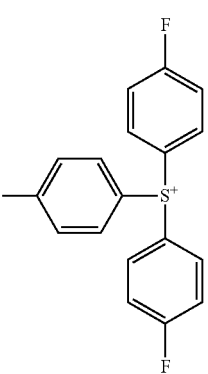 (IIB-16)
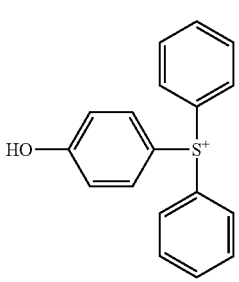 (IIB-17)

(IIB-18) 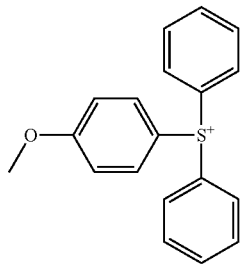
(IIB-19) 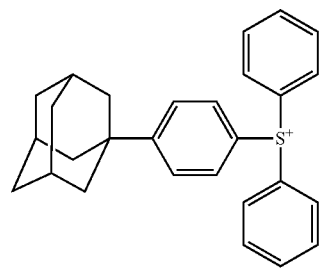
(IIB-20) 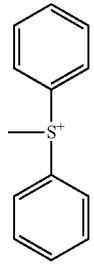
(IIB-21) 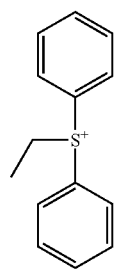
(IIB-22) 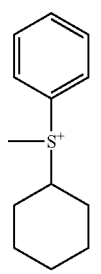
(IIB-23) 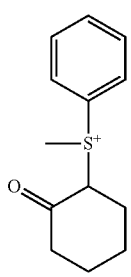
(IIB-24) 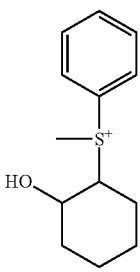
(IIB-25) 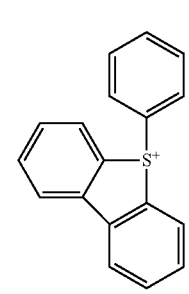
(IIB-26) 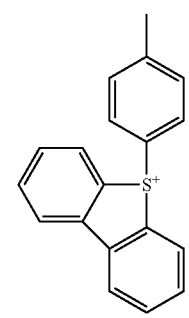
(IIB-27) 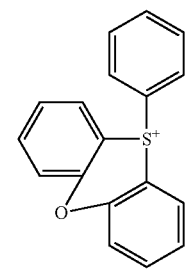
(IIB-28) 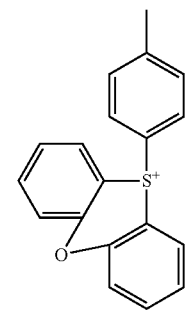

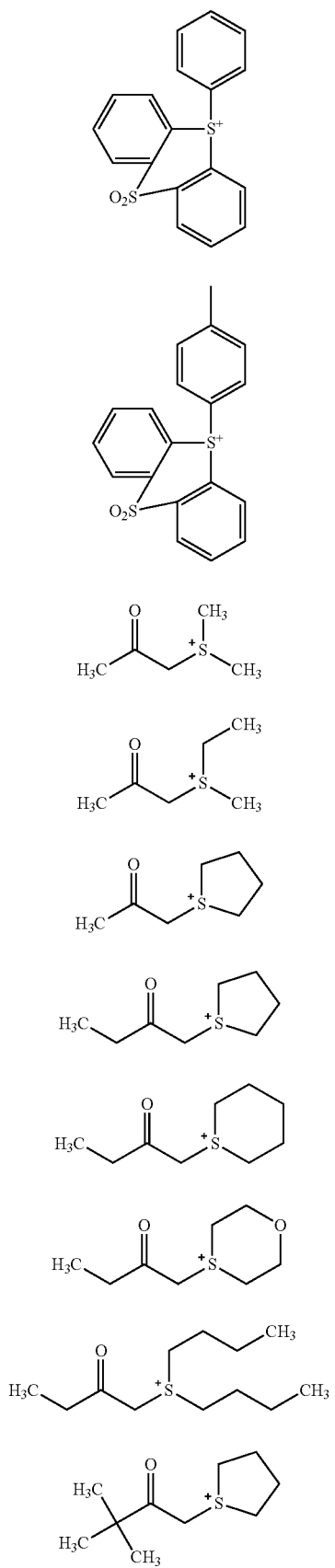

-continued
(IIB-48)
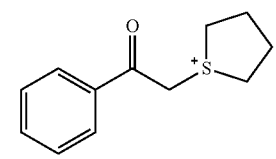
(IIB-49)
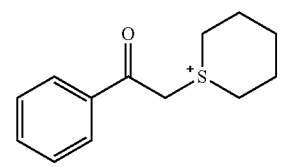
(IIB-50)
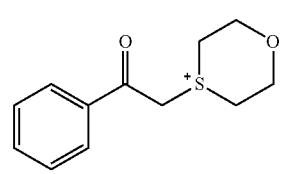
(IIB-51)
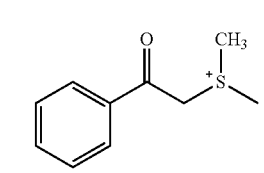
(IIB-52)
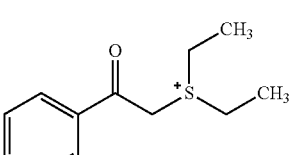
(IIB-53)
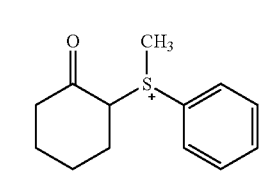
(IIB-54)
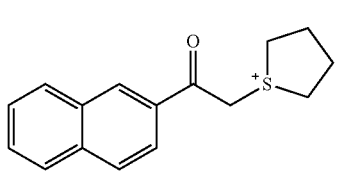
(IIB-55)
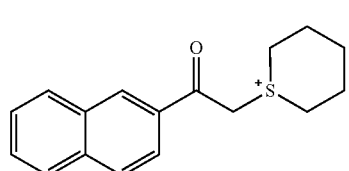
(IIB-56)
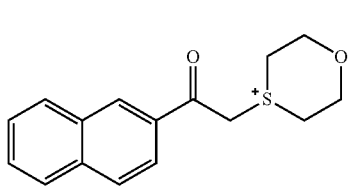
-continued
(IIB-57)
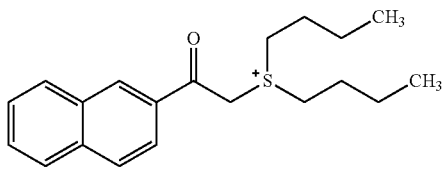
(IIB-58)
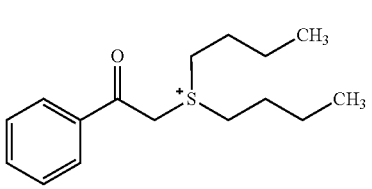
(IIB-59)
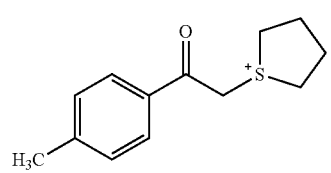
(IIB-60)
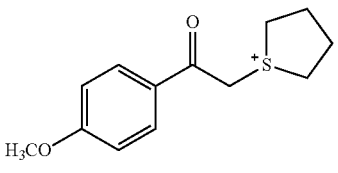
(IIB-61)
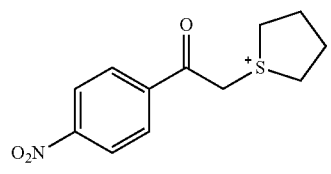
(IIB-62)
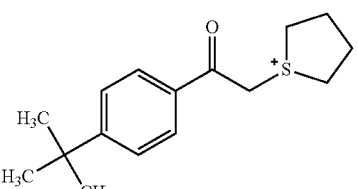
(IIB-63)
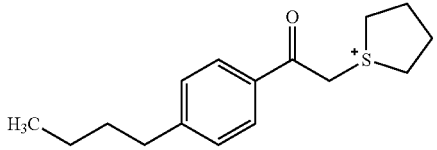
(IIB-64)
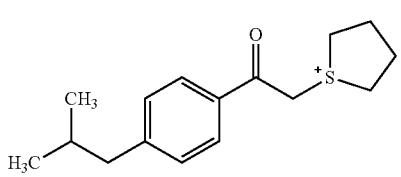

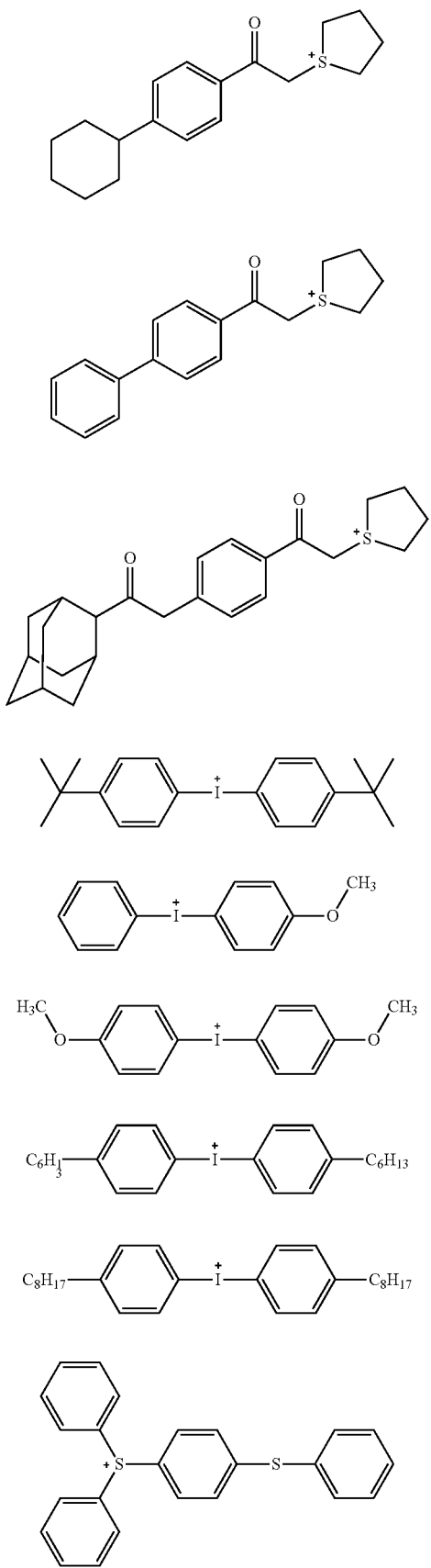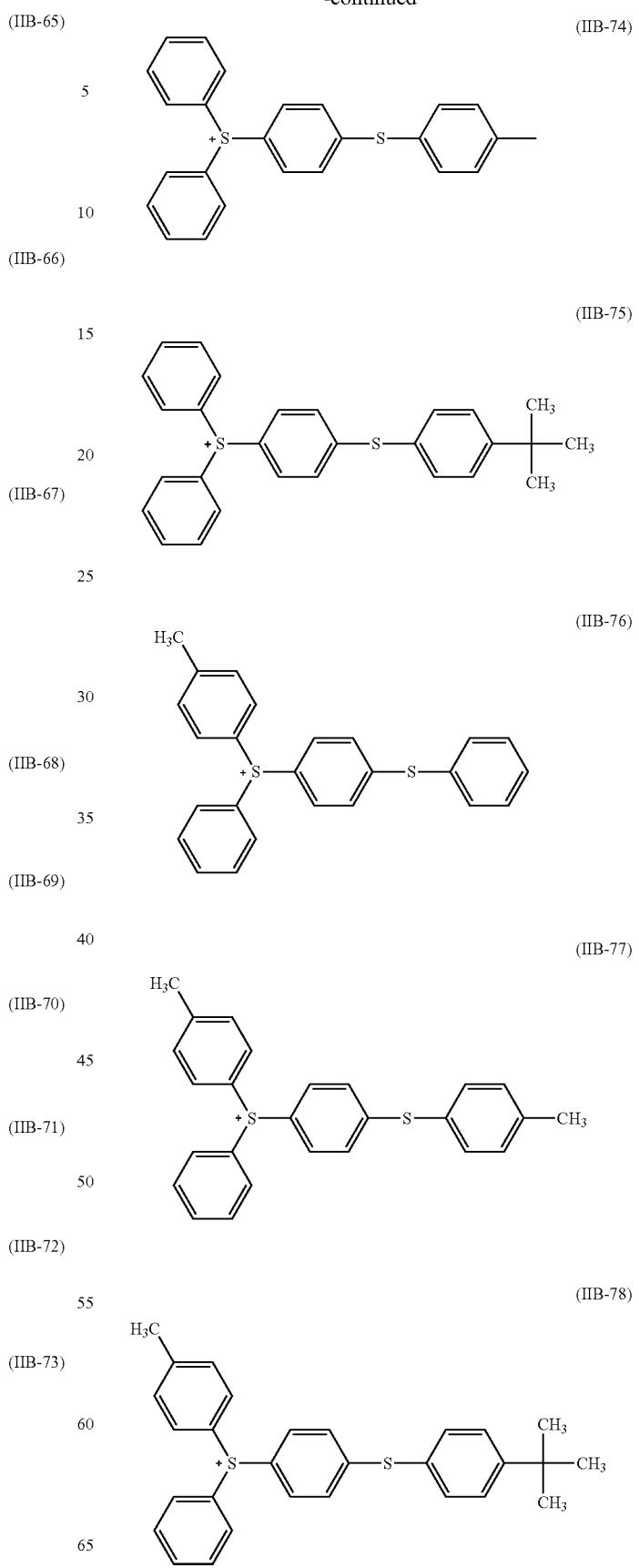

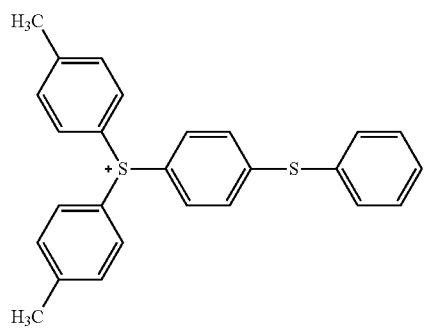
(IIB-79)
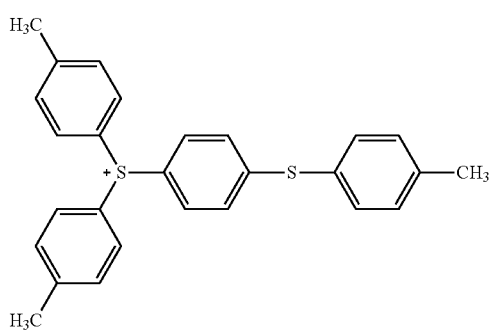
(IIB-80)
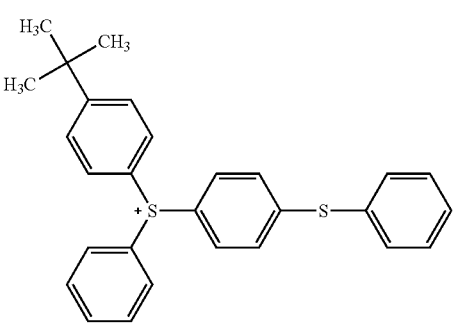
(IIB-81)
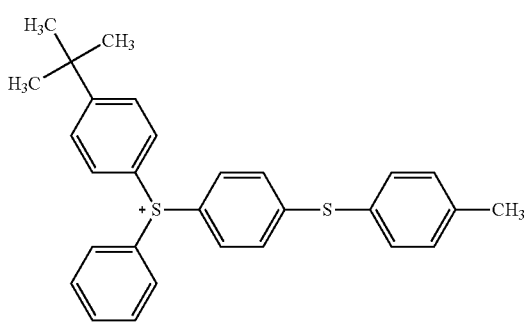
(IIB-82)
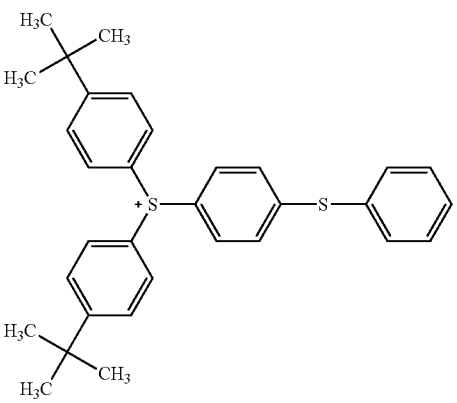
(IIB-83)
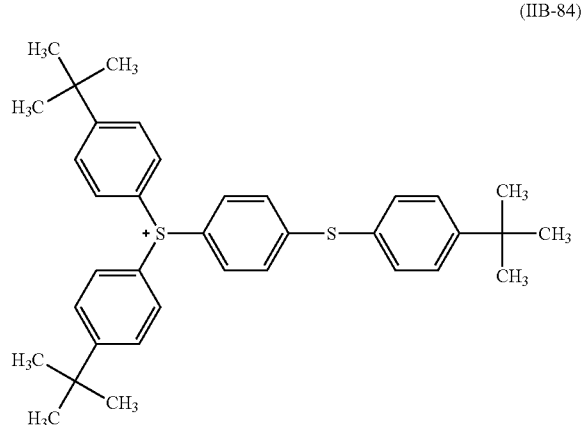
(IIB-84)
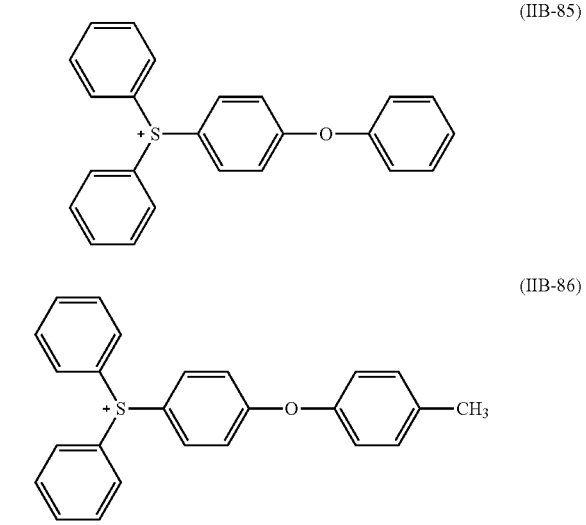
(IIB-85)
(IIB-86)
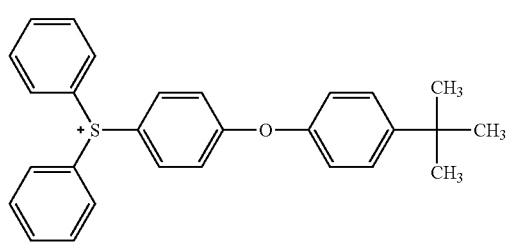
(IIB-87)

(IIB-88)
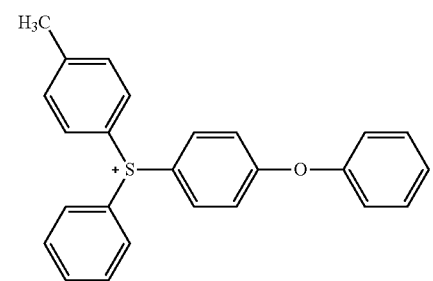
(IIB-89)
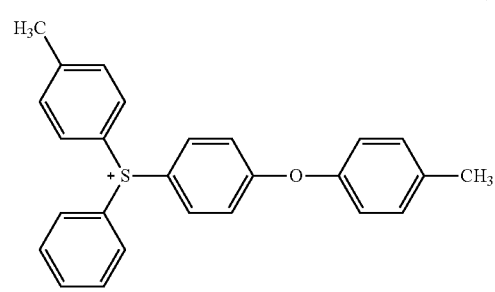
(IIB-90)
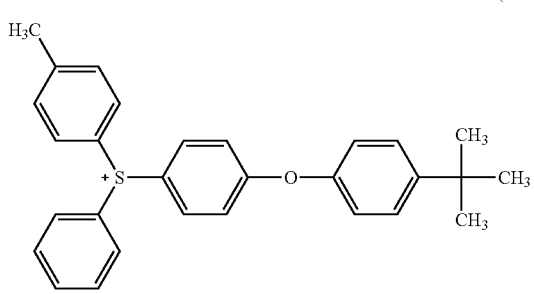
(IIB-91)
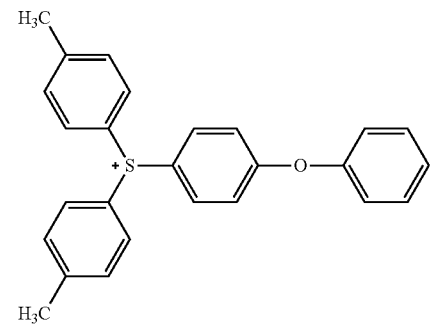
(IIB-92)
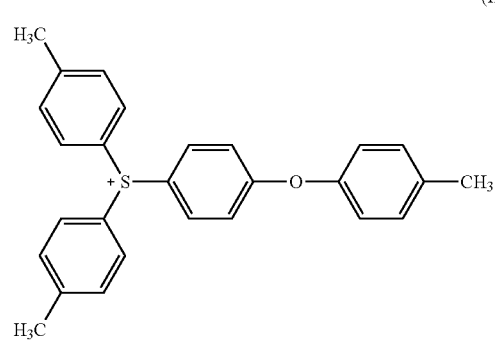
(IIB-93)
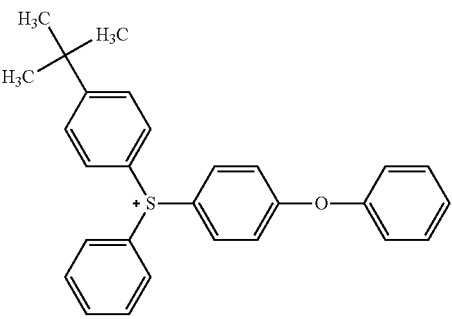
(IIB-94)
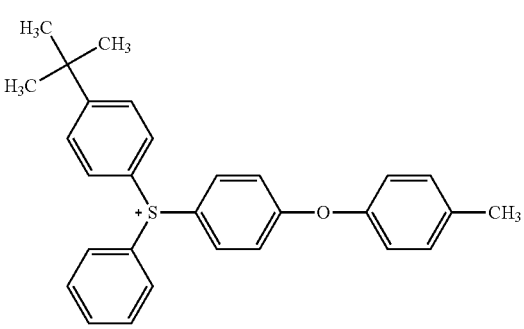
(IIB-95)
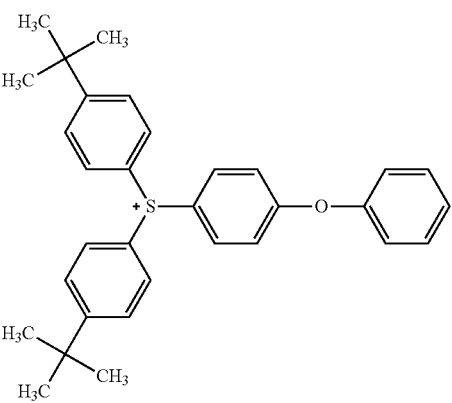
(IIB-96)
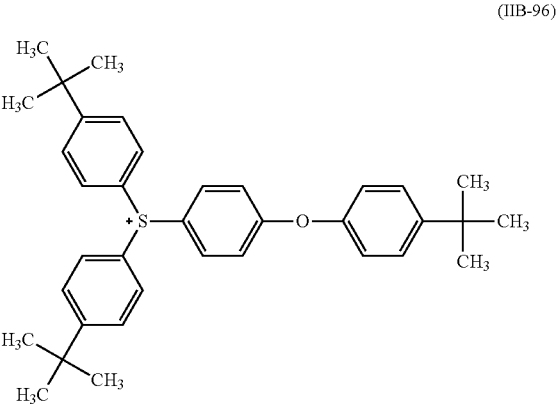
Examples of the salt represented by the formula (I-Pa) include the salts represented by the formulae (I-Pa1') to (I-Pa5').

(I-Pa1′)
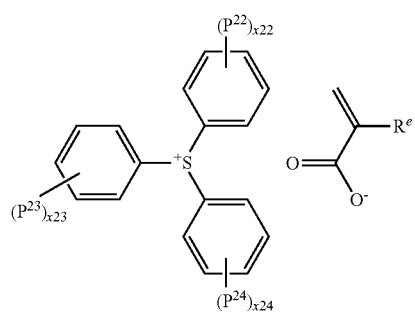
(I-Pa2′)
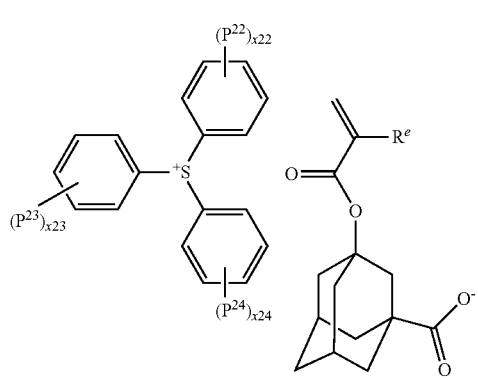
(I-Pa3′)
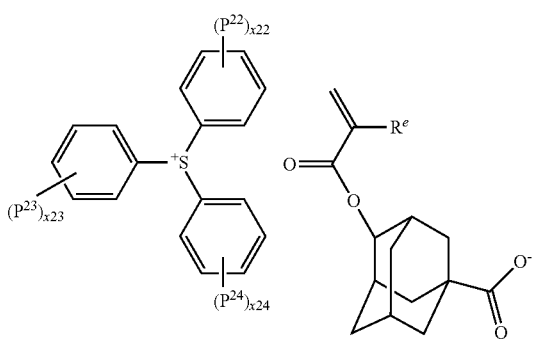
(I-Pa4′)
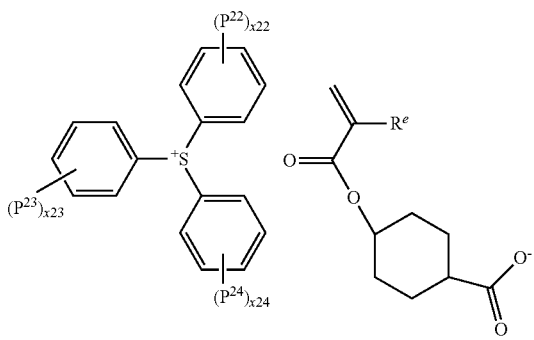
(I-Pa5′)
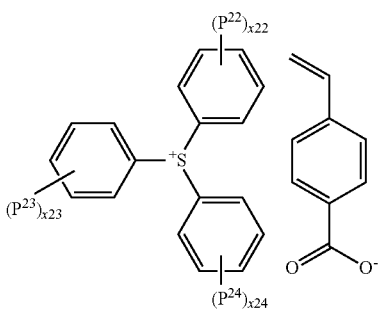
wherein $R^e$ represents a hydrogen atom or a methyl group, and $P^{22}$, $P^{23}$, $P^{24}$, x22, x23 and x24 are the same as defined above.
Examples of the salt represented by the formula (I-Pa) include the followings.
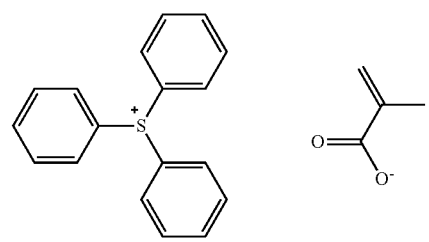
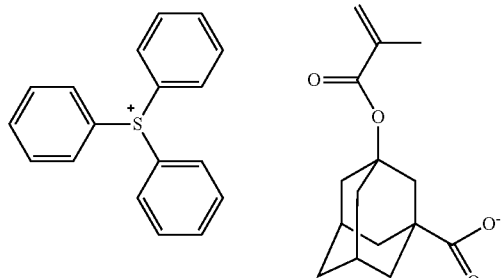
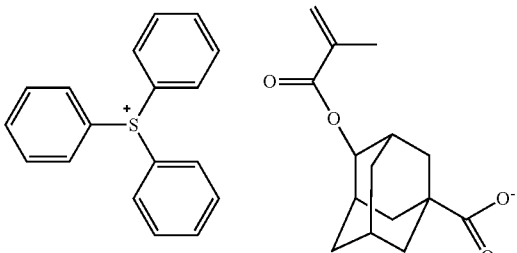
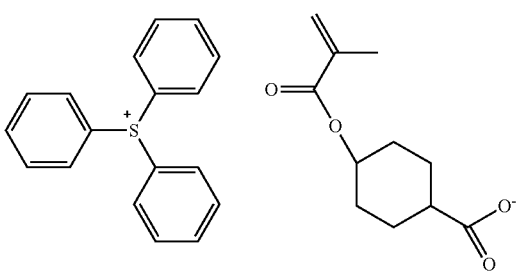

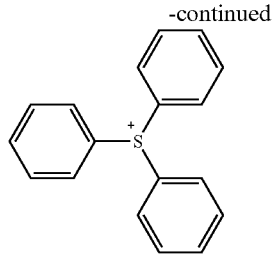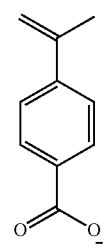
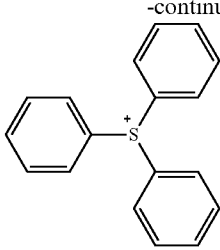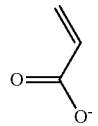
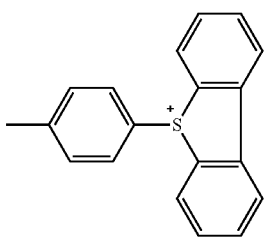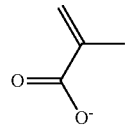
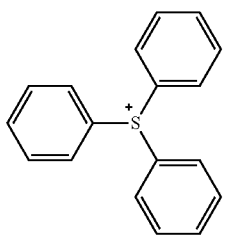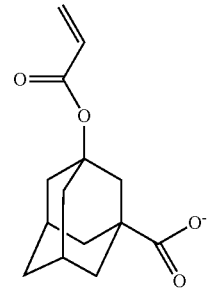
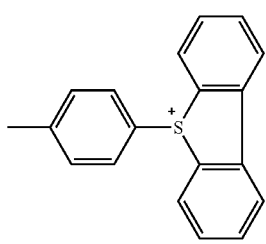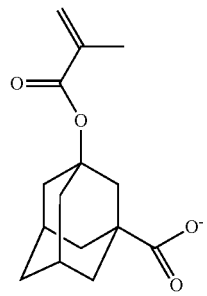
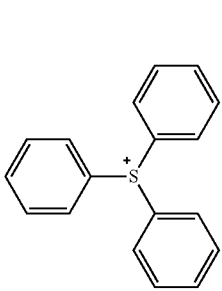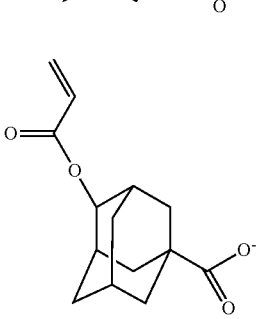
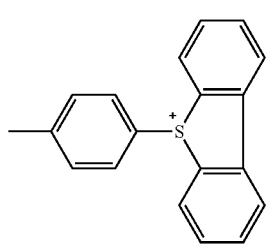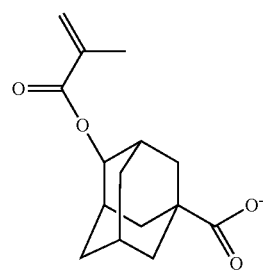
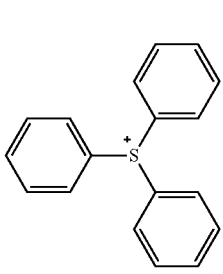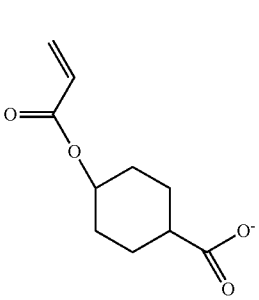
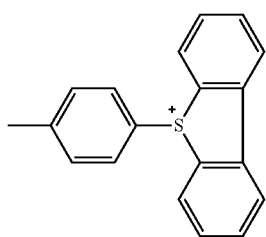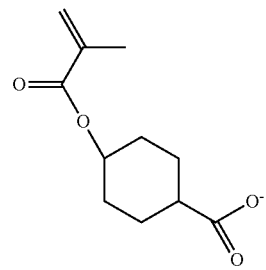
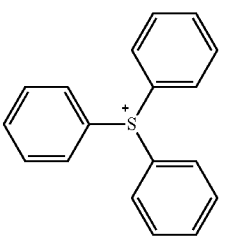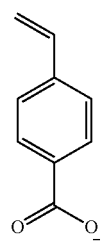
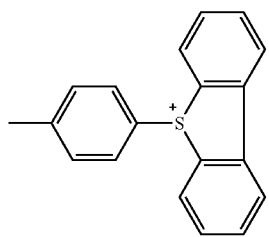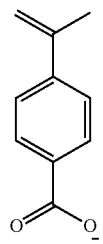
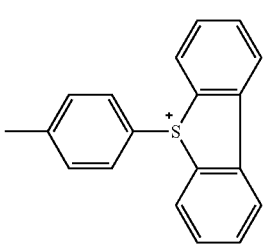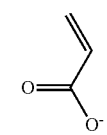

 
 
 
 

The salt represented by the formula (I-Pa) can be produced by reacting a sulfonium halide or an iodonium halide with the corresponding carboxylic acid or a silver salt thereof in a solvent.

A photoresist composition containing the salt represented by the formula (I-Pa) gives a photoresist pattern showing a good line edge roughness.

The polymer of the present invention comprises a structural unit derived from the salt represented by the formula (I-Pa). The polymer contains two or more kinds of the structural unit derived from the salt represented by the formula (I-Pa).

Examples of the polymer of the present invention include a polymer consisting of the structural unit derived from the salt represented by the formula (I-Pa) and a polymer comprising the structural unit derived from the salt represented by the formula (I-Pa) and one or more structural units other than the structural unit derived from the salt represented by the formula (I-Pa).

The polymer can be produced by polymerizing the salt represented by the formula (I-Pa), or the salt represented by the formula (I-Pa) and one or more monomers giving the structural units other than the structural unit derived from the salt represented by the formula (I-Pa) in a solvent in the presence of a polymerization initiator, and if necessary, a chain transfer agent.

Examples of the polymerization initiator include 2,2'-azoisobutyronitrile and 2,2'-azobis(2-methylbutyronitrile). Two or more kinds of the polymerization initiator can be used in combination. Examples of the chain transfer agent include dodecylmercaptan, mercaptoethanol and mercaptopropanol. Two or more kinds of the chain transfer agent can be used in combination. Examples of the solvent include 1,4-dioxane, toluene, tetrahydrofuran, acetone and methyl isobutyl ketone. Two or more kinds of the solvent can be used in combination. The used amount of the solvent is usually 0.8 to 10 parts by weight per 1 part of monomer components.

Examples of the polymer comprising the structural unit derived from the salt represented by the formula (I-Pa) include a polymer consisting of the structural unit derived from the salt represented by the formula (I-Pa), a polymer consisting of the structural unit derived from the salt represented by the formula (I-Pa) and a structural unit having an acid-labile group in its side chain, a polymer consisting of the structural unit derived from the salt represented by the formula (I-Pa) and a structural unit having no acid-labile group in its side chain, and a polymer consisting of the structural unit derived from the salt represented by the formula (I-Pa), a structural unit having an acid-labile group in its side chain and a structural unit having no acid-labile group in its side chain.

The polymer comprising the structural unit derived from the salt represented by the formula (I-Pa) and a structural unit having an acid-labile group in its side chain is a polymer being insoluble or poorly soluble in an aqueous alkali solution but becoming soluble in an aqueous alkali solution by the action of an acid.

Hereinafter, "the polymer comprising the structural unit derived from the salt represented by the formula (I-Pa) and a structural unit having an acid-labile group in its side chain" is simply referred to as Polymer (BA), and "the polymer comprising the structural unit derived from the salt represented by the formula (I-Pa) and no structural unit having acid-labile group in its side chain" is simply referred to as Polymer (BB). Polymer (BB) includes the polymer consisting of the structural unit derived from the salt represented by the formula (I-Pa) and the polymer comprising the structural unit derived from the salt represented by the formula (I-Pa) and a structural unit having no acid-labile group in its side chain.

Polymer (BA) can be produced by conducting the polymerization of the salt represented by the formula (I-Pa) and one or more monomers having an acid-labile group in its side chain and an olefinic double bond.

The content of the structural unit derived from the salt represented by the formula (I-Pa) in Polymer (BA) is usually 3 to 20 mol % and preferable 5 to 15 mol % based on total molar of the structural units in Polymer (BA).

In this specification, "an acid-labile group" means a group capable of being eliminated by the action of an acid.

Examples of the acid-labile group include a group represented by the formula (10):

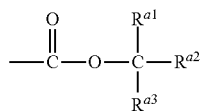
(10)

wherein $R^{a1}$, $R^{a2}$ and $R^{a3}$ independently each represent a C1-C8 aliphatic hydrocarbon group or a C3-C20 alicyclic hydrocarbon group, or $R^{a1}$ and $R^{a2}$ are bonded each other to form a C3-C20 ring.

Examples of the C1-C8 aliphatic hydrocarbon group include a C1-C8 alkyl group such as a methyl group, an ethyl group, a propyl group, an isopropyl group, a butyl group, a pentyl group, a hexyl group, a heptyl group and an octyl group. The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

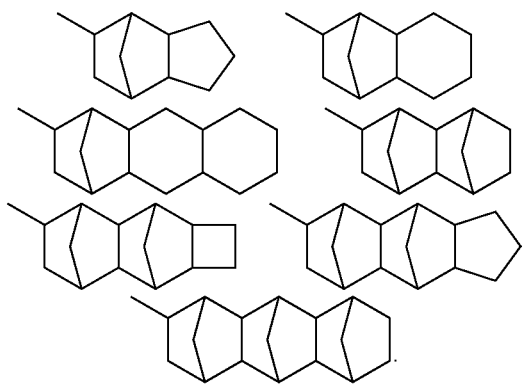

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

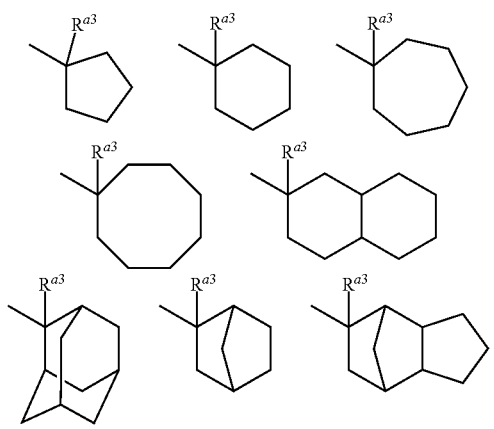

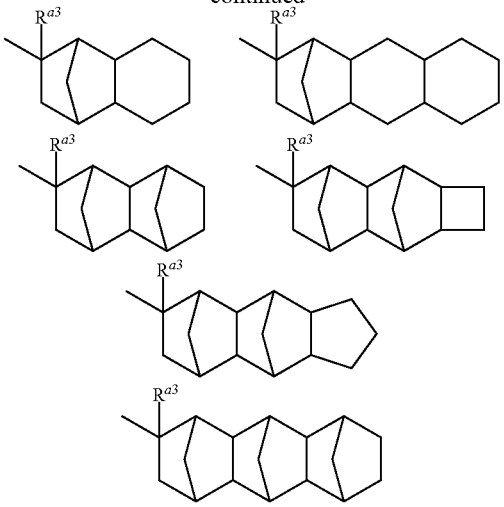

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

An acrylate monomer having an acid-labile group in its side chain or a methacryalte monomer having an acid-labile group in its side chain is preferable.

Preferable examples of the monomer include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate. Particularly when the 2-alkyl-2-adamantyl acrylate or the 2-alkyl-2-adamantyl methacrylate is used, a photoresist composition having excellent resolution tends to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used, a photoresist composition having excellent sensitivity and heat resistance tends to be obtained.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

Two or more kinds of monomers having a group or groups dissociated by the action of the acid may be used together, if necessary.

The content of the structural unit having an acid-labile group in its resin is usually 10 to 80% by mole based on total molar of all the structural units of Polymer (BA).

Polymer preferably contains one or more structural units having one or more highly polar substituents. Examples of the structural unit having one or more highly polar substituents include a structural unit having a hydrocarbon group having at least one selected from the group consisting of a hydroxyl group, a cyano group, a nitro group and an amino group and a structural unit having a hydrocarbon group having one or more —CO—O—, —CO—, —O—, —SO$_2$— or —S—. A structural unit having a saturated cyclic hydrocarbon group having a cyano group or a hydroxyl group, a structural unit having a saturated cyclic hydrocarbon group in which one or more —CH$_2$— replaced by —O— or —CO—, and a structural unit having a lactone structure in its side chain are preferable, and a structural unit having a bridged hydrocarbon group having one or more hydroxyl groups, and a structural unit having a bridged hydrocarbon group having —CO—O— or —CO— are more preferable. Examples thereof include a structural unit derived from 2-norbornene having one or more hydroxyl groups, a structural unit derived from acrylonitrile or methacrylonitrile, a structural unit derived from hydroxyl-containing adamantyl acrylate or hydroxyl-containing adamantyl methacrylate, a structural unit derived from styrene monomer such as p-hydroxystyrene and m-hydroxystyrene, a structural unit derived from a structural unit derived from 1-adamantyl acrylate or 1-adamantyl methacrylate, and a structural unit derived from acryloyloxy-γ-butyrolactone or methacryloyloxy-γ-butyrolactone having a lactone ring which may have an alkyl group.

Specific examples of the structural unit derived from hydroxyl-containing adamantyl acrylate or hydroxyl-containing adamantyl methacrylate include a structural unit derived from 3-hydroxy-1-adamantyl acrylate; a structural unit derived from 3-hydroxy-1-adamantyl methacrylate; a structural unit derived from 3,5-dihydroxy-1-adamantyl acrylate; and a structural unit derived from 3,5-dihydroxy-1-adamantyl methacrylate.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

When Polymer (BA) has a structural unit derived from hydroxyl-containing adamantyl acrylate or hydroxyl-containing adamantyl methacrylate, the content thereof is preferably 5 to 50% by mole based on 100% by mole of all the structural units of Polymer (BA).

Examples of the structural unit derived from a monomer having a lactone ring which may have an alkyl group include a structural unit derived from acryloyloxy-γ-butyrolactone, a structural unit derived from methacryloyloxy-γ-butyrolactone and structural units represented by the formulae (a) and (b):

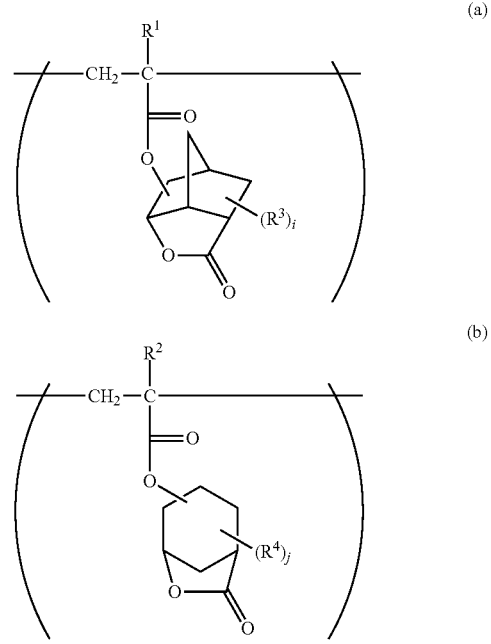

wherein R$^1$ and R$^2$ independently each represents a hydrogen atom or a methyl group, R$^3$ and R$^4$ are independently in each occurrence a hydrogen atom, a methyl group, a trifluoromethyl group or a halogen atom, and i and j independently each represents an integer of 1 to 3.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers giving structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

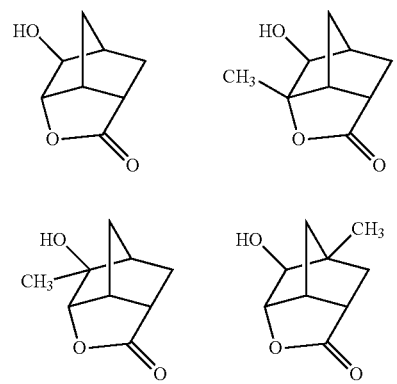

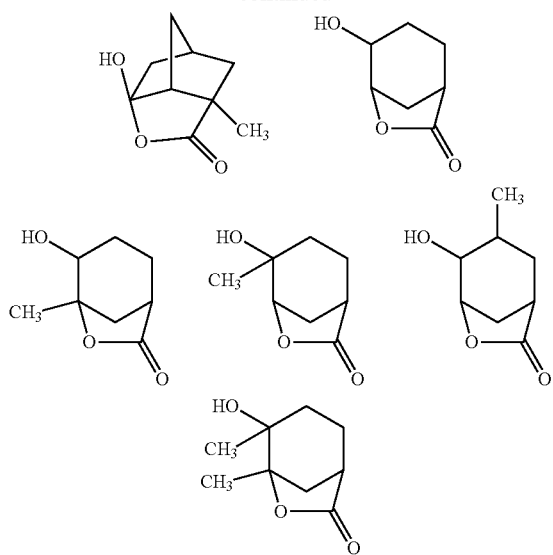

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

When Polymer (BA) has a structural unit derived from a monomer having a lactone ring which may have an alkyl group, the content thereof is preferably 5 to 50% by mole based on 100% by mole of all the structural units of Polymer (BA).

Among them, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (a) and the structural unit represented by the formula (b) are preferable, because a photoresist composition having good resolution and adhesiveness of photoresist to a substrate tends to be obtained.

When the exposing is conducted using KrF excimer laser, Polymer (BA) preferably has a structural unit derived from a styrene monomer such as p-hydroxystyrene and m-hydroxystyrene, and the content thereof is preferably 5 to 90% by mole based on 100% by mole of all the structural units of Polymer (BA).

Polymer (BA) can contain the other structural unit or units. Examples thereof include a structural unit derived from acrylic acid or methacrylic acid, a structural unit derived from an alicyclic compound having an olefinic double bond such as a structural unit represented by the formula (c):

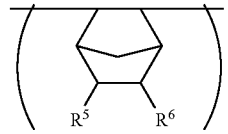

wherein $R^5$ and $R^6$ each independently represents a hydrogen atom, a C1-C3 alkyl group, a carboxyl group, a cyano group or a —COOU group in which U represents an alcohol residue, or $R^5$ and $R^6$ can be bonded together to form a carboxylic anhydride residue represented by —C(=O)OC(=O)—, a structural unit derived from an aliphatic unsaturated dicarboxylic anhydride such as a structural unit represented by the formula (d):

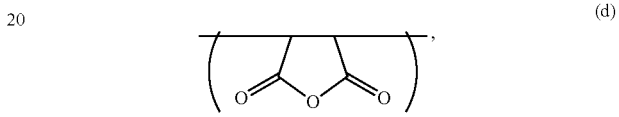

or
a structural unit represented by the formula (e):

$$\left(\!-CH_2-\overset{\phantom{|}}{\underset{\phantom{|}}{C}}\overset{O}{\underset{O}{\diagdown\!\diagup}}\!\right)\!.$$ (e)

In $R^5$ and $R^6$, examples of the C1-C3 alkyl group include a methyl group, an ethyl group, a propyl group and an isopropyl group. The —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer giving the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

Polymer (BA) usually has 2,500 or more of the weight-average molecular weight, preferably 2,700 or more of the weight-average molecular weight, and more preferably 3,000 or more of the weight-average molecular weight, and Polymer (BA) usually has 100,000 or less of the weight-average molecular weight, preferably 50,000 or less of the weight-average molecular weight, and more preferably 40,000 or less of the weight-average molecular weight. The weight-average molecular weight can be measured with gel permeation chromatography.

Polymer (BB) contains the structural unit derived from the salt represented by the formula (I-Pa) and Polymer (BB) can contain the structural unit having no acid-labile group in its side chain. Examples of the structural unit having no acid-labile group in its side chain include the same as described above.

The content of the structural unit derived from the salt represented by the formula (I-Pa) in Polymer (BB) is usually 5 to 100 mol % and preferable 10 to 70 mol % based on total molar of the structural units in Polymer (BB).

Polymer (BB) usually has 2,500 or more of the weight-average molecular weight, preferably 3,000 or more of the weight-average molecular weight, and more preferably 4,000 or more of the weight-average molecular weight, and Polymer (BB) usually has 50,000 or less of the weight-average molecular weight, preferably 30,000 or less of the weight-average molecular weight, and more preferably 15,000 or less of the weight-average molecular weight. The weight-average molecular weight can be measured with gel permeation chromatography.

The photoresist composition of the present invention comprises the polymer comprising the structural unit derived from the salt represented by the formula (I-Pa) and an acid generator.

When the photoresist composition contains Polymer (BA) as the polymer comprising the structural unit derived from the salt represented by the formula (I-Pa), the content of Polymer (BA) is usually 80 to 99.9% by weight based on sum of solid component. Herein, "solid component" means the components other than a solvent in the photoresist composition.

When the photoresist composition contains Polymer (BB) as the polymer comprising the structural unit derived from the salt represented by the formula (I-Pa), the content of Polymer (BB) is usually 0.1 to 20% by weight based on sum of solid component.

The photoresist composition of the present invention can contain one or more resins having no structural unit derived from the salt represented by the formula (I-Pa), which is insoluble or poorly soluble in an aqueous alkali solution but becomes soluble in an aqueous alkali solution by the action of an acid. The content of the resin is usually 80 to 99.9% by weight based on sum of solid component.

The photoresist composition of the present invention comprises the salt represented by the formula (I-Pa), an acid generator and a resin comprising a structural unit having an acid-labile group and being insoluble or poorly soluble in an aqueous alkali solution but becoming soluble in an aqueous alkali solution by the action of an acid. The resin has the above-mentioned structural unit having an acid-labile group. The photoresist composition can contain the polymer comprising the structural unit derived from the salt represented by the formula (I-Pa). The content of the resin is usually 80 to 99.9% by weight based on sum of solid component. The content of the salt represented by the formula (I-Pa) is usually 0.1 to 20 parts by weight and preferably 1 to 20 parts by weight per 100 parts by weight of the resin component. Herein, "resin component" means the resin and the polymer comprising the structural unit derived from the salt represented by the formula (I-Pa).

The resin can be obtained by conducting polymerization reaction of the corresponding monomer or monomers. The polymerization reaction is usually carried out in the presence of a radical initiator. This polymerization reaction can be conducted according to known methods.

Examples of the acid generator include a sulfonic acid generator, and an acid generator having one or more fluorine atoms is preferable. Preferable examples of the acid generator include a salt represented by the formula (I):

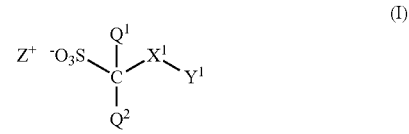

wherein $Q^1$ and $Q^2$ each independently represent a fluorine atom or a C1-C4 perfluoroalkyl group,
$X^1$ represents a single bond or a C1-C17 saturated hydrocarbon group which can have one or more substituents, and one or more methylene groups in the saturated hydrocarbon group can be replaced by —O— or —CO—,
$Y^1$ represents a C1-C36 aliphatic hydrocarbon group, a C3-C36 alicyclic hydrocarbon group or a C6-C24 aromatic hydrocarbon group, and the aliphatic hydrocarbon group, the alicyclic hydrocarbon group and the aromatic hydrocarbon group can have one or more substituents, and one or more methylene groups in the aliphatic hydrocarbon group and the alicyclic hydrocarbon group can be replaced by —O— or —CO—, $Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated hydrocarbon group include a C1-C17 alkylene group and a divalent group having an alicyclic hydrocarbon group. Examples of the alkylene group include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an isopropylene group, a sec-bytylene group and a tert-butylene group. Examples of the divalent group having an alicyclic hydrocarbon group include the following groups represented by the formulae $(X^1$-A$)$ to $(X^1$-C$)$:

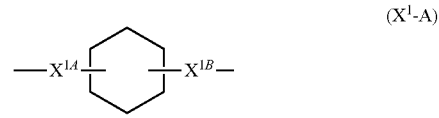

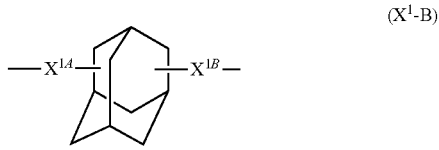

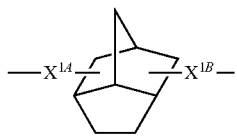
(X¹-C)

wherein $X^{1A}$ and $X^{1B}$ independently each represent a C1-C6 alkylene group which can have one or more substituents, with the proviso that total carbon number of the group represented by the formula (X¹-A), (X¹-B) or (X¹-C) is 1 to 17.

One or more methylene groups in the C1-C6 alkylene group can be replaced by —O— or —CO—.

Examples of the saturated hydrocarbon group in which one or more methylene groups are replaced by —O— or —CO— include —CO—O—$X^{10}$—, —CO—O—$X^{11}$—CO—O—, —$X^{12}$—O—CO— and —$X^{13}$—O—$X^{14}$—, wherein $X^{10}$ and $X^{12}$ independently each represent a single bond or a C1-C15 saturated hydrocarbon group, $X^{11}$ represents a single bond or a C1-C13 saturated hydrocarbon group, $X^{13}$ represents a single bond or a C1-C16 saturated hydrocarbon group, and $X^{14}$ represents a single bond or a C1-C16 saturated hydrocarbon group, with proviso that total carbon number of $X^{13}$ and $X^{14}$ is 1 to 16. Preferred is —CO—O—$(CH_2)_h$— wherein h is an integer of 0 to 10.

Examples of the substituent in $Y^1$ include a halogen atom, a hydroxyl group, a cyano group, an oxo group, a glycidyloxy group, a C2-C4 acyl group, a C1-C6 alkoxy group, a C2-C7 alkoxycarbonyl group, a C1-C12 aliphatic hydrocarbon group, a C3-C20 alicyclic hydrocarbon group, a C6-C20 aromatic hydrocarbon group and a C7-C21 aralkyl group.

Examples of the anion part of the same represented by the formula (I) include anion parts represented by the formulae (IA), (IB), (IC) and (ID), and the anion parts represented by the formulae (IA) and (IB) are preferable.

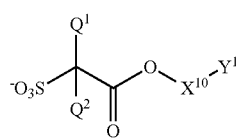
(IA)

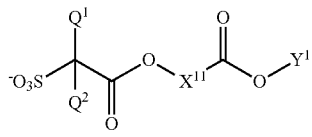
(IB)

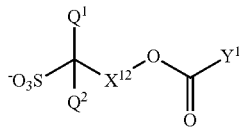
(IC)

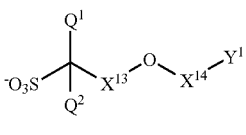
(ID)

wherein $Q^1$, $Q^2$, $X^{10}$, $X^{11}$, $X^{12}$, $X^{13}$, $X^{14}$ and $Y^1$ are the same as defined above.

$Y^1$ is preferably a C3-C36 alicyclic hydrocarbon group which can have one or more substituents and in which one or more methylene groups can be replaced by —O— or —CO—. Examples thereof include groups represented by the formulae (W1) to (W25):

(W1)

(W2)

(W3)

(W4)

(W5)

(W6)

(W7)

(W8)

(W9)

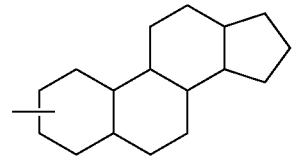
(W10)

(W11)

(W12)

(W13) 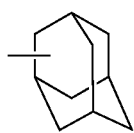

(W14) 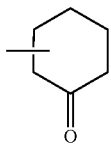

(W15) 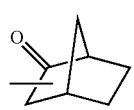

(W16) 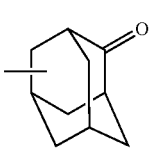

(W17) 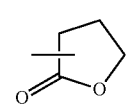

(W18) 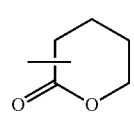

(W19) 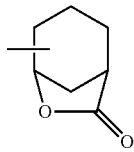

(W20) 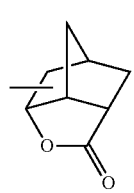

(W21) 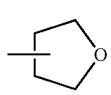

(W22) 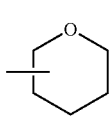

(W23) 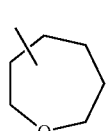

(W24) 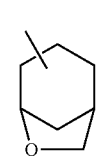

(W25) 

The above-mentioned groups represented by the formulae (W1) to (W25) can have one or more substituents. Among them, a group represented by the formula (Y1), (Y2), (Y3) and (Y4):

(Y1) 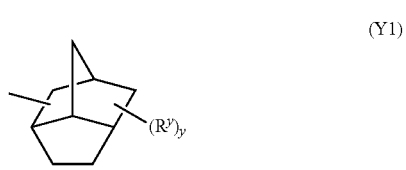

(Y2) 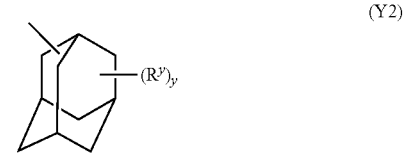

(Y3) 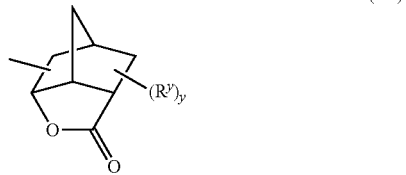

(Y4) 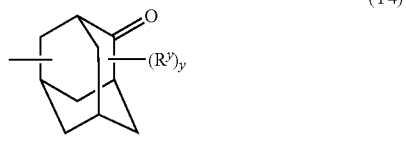

wherein $R^y$ represents a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, and y represents an integer of 0 to 6, is preferable.

Examples of $Y^1$ include the followings:

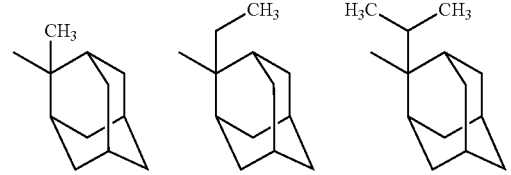

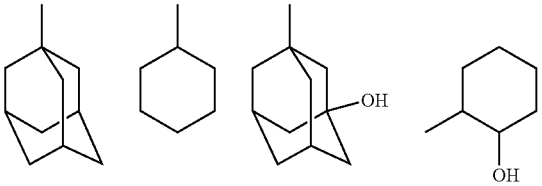

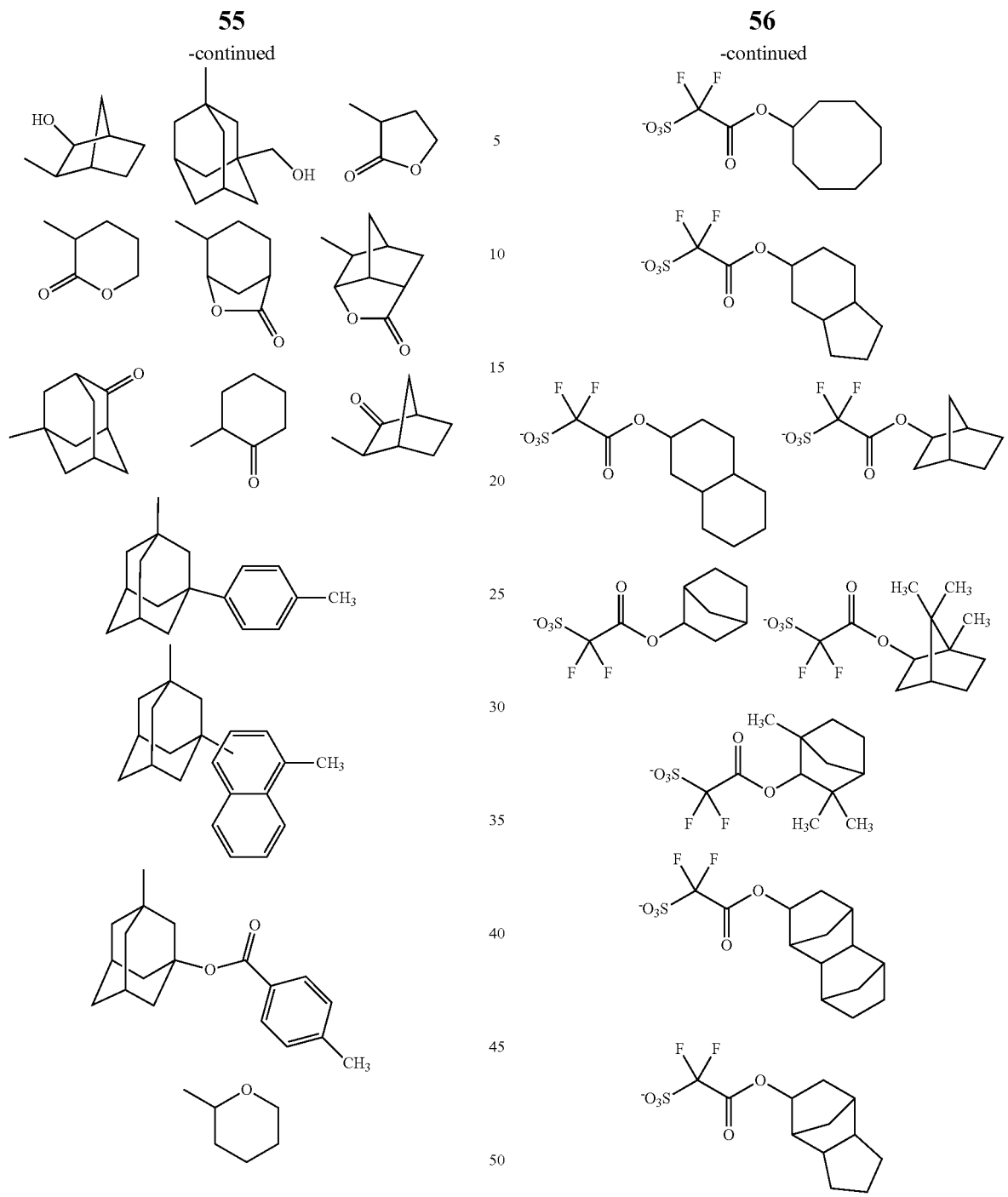
Examples of the anion part represented by the formula (IA) include the followings.
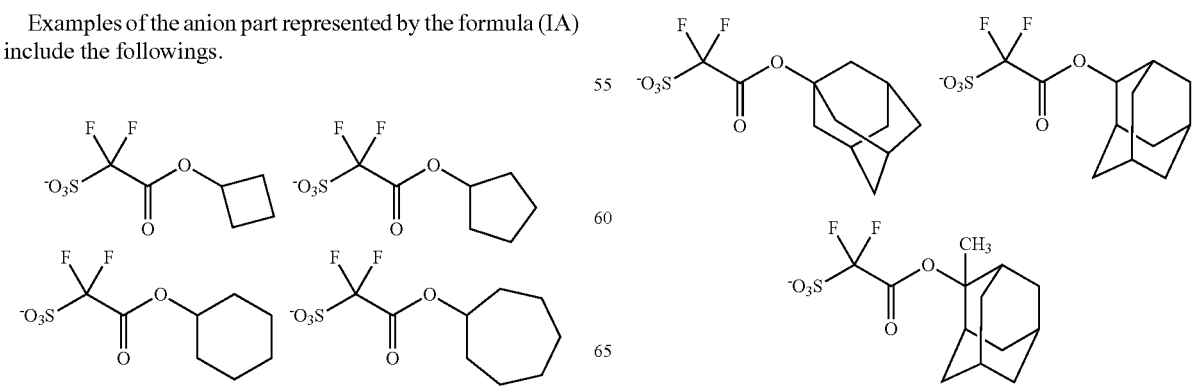

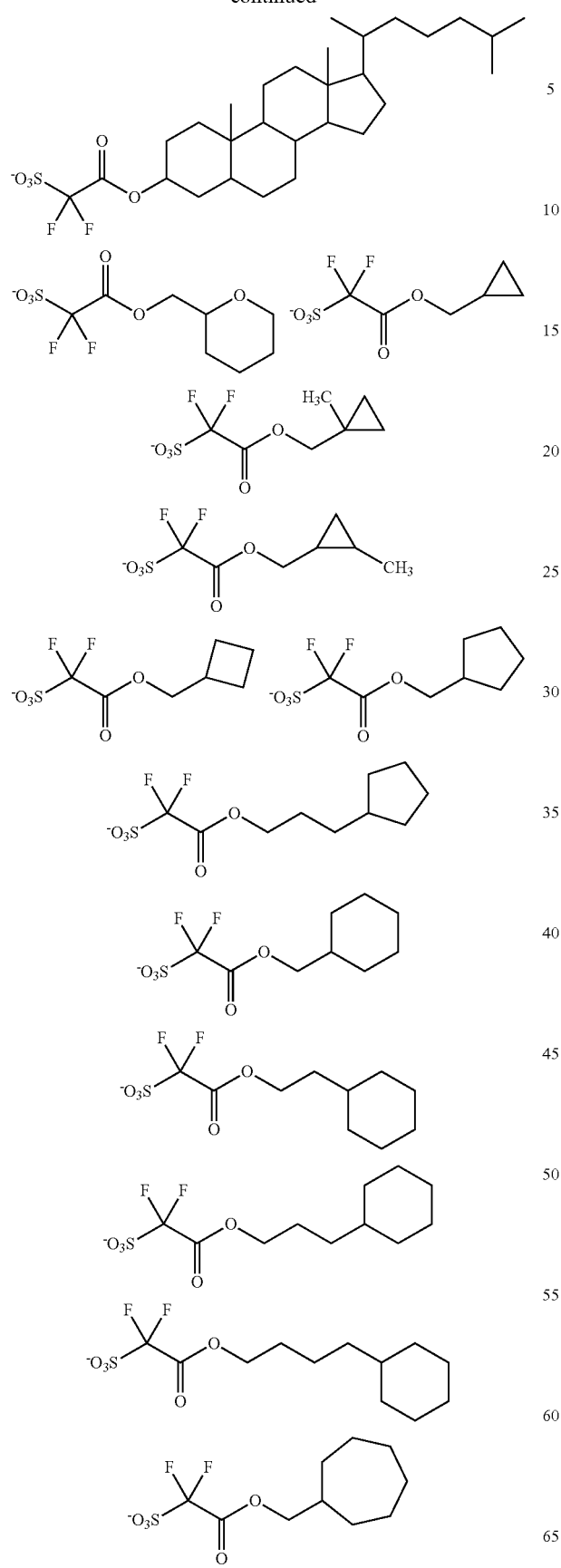
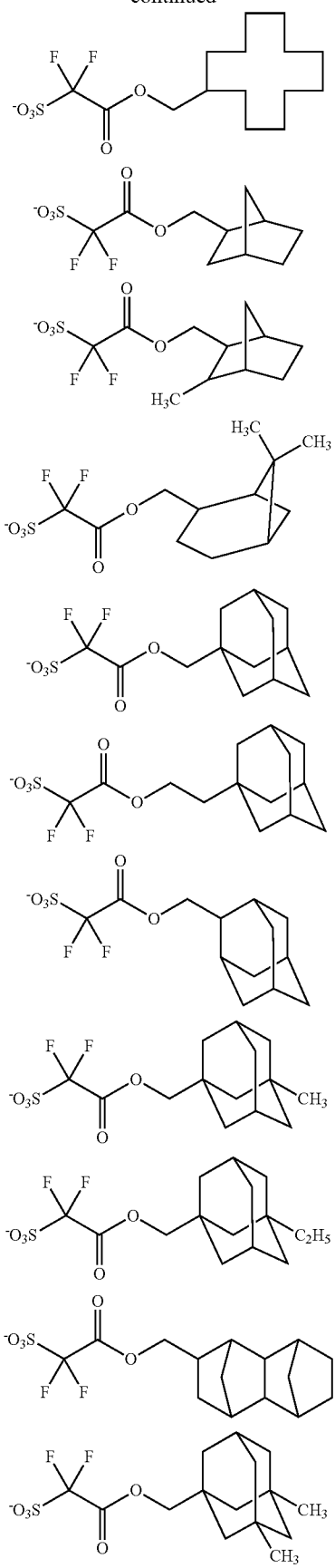

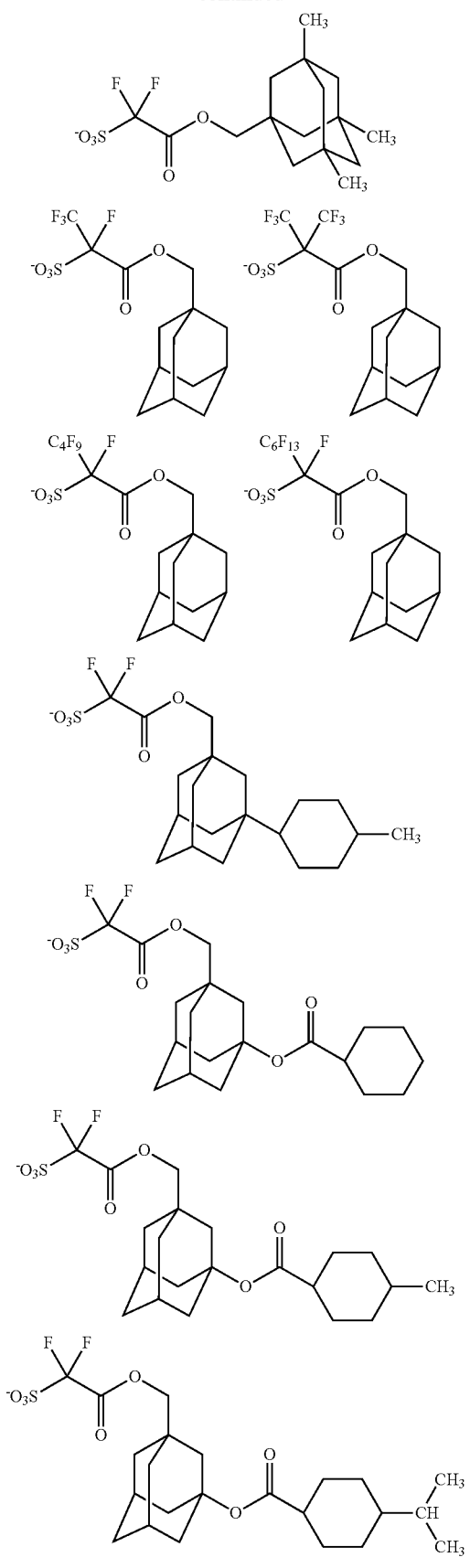
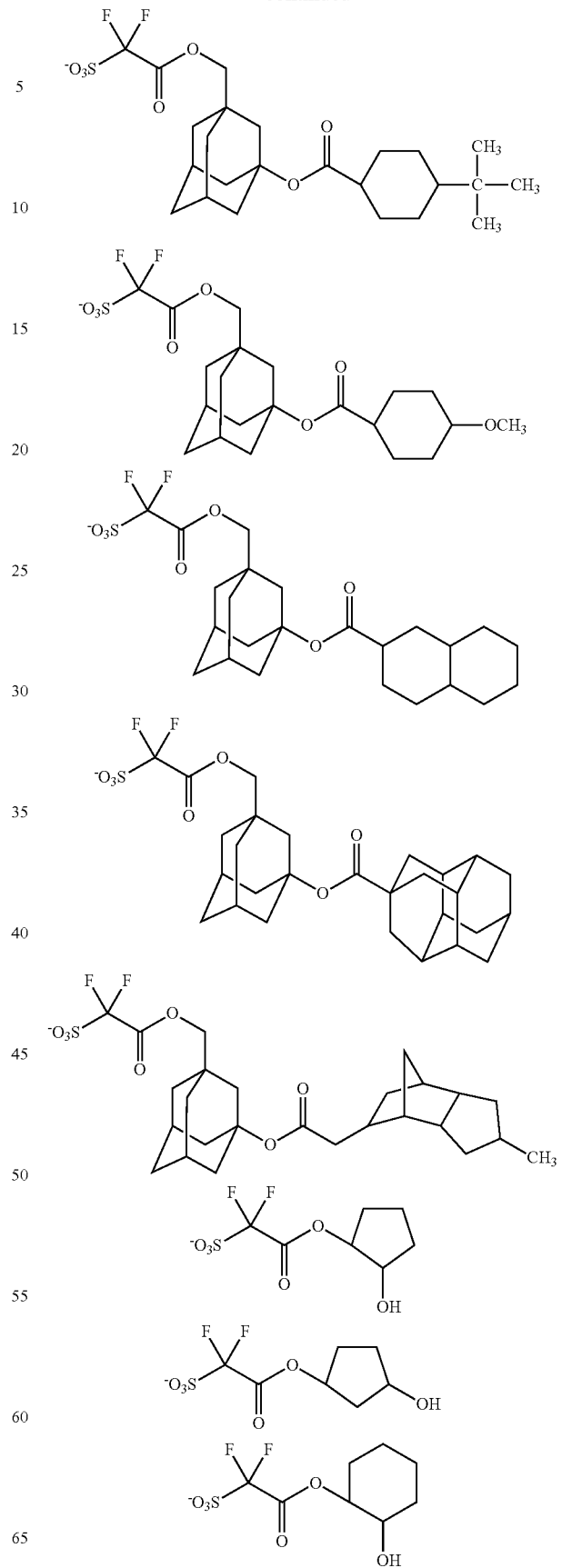

61
-continued
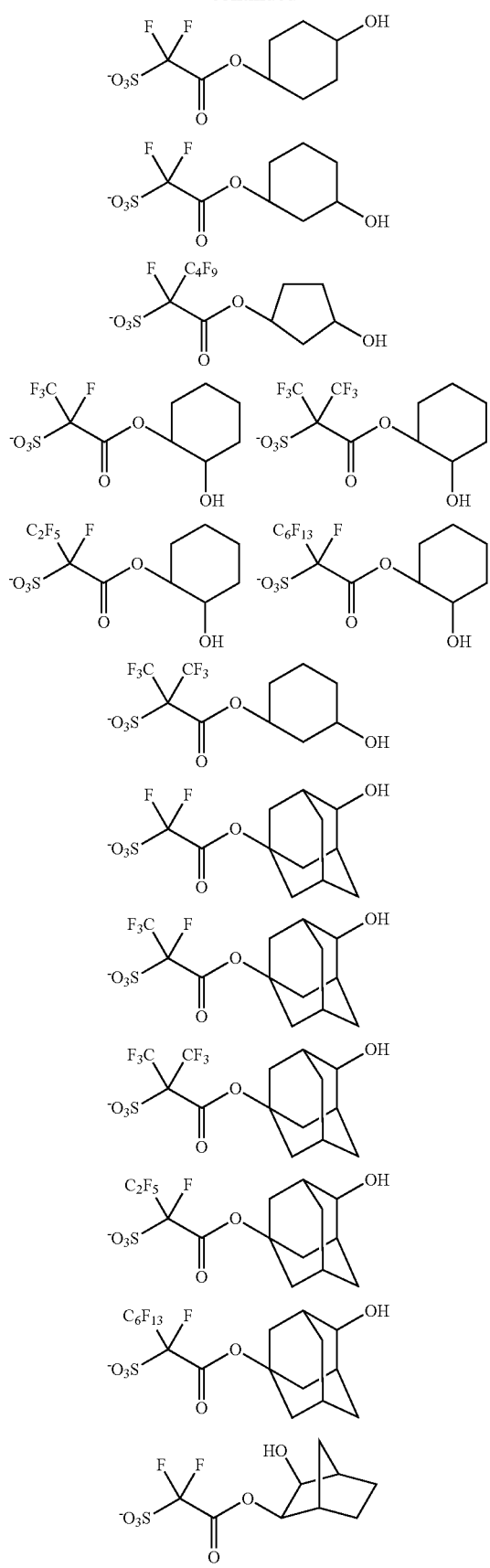
62
-continued
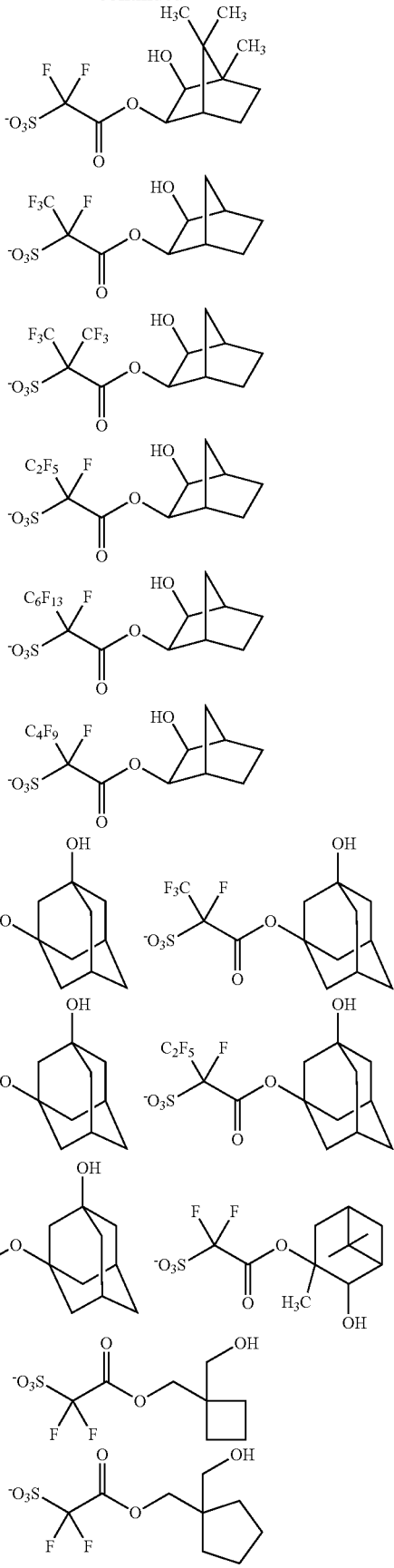

-continued
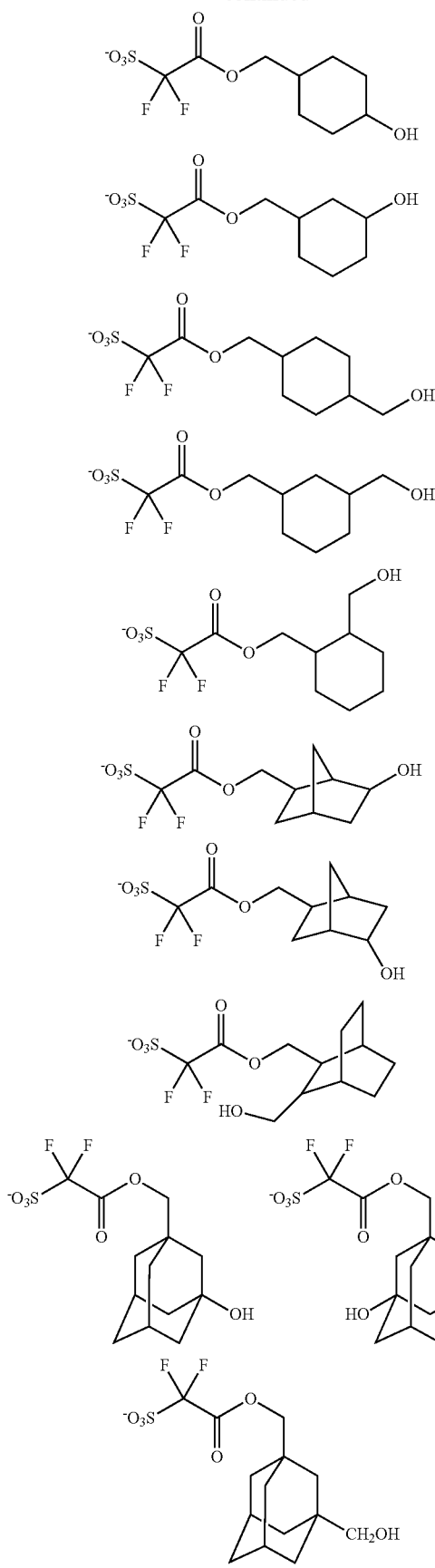
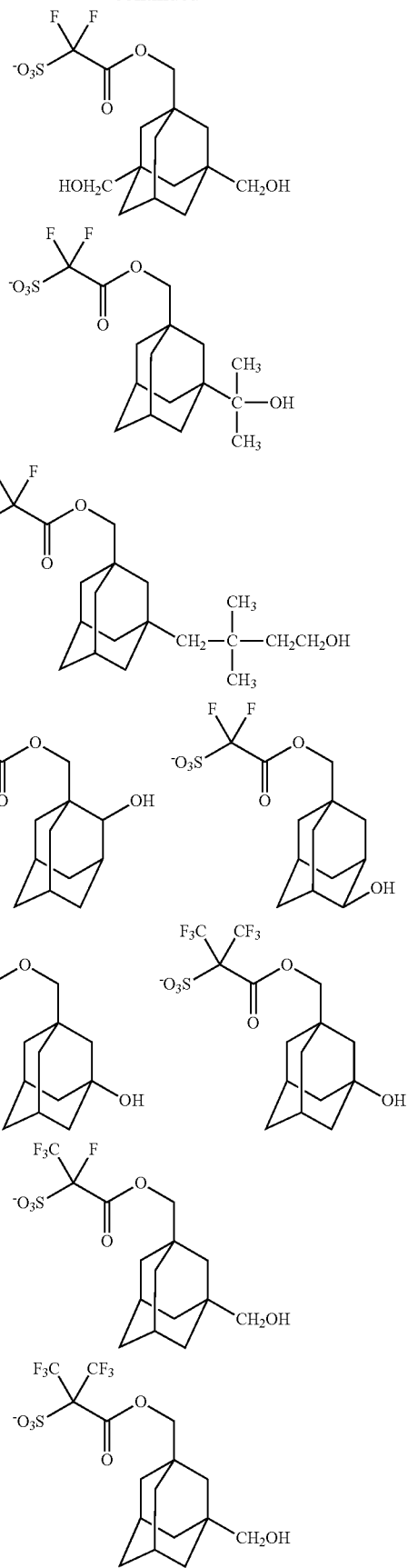

-continued
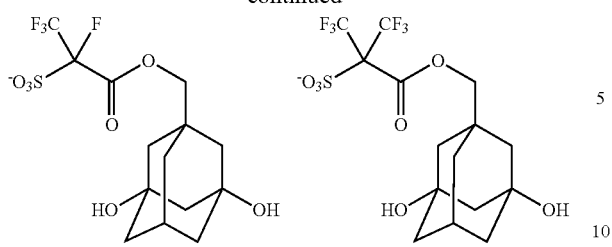
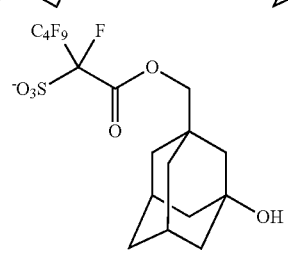
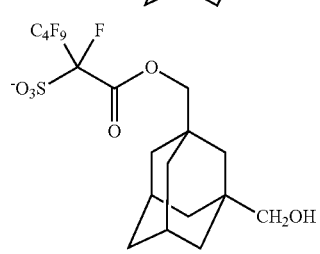
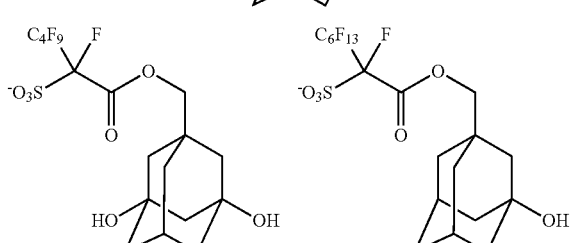
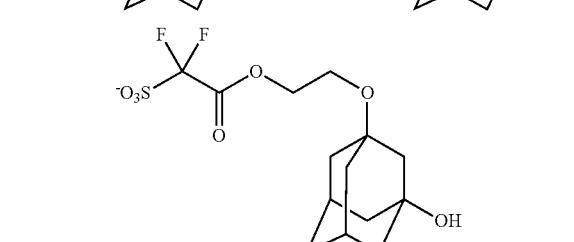
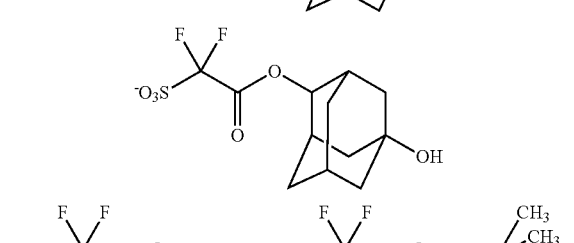
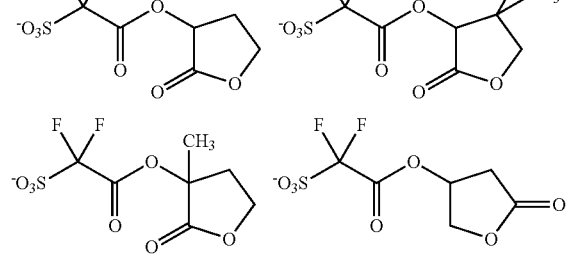
-continued
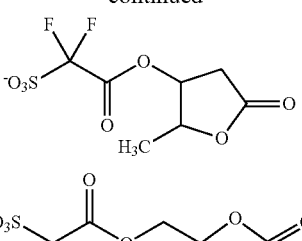
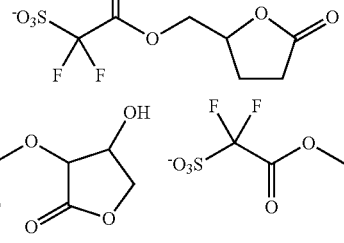
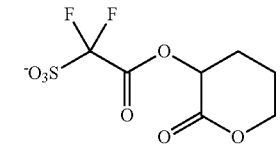
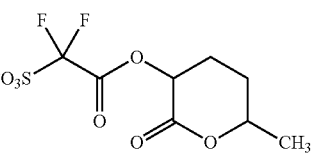
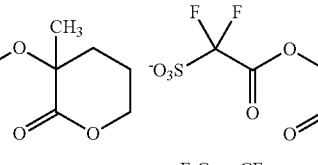
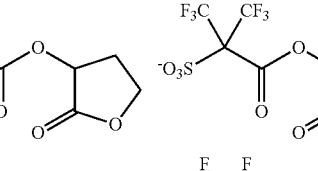
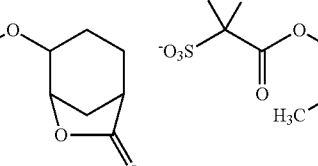
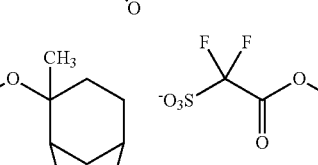
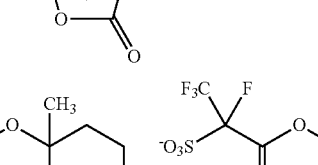
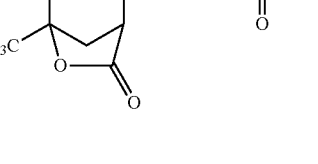

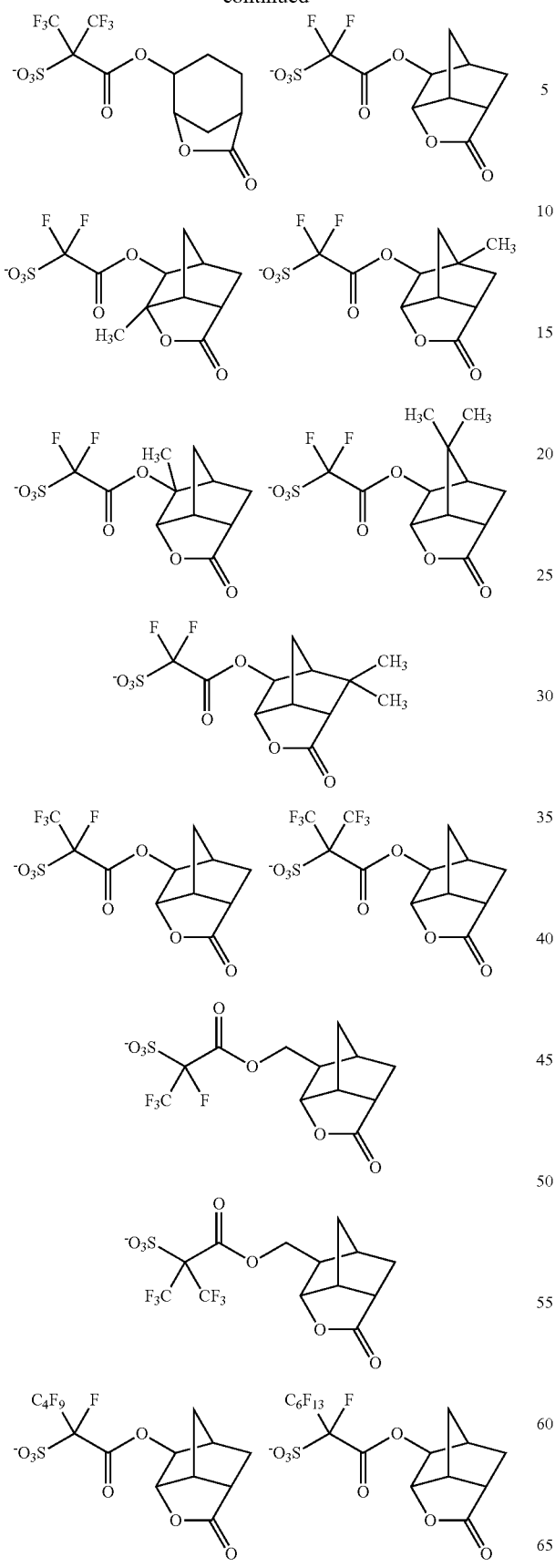
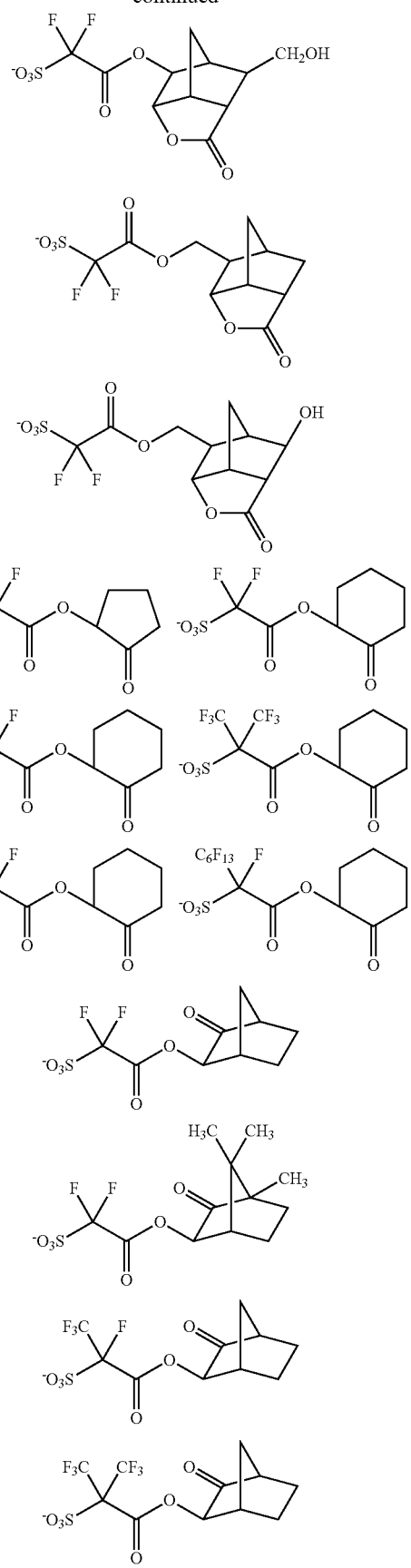

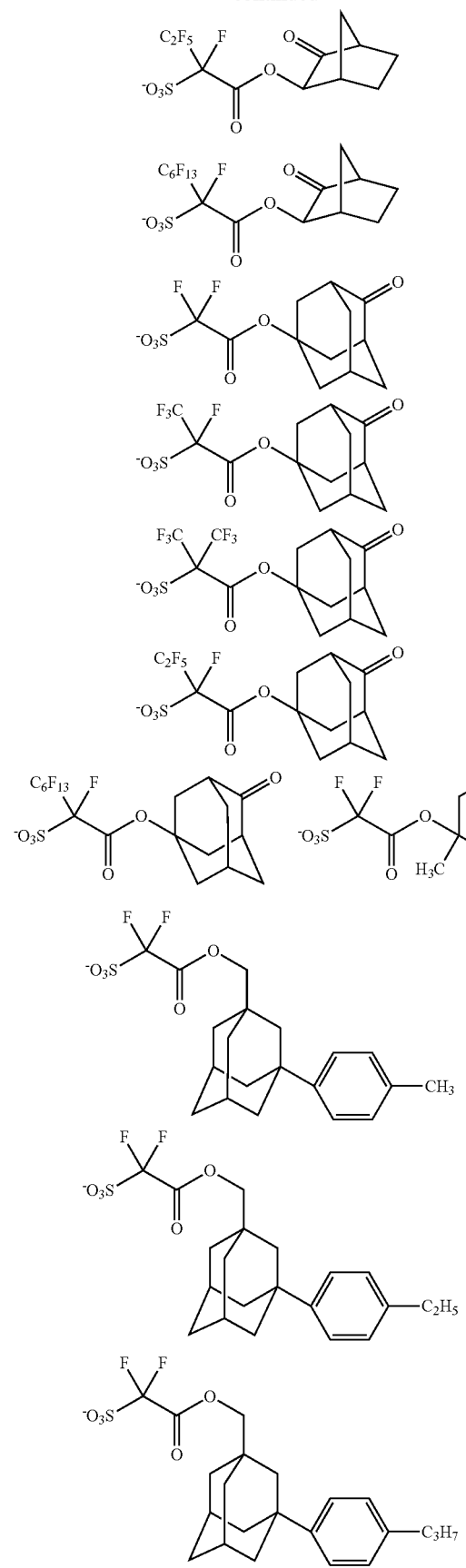
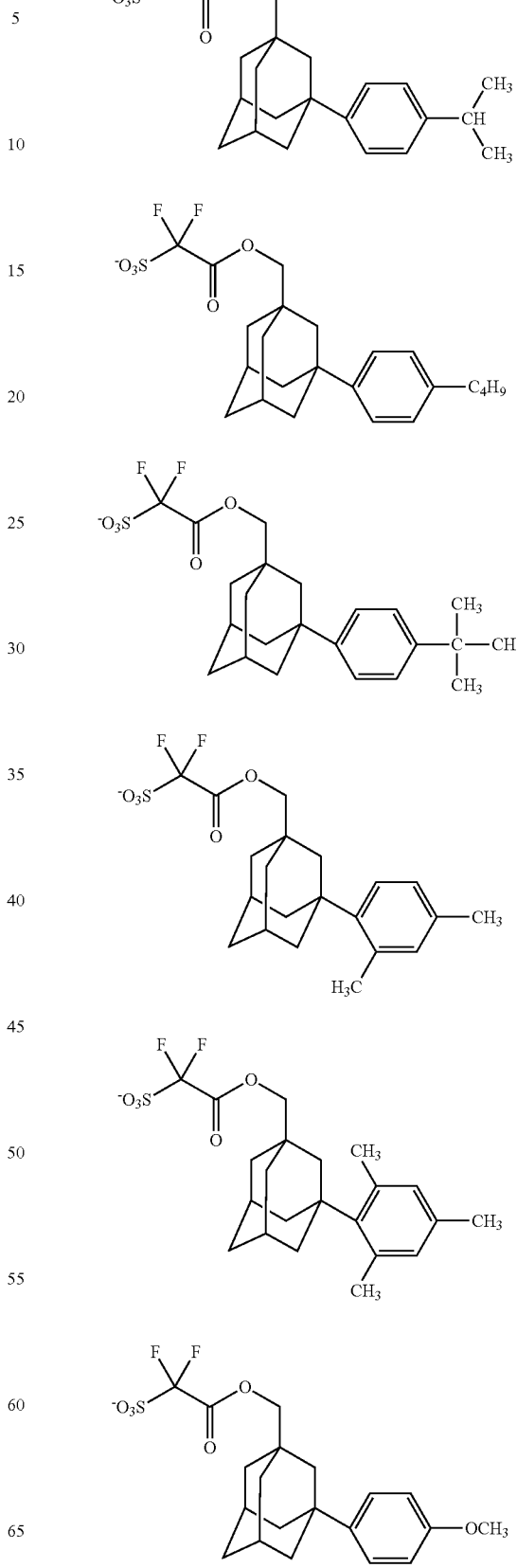

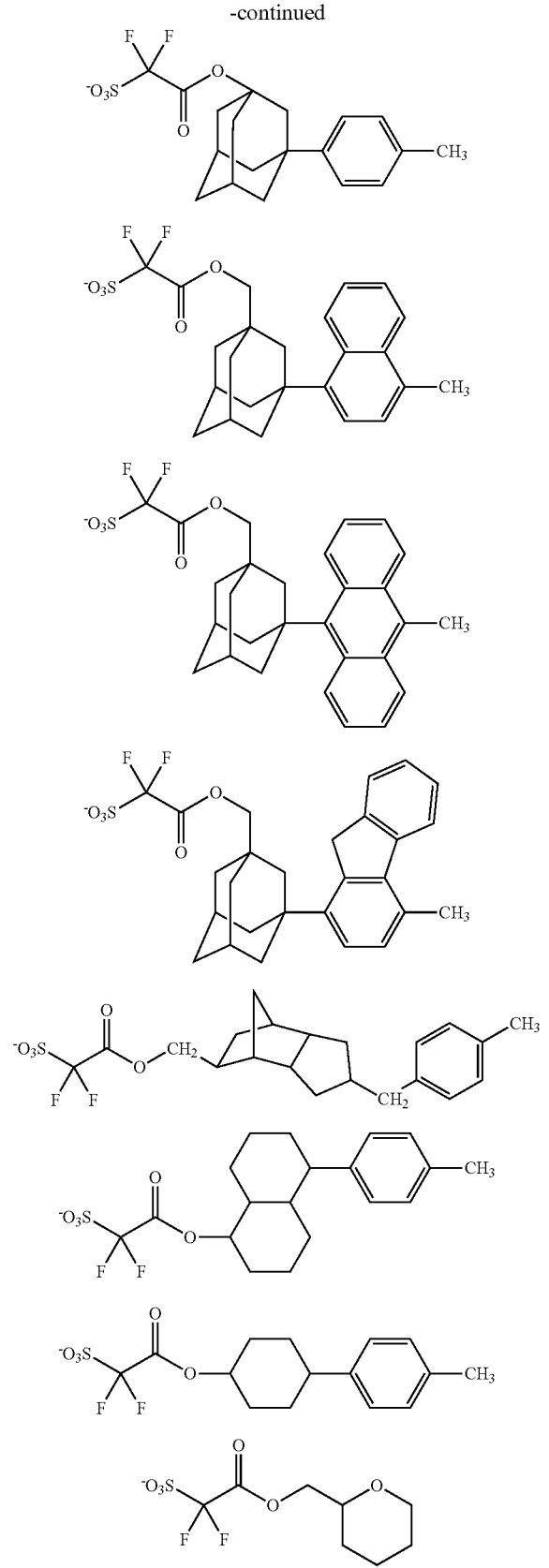
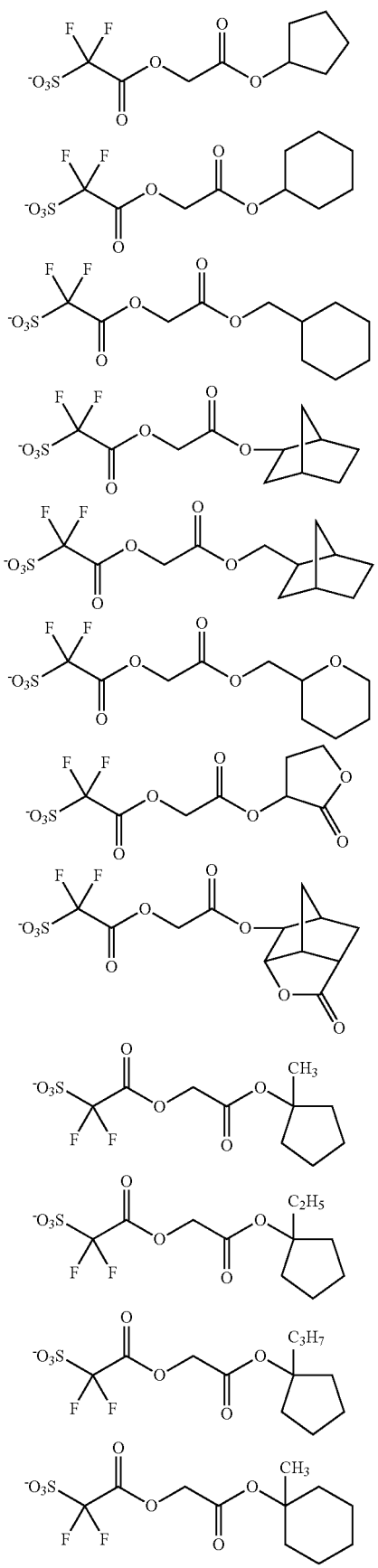
Examples of the anion part represented by the formula (IB) include the followings.

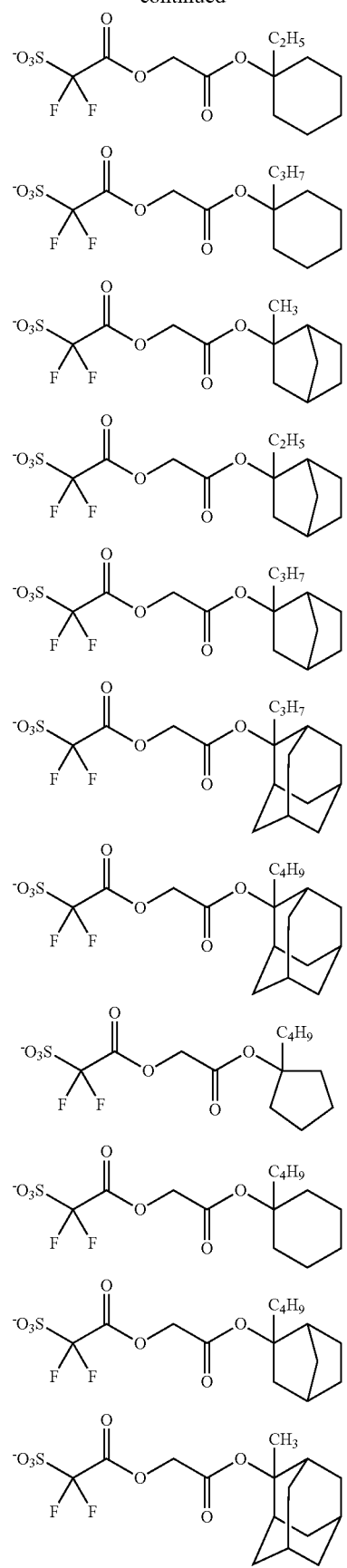
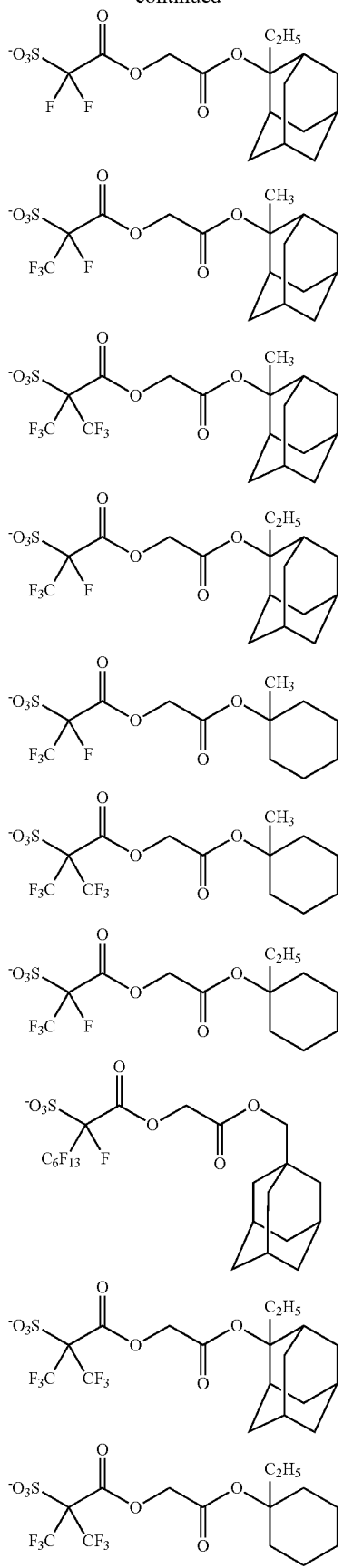

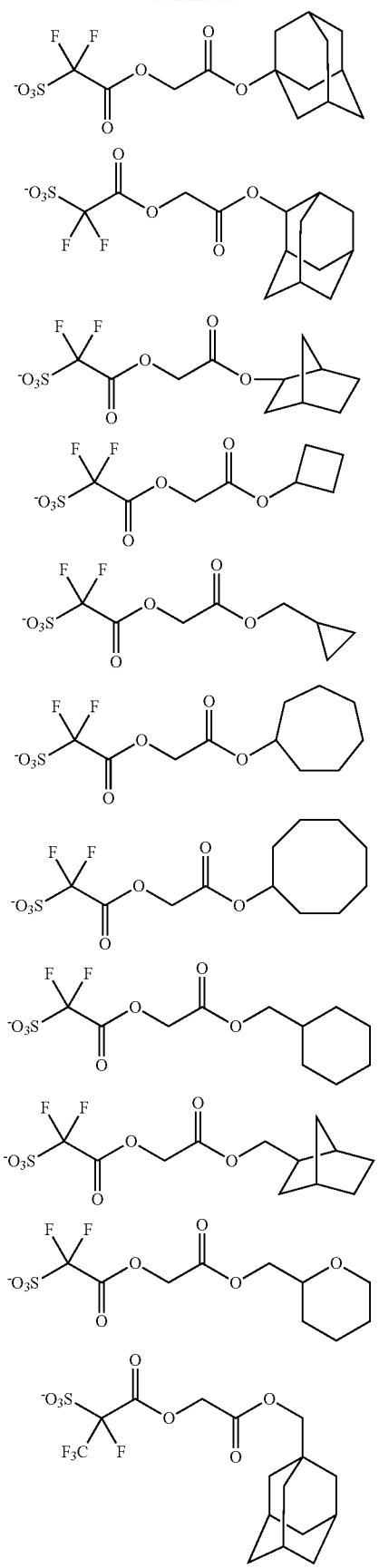
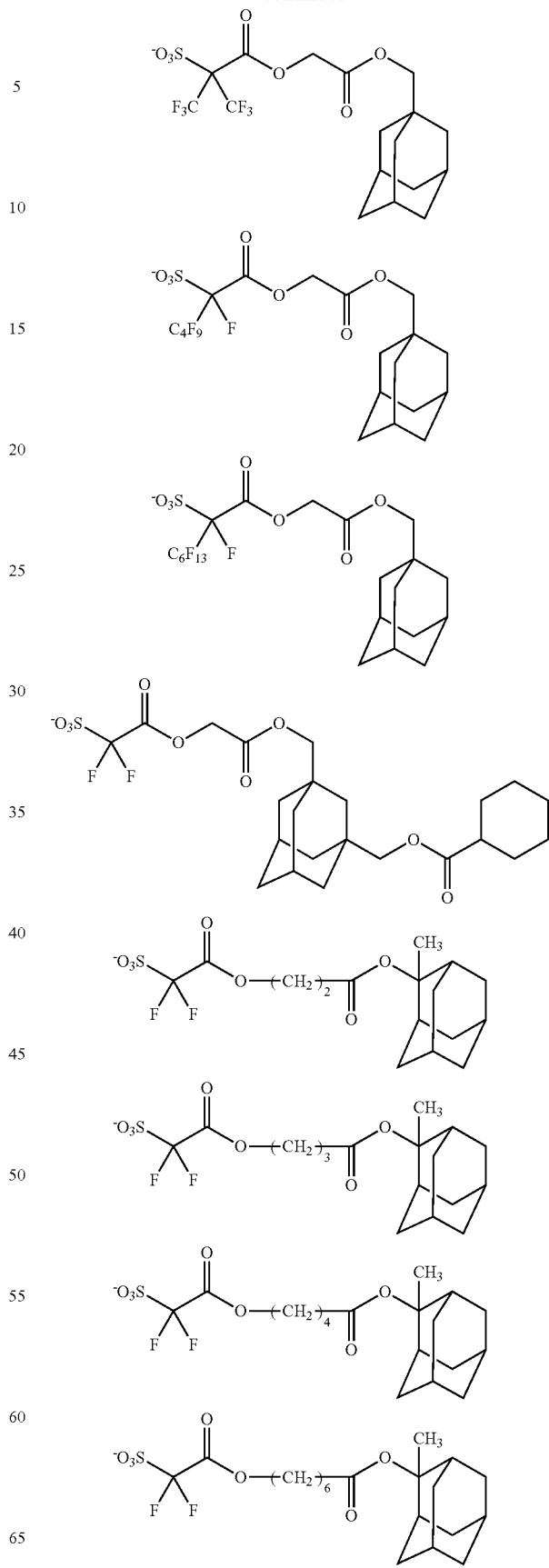

77
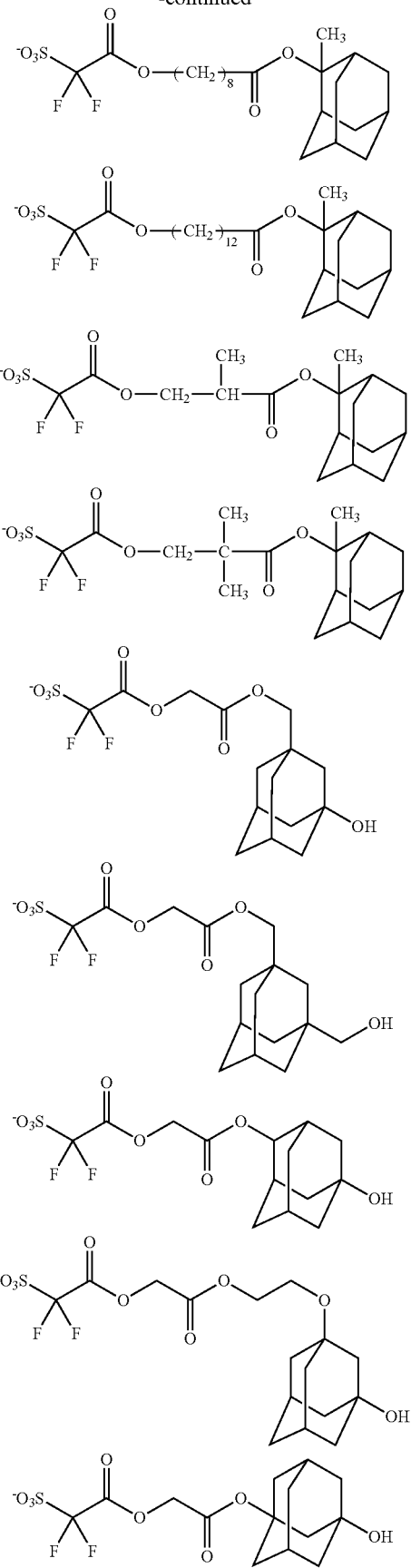
78
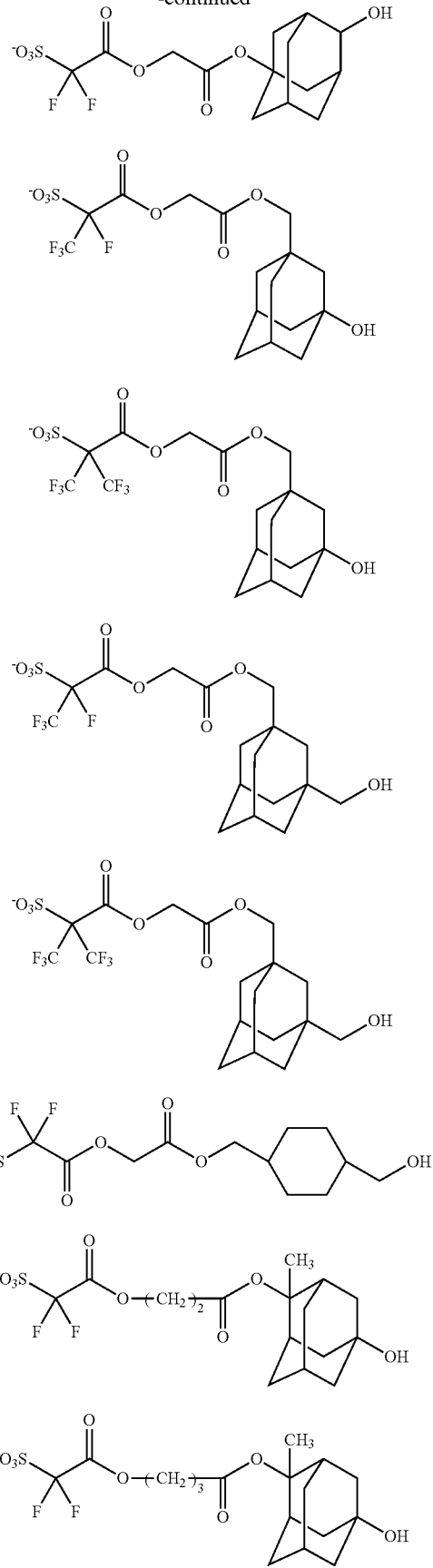

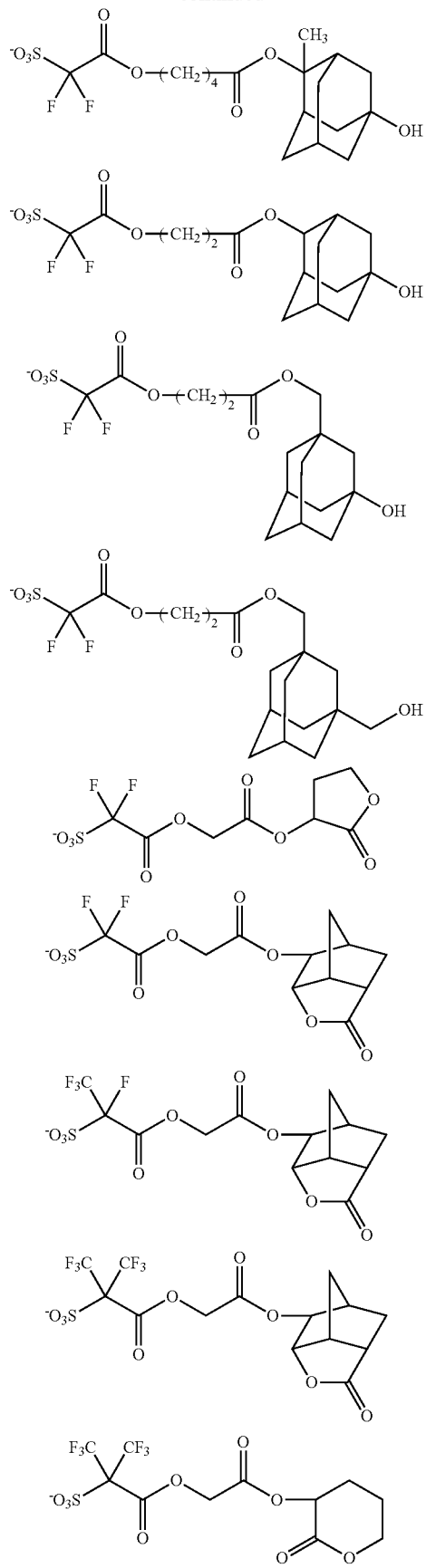
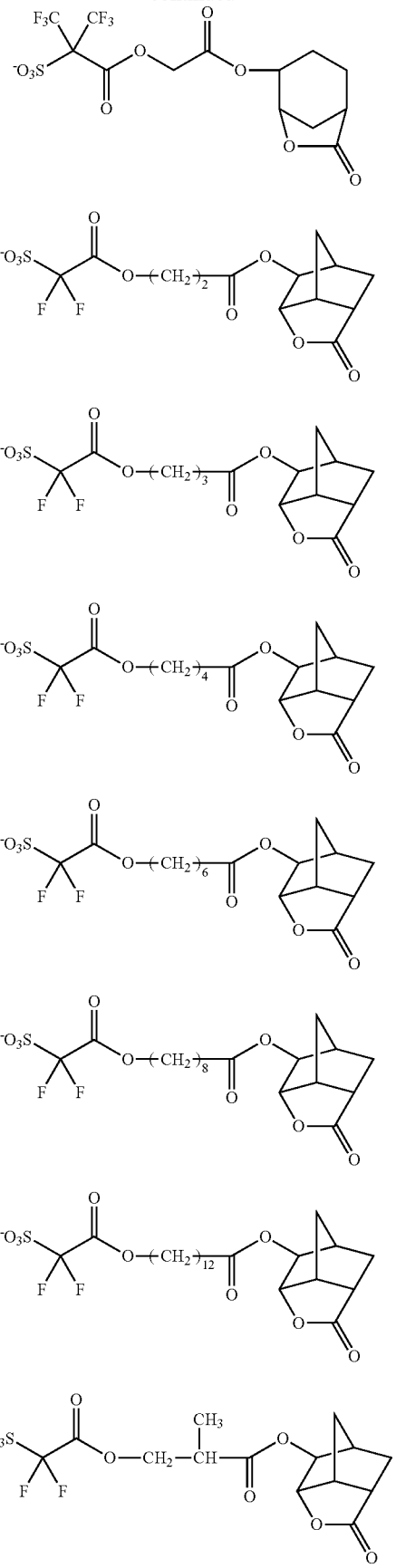

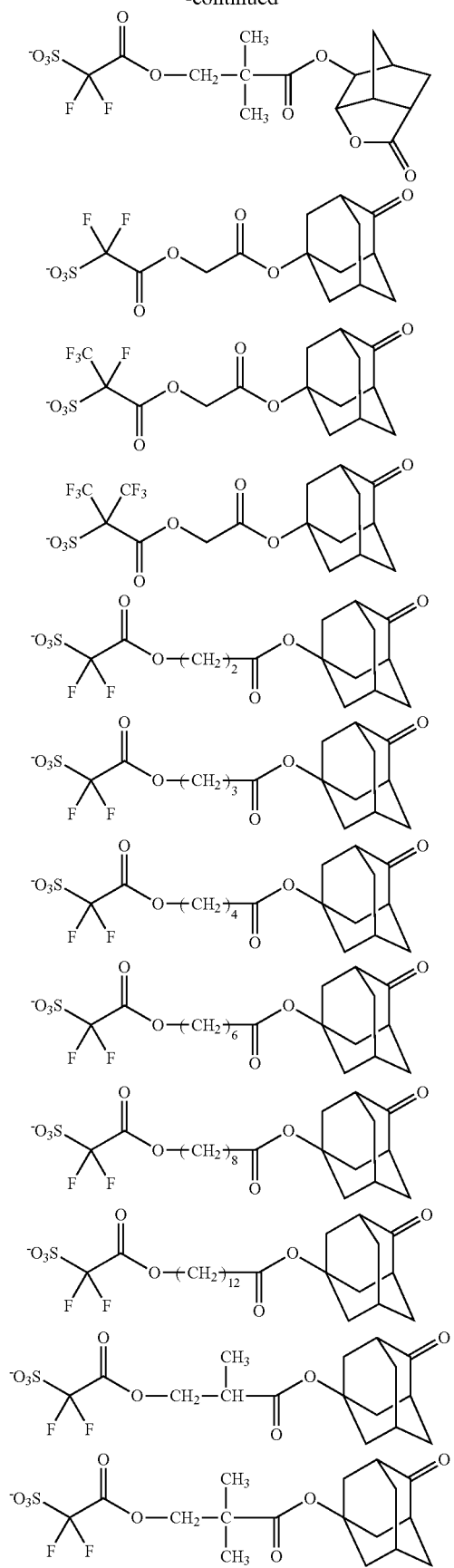
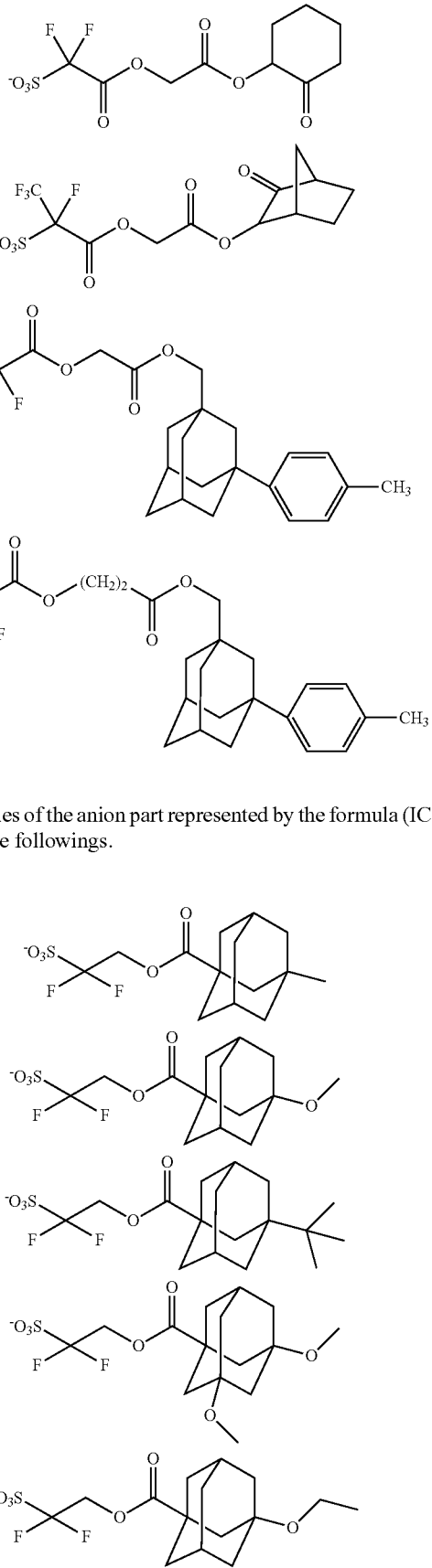
Examples of the anion part represented by the formula (IC) include the followings.

-continued
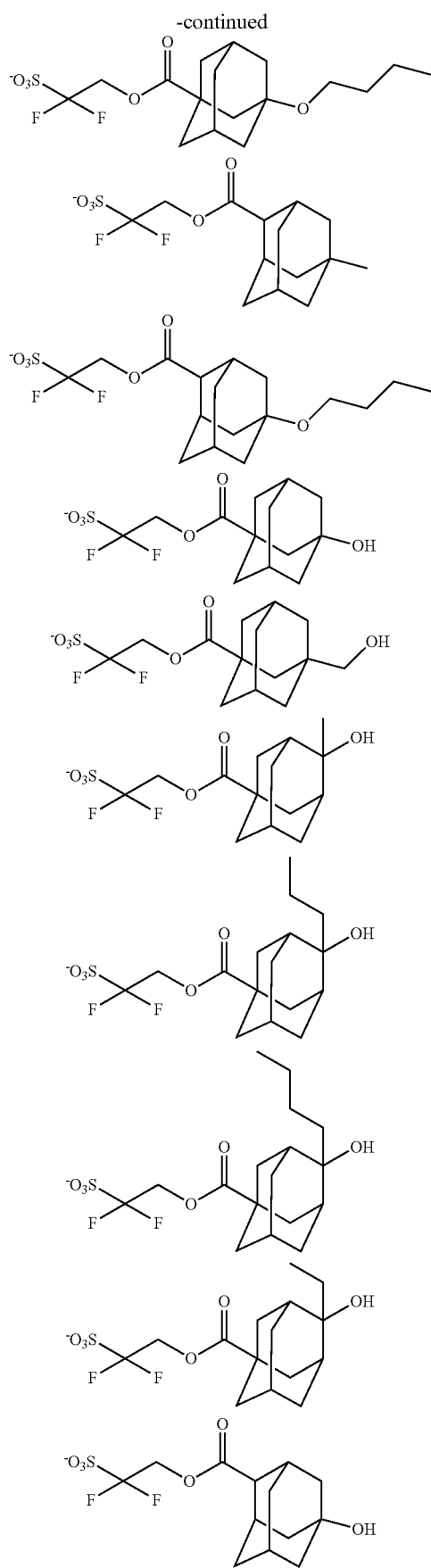
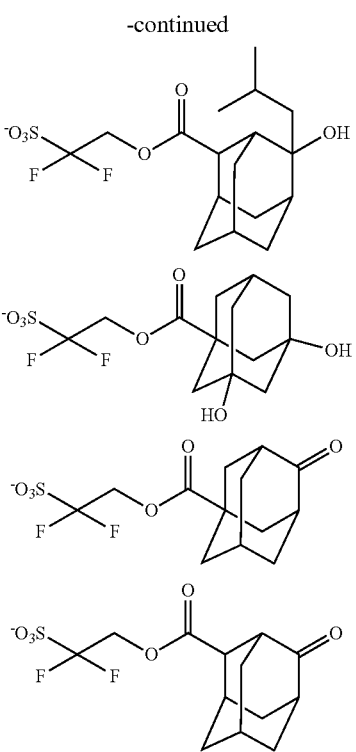
Examples of the anion part represented by the formula (ID) include the followings.
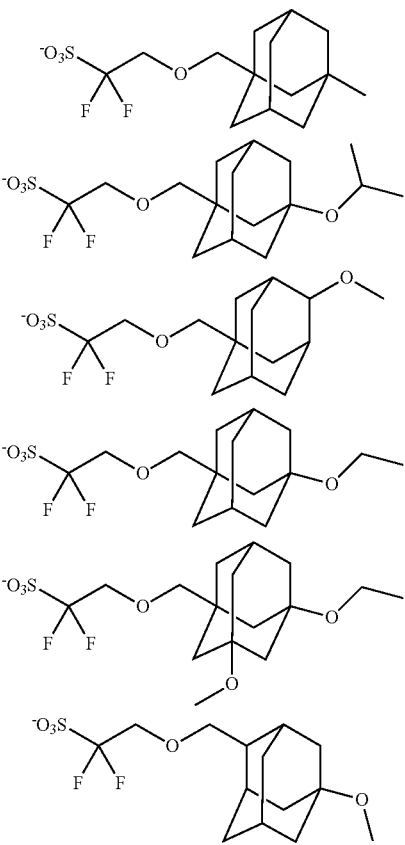

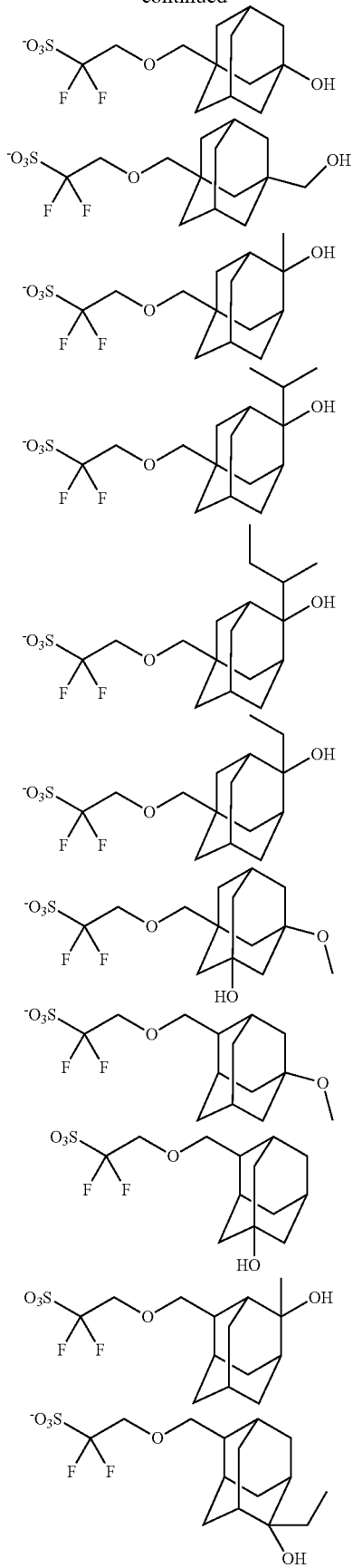

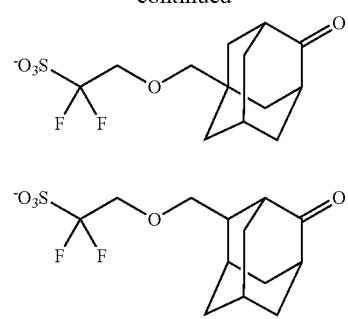

Examples of the cation part represented by Z⁺ of the salt represented by the formula (I) include cations represented by the above-mentioned formulae (IXa), (IXb), (IXc) and (IXd), and a cation represented by the formula (IXa) is preferable.

Among them, a cation is more preferably a triarylsulfonium cation. Examples of the salt represented by the formula (I) include a salt wherein the anion part is any one of the above-mentioned anion part and the cation part is any one of the above-mentioned cation part.

Specific examples of the salt represented by the formula (I) include salts represented by the formulae (Xa) to (Xi):

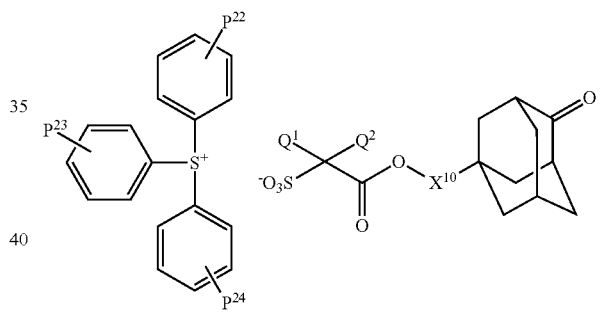

(Xa)

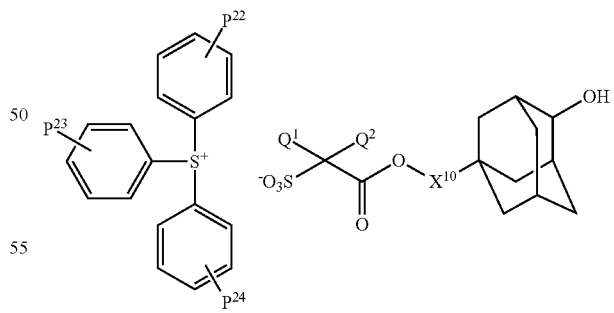

(Xb)

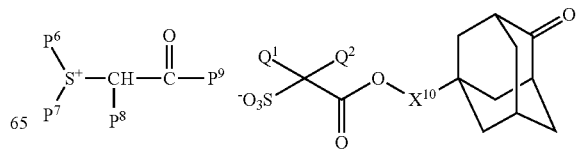

(Xc)

-continued
(Xd)
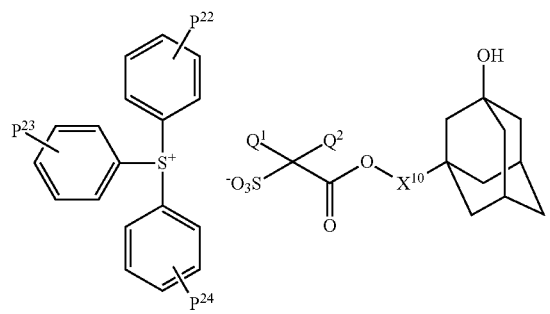
(Xe)
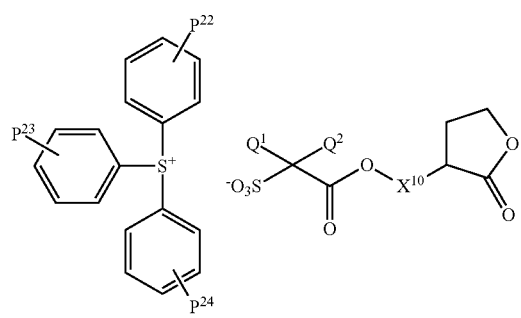
(Xf)
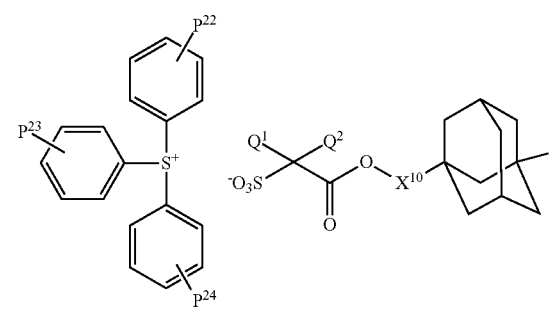
(Xg)
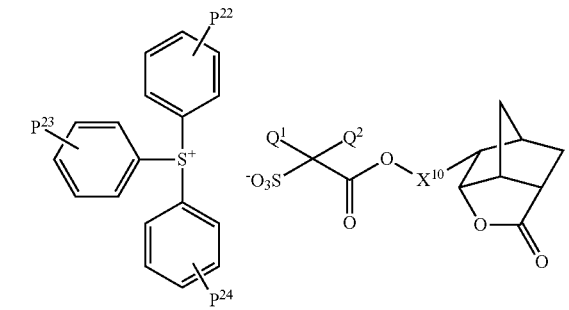
(Xh)
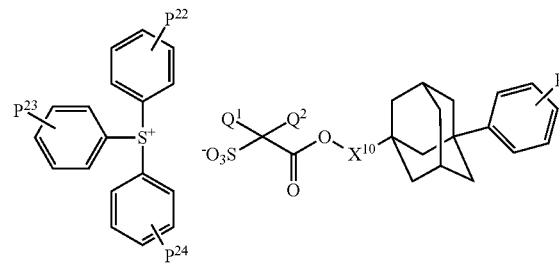
-continued
(Xi)
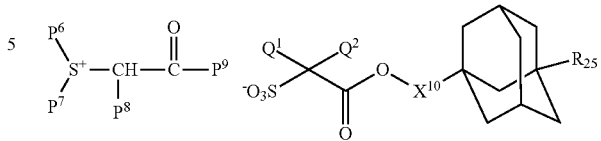
wherein $P^{25}$ independently each represent a hydrogen atom, a C1-C4 aliphatic hydrocarbon group or a C4-C36 alicyclic hydrocarbon group, and $P^{22}$, $P^{23}$, $P^{24}$, $P^6$, $P^7$, $P^8$, $P^9$, $Q^1$, $Q^2$ and $X^{10}$ are the same as defined above.
Preferable examples of the salt represented by the formula (I) include the followings.
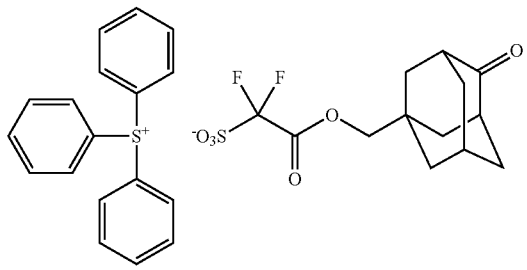

89
-continued
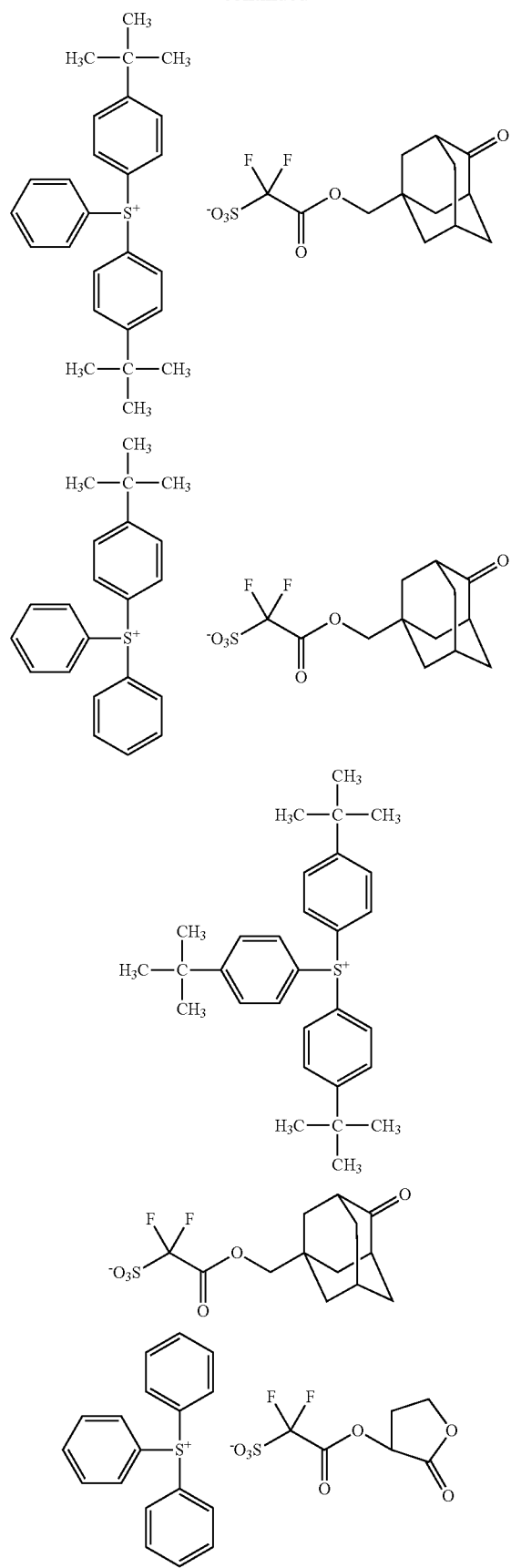
90
-continued
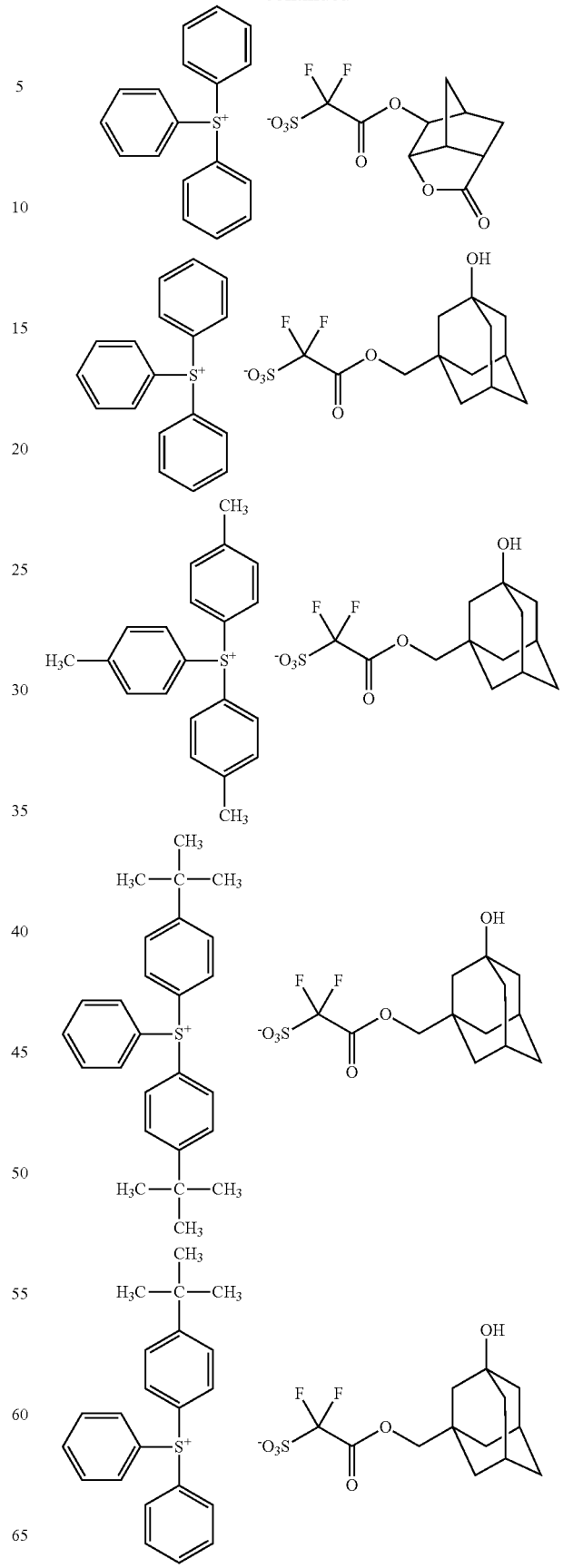

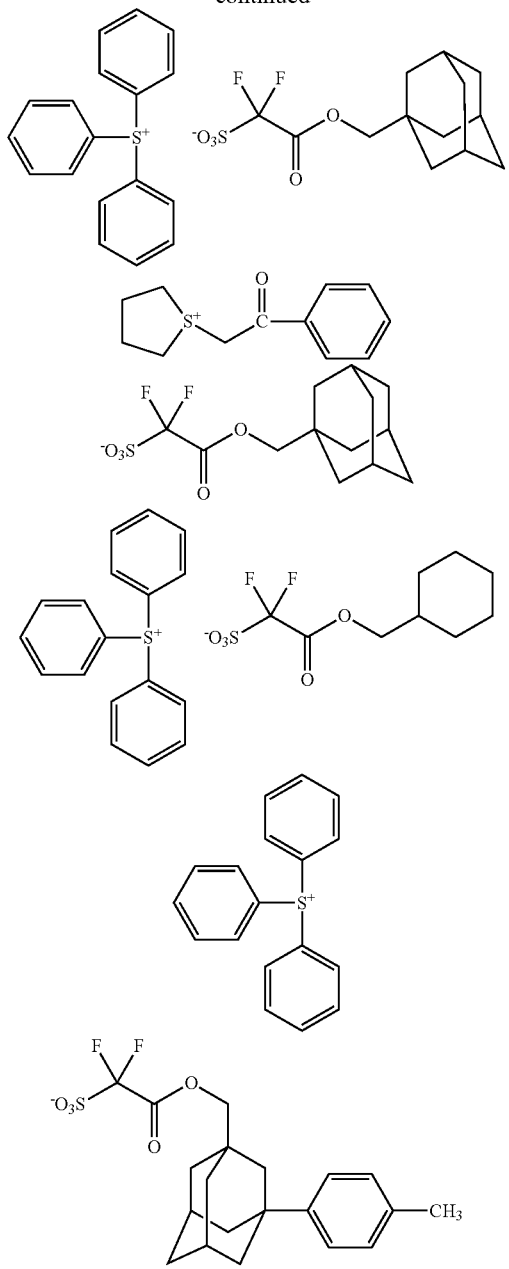

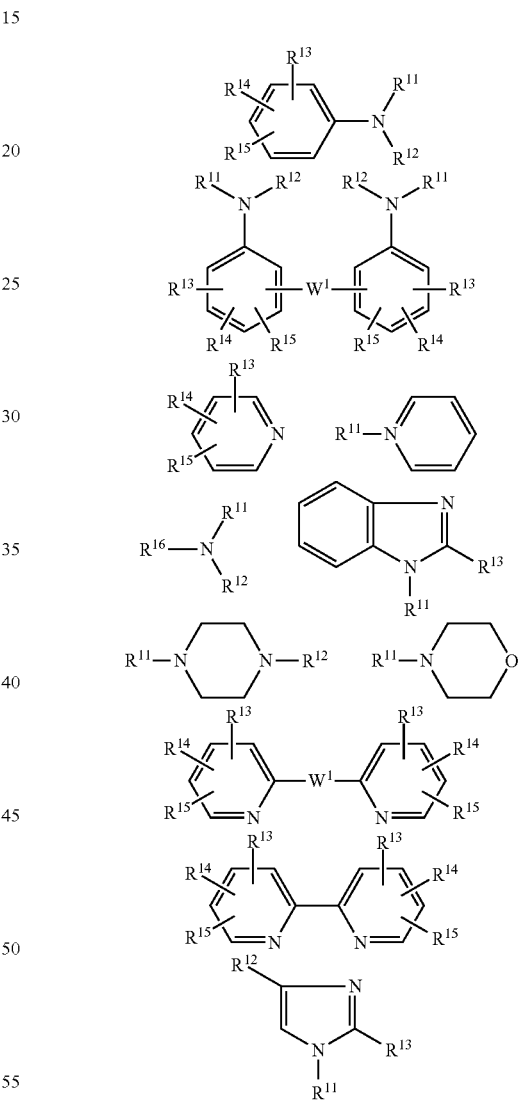

Among them, the salt represented by the formula (I) wherein the cation part is the cation part represented by the above-mentioned formula (IXaaa) in which $P^{22}$, $P^{23}$ and $P^{24}$ are hydrogen atoms and the anion part is the anion part selected from the group consisting of the specific examples of the anion part represented by the formula (IA) cited above is preferable.

Two or more salt represented by the formula (I) can be used in combination.

The salt represented by the formula (I) can be produced, for example, by the method described in JP 2008-56668 A.

The content of the acid generator is usually 0.1 to 20 parts by weight, preferably 1 to 20 parts by weight and more preferably 1 to 15 parts by weight per 100 parts by weight of the resin component.

The photoresist composition can contain two or more kinds of the salt represented by the formula (I-Pa), and can contain two or more kinds of the structural units derived from the salt represented by the formula (I-Pa). The photoresist composition can contain two or more kinds of the resins having no structural units derived from the salt represented by the formula (I-Pa).

In the photoresist composition of the present invention, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

wherein $R^{11}$ and $R^{12}$ independently represent a hydrogen atom, a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, a C1-C6 alkyl group, a C5-C10 cycloalkyl group, a C6-C10 aryl group or a C1-C6 alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, a C1-C6 alkyl group, a C5-C10 cycloalkyl group, a C6-C10 aryl group, a C1-C6 alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents a C1-C6 alkyl group or a C5-C10 cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, a C2-C6 alkylene group, and a quaternary ammonium hydroxide represented by the following formula:

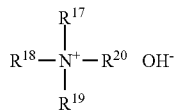

wherein $R^{17}$, $R^{18}$, $R^{19}$ and $R^{20}$ independently represent a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

Examples of the amino group which may be substituted with the C1-C4 alkyl group include an amino group, a methylamino group, an ethylamino group, a butylamino group, a dimethylamino group and a diethylamino group. Examples of the C1-C6 alkoxy group which may be substituted with the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the C1-C6 alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, a propyl group, an isopropyl group, a butyl group, a tert-butyl group, a pentyl group, a hexyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the C5-C10 cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

Specific examples of the C6-C10 aryl group which may be substituted with at least one group selected from the group consisting of a hydroxyl group, an amino group which may be substituted with a C1-C4 alkyl group or a C1-C6 alkoxy group include a phenyl group and a naphthyl group.

Specific examples of the C1-C6 alkoxy group include a methoxy group, an ethoxy group, a propoxy group, an isopropoxy group, a butoxy group, a tert-butoxy group, a pentyloxy group and a hexyloxy group.

Specific examples of the C2-C6 alkylene group include an ethylene group, a trimethylene group and a tetramethylene group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A photoresist pattern can be produced by the following steps (1) to (5):
(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater.

The formation of the photoresist film is usually conducted using a heating apparatus such as hot plate or a decompressor, and the heating temperature is usually 50 to 200° C., and the operation pressure is usually 1 to $1.0*10^5$ pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The salt of the present invention and the polymer of the present invention are suitable components of a photoresist composition, and the photoresist composition of the present invention provides a photoresist pattern showing good resolution and good focus margin, and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can be used for an immersion lithography and for a dry lithography. Furthermore, the photoresist composition of the present invention can be also used for a double imaging lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using standard polystyrene as a standard reference material. Structures of compounds were determined by NMR (GX-270 Type or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Reference Salt Synthesis Example 1

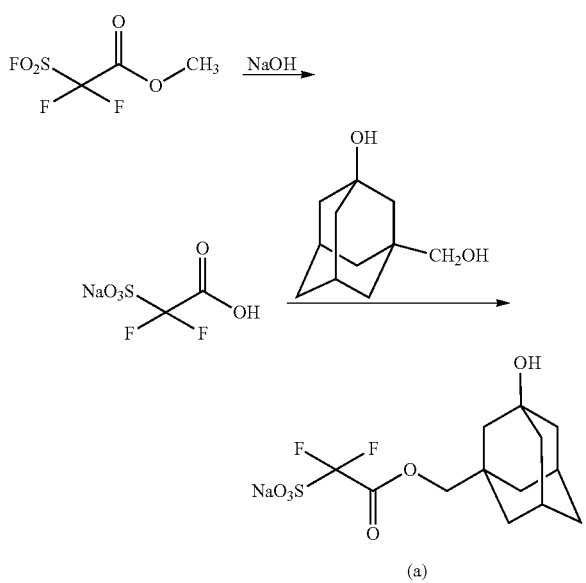

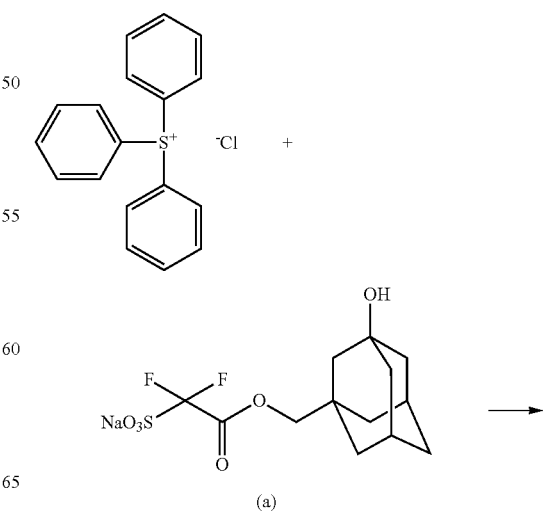

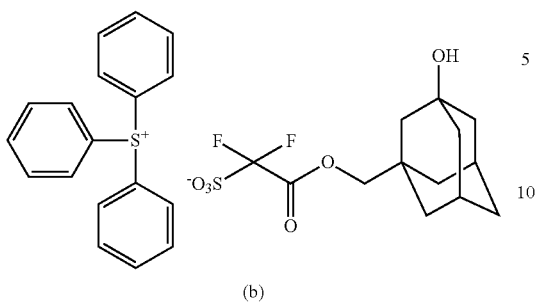

(b)

Into a mixture of 100 parts of methyl difluoro(fluorosulfonyl)acetate and 150 parts of ion-exchanged water, 230 parts of 30% aqueous sodium hydroxide solution was added dropwise in an ice bath. The resultant mixture was heated and refluxed at 100° C. for 3 hours. After cooling down to room temperature, the cooled mixture was neutralized with 88 parts of concentrated hydrochloric acid and the solution obtained was concentrated to obtain 164.4 parts of sodium salt of difluorosulfoacetic acid (containing inorganic salt, purity: 62.7%).

To a mixture of 1.9 parts of sodium salt of difluorosulfoacetic acid (purity: 62.7%) and 9.5 parts of N,N-dimethylformamide, 1.0 part of 1,1'-carbonyldiimidazole was added and the resultant solution was stirred for 2 hours. The solution was added to a solution prepared by mixing 1.1 parts of 3-hydroxyadamantanemethanol, 5.5 parts of N,N-dimethylformamide and 0.2 part of sodium hydride and stirring for 2 hours. The resultant solution was stirred for 15 hours to obtain a solution containing the salt represented by the above-mentioned formula (a).

To the solution containing the salt represented by the above-mentioned formula (a), 17.2 parts of chloroform and 2.9 parts of 14.8% aqueous triphenylsulfonium chloride solution were added. The resultant mixture was stirred for 15 hours, and then separated to an organic layer and an aqueous layer. The aqueous layer was extracted with 6.5 parts of chloroform to obtain a chloroform layer. The organic layer and the chloroform layer were mixed to wash with ion-exchanged water followed by concentration. The concentrate obtained was mixed with 5.0 parts of tert-butyl methyl ether and the mixture obtained was stirred and filtrated to obtain 0.2 part of the salt represented by the above-mentioned formula (b) in the form of a white solid, which is called as A1.

Example 1

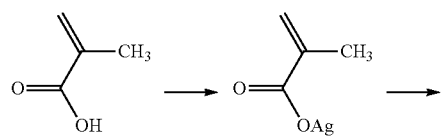

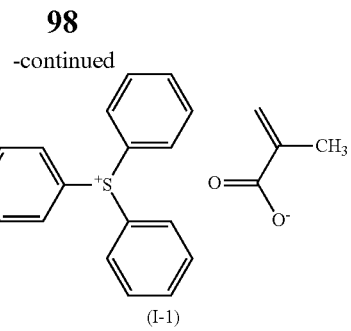

(I-1)

A mixture of 1.72 parts of methacrylic acid and 10.00 parts of acetonitrile was stirred at 23° C. for 30 minutes. To the resultant mixture, 2.32 parts of silver oxide was added. The obtained mixture was stirred at 23° C. for 4 hours, and then, filtrated. The obtained solid was mixed with 10 parts of tert-butyl methyl ether and the resultant mixture was stirred at 23° C. for 30 minutes. The mixture was filtrated and the obtained solid was dried to obtain 2.98 parts of silver methacrylate.

A mixture of 3.90 parts of triphenylsulfonium iodide and 20 parts of methanol was stirred at 23° C. for 30 minutes. To the mixture, slurry prepared by mixing 1.93 parts of silver methacrylate with 10 parts of ion-exchanged water was added dropwise over 1 hour. The resultant mixture was stirred at 23° C. for 5 hours and filtrated. The obtained filtrate was concentrated. The obtained residue was mixed with 15 parts of methanol and then, the obtained mixture was concentrated. The obtained residue was mixed with 10 parts of ethyl acetate. The resultant mixture was stirred and then, supernatant solution was removed. The obtained residue was mixed with 10 parts of tert-butyl methyl ether and supernatant solution was removed. The obtained residue was dissolved in chloroform and the obtained solution was concentrated to obtain 0.54 part of a salt represented by the above-mentioned formula (I-1) in the form of orange oil. This is called as salt (I-1).

MS (ESI(+) Spectrum): M$^+$ 263.1
MS (ESI(−) Spectrum): M$^-$ 85.0
$^1$H-NMR (dimethylsulfoxide-d$_6$, Internal Standard: tetramethylsilane): δ (ppm) 1.68 (s, 3H), 4.79 (m, 1H), 5.38 (m, 1H), 7.70-7.90 (m, 15H)

Example 2

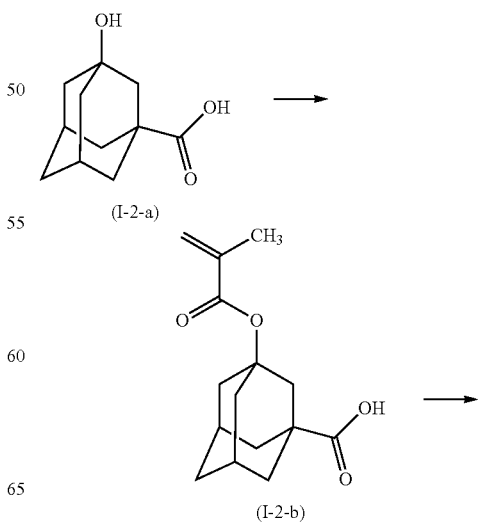

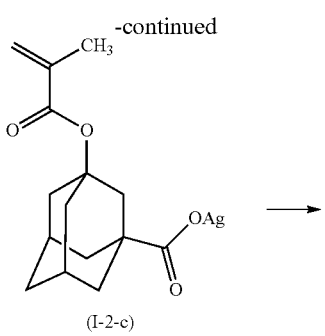

(I-2-c)

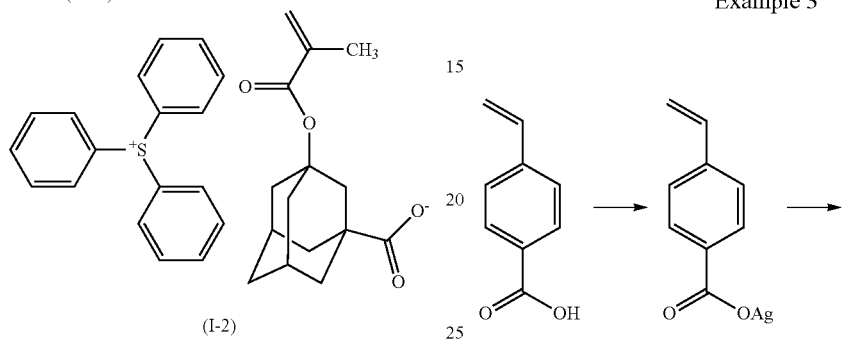

(I-2)

To the mixture of 1.96 parts of the compound represented by the formula (I-2-a), 1.28 parts of N-methylpyrrolidine and 15.0 parts of N,N-dimethylformamide, 3, 12 parts of methacryloyl chloride was added with stirring, and the resultant mixture was stirred at 30° C. for 2 hours. To the obtained mixture, 20 parts of chloroform and 20 parts of ion-exchanged water were added, and the resultant mixture was separated to an organic layer and an aqueous layer. The organic layer was washed with 20.0 parts of saturated aqueous sodium bicarbonate solution, with 20.0 parts of saturated aqueous ammonium chloride solution and with 20.0 parts of ion-exchanged water. The organic layer was concentrated to obtain 2.22 parts of the compound represented by the formula (I-2-b).

A mixture of 2.11 parts of the compound represented by the formula (I-2-b) and 20.00 parts of acetonitrile was stirred at 23° C. for 30 minutes. To the resultant mixture, 0.93 part of silver oxide was added. The obtained mixture was stirred at 23° C. for 4 hours, and then, filtrated. The obtained solid was mixed with 10 parts of tert-butyl methyl ether and the resultant mixture was stirred at 23° C. for 30 minutes. The mixture was filtrated and the obtained solid was dried to obtain 2.49 parts of the compound represented by the formula (I-2-c).

A mixture of 1.95 parts of triphenylsulfonium iodide and 10 parts of methanol was stirred at 23° C. for 30 minutes. To the mixture, slurry prepared by mixing 1.86 parts of the compound represented by the formula (I-2-c) with 10 parts of ion-exchanged water was added dropwise over 1 hour. The resultant mixture was stirred at 23° C. for 5 hours and filtrated. The obtained filtrate was concentrated. The obtained residue was mixed with 15 parts of methanol and then, the obtained mixture was concentrated. The obtained residue was mixed with 10 parts of ethyl acetate. The resultant mixture was stirred and then, supernatant solution was removed. The obtained residue was mixed with 10 parts of tert-butyl methyl ether and supernatant solution was removed. The obtained residue was dissolved in chloroform and the obtained solution was concentrated to obtain 1.48 part of a salt represented by the above-mentioned formula (I-2) in the form of orange oil. This is called as salt (I-2).

MS (ESI(+) Spectrum): $M^+$ 263.1

MS (ESI(−) Spectrum): $M^-$ 263.1

$^1$H-NMR (dimethylsulfoxide-$d_6$, Internal Standard: tetramethylsilane): δ (ppm) 1.55-2.42 (m, 17H), 5.50 (m, 1H), 6.02 (m, 1H), 7.70-7.90 (m, 15H)

Example 3

(I-3)

A mixture of 3.08 parts of 4-vinylbenzoic acid and 15.00 parts of acetonitrile was stirred at 23° C. for 30 minutes. To the resultant mixture, 2.32 parts of silver oxide was added. The obtained mixture was stirred at 23° C. for 4 hours, and then, filtrated. The obtained solid was mixed with 10 parts of tert-butyl methyl ether and the resultant mixture was stirred at 23° C. for 30 minutes. The mixture was filtrated and the obtained solid was dried to obtain 4.34 parts of silver 4-vinylbenzoate.

A mixture of 3.90 parts of triphenylsulfonium iodide and 20 parts of methanol was stirred at 23° C. for 30 minutes. To the mixture, slurry prepared by mixing 2.55 parts of silver 4-vinylbenzoate with 12 parts of ion-exchanged water was added dropwise over 1 hour. The resultant mixture was stirred at 23° C. for 5 hours and filtrated. The obtained filtrate was concentrated. The obtained residue was mixed with 18 parts of methanol and then, the obtained mixture was concentrated. The obtained residue was mixed with 15 parts of ethyl acetate. The resultant mixture was stirred and then, supernatant solution was removed. The obtained residue was mixed with 15 parts of tert-butyl methyl ether and supernatant solution was removed. The obtained residue was dissolved in chloroform and the obtained solution was concentrated to obtain 0.87 part of a salt represented by the above-mentioned formula (I-3). This is called as salt (I-3).

MS (ESI(+) Spectrum): $M^+$ 263.1

MS (ESI(−) Spectrum): $M^-$ 147.1

Example 4

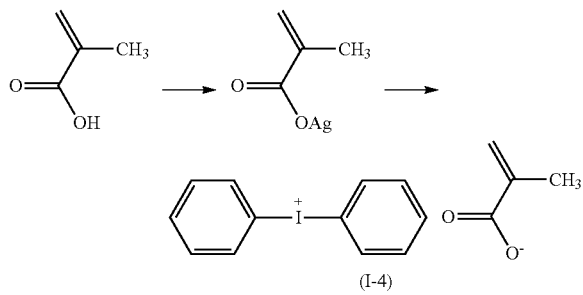

(I-4)

A mixture of 1.72 parts of methacrylic acid and 10.00 parts of acetonitrile was stirred at 23° C. for 30 minutes. To the resultant mixture, 2.32 parts of silver oxide was added. The obtained mixture was stirred at 23° C. for 4 hours, and then, filtrated. The obtained solid was mixed with 10 parts of tert-butyl methyl ether and the resultant mixture was stirred at 23° C. for 30 minutes. The mixture was filtrated and the obtained solid was dried to obtain 2.98 parts of silver methacrylate.

A mixture of 3.16 parts of diphenyliodonium chloride and 16 parts of methanol was stirred at 23° C. for 30 minutes. To the mixture, slurry prepared by mixing 1.93 parts of silver methacrylate with 10 parts of ion-exchanged water was added dropwise over 1 hour. The resultant mixture was stirred at 23° C. for 5 hours and filtrated. The obtained filtrate was concentrated. The obtained residue was mixed with 15 parts of methanol and then, the obtained mixture was concentrated. The obtained residue was mixed with 10 parts of ethyl acetate. The resultant mixture was stirred and then, supernatant solution was removed. The obtained residue was mixed with 10 parts of tert-butyl methyl ether and supernatant solution was removed. The obtained residue was dissolved in chloroform and the obtained solution was concentrated to obtain 0.38 part of a salt represented by the above-mentioned formula (I-4). This is called as salt (I-4).

MS (ESI(+) Spectrum): $M^+$ 281.0
MS (ESI(−) Spectrum): $M^-$ 85.0

Example 5

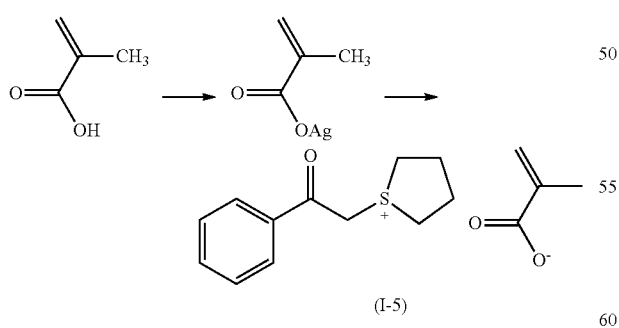

(I-5)

A mixture of 1.72 parts of methacrylic acid and 10.00 parts of acetonitrile was stirred at 23° C. for 30 minutes. To the resultant mixture, 2.32 parts of silver oxide was added. The obtained mixture was stirred at 23° C. for 4 hours, and then, filtrated. The obtained solid was mixed with 10 parts of tert-butyl methyl ether and the resultant mixture was stirred at 23° C. for 30 minutes. The mixture was filtrated and the obtained solid was dried to obtain 2.98 parts of silver methacrylate.

A mixture of 2.87 parts of 1-(2-oxo-2-phenylethyl)tetrahydrothiophenium bromide and 15 parts of methanol was stirred at 23° C. for 30 minutes. To the mixture, slurry prepared by mixing 1.93 parts of silver methacrylate with 10 parts of ion-exchanged water was added dropwise over 1 hour. The resultant mixture was stirred at 23° C. for 5 hours and filtrated. The obtained filtrate was concentrated. The obtained residue was mixed with 10 parts of methanol and then, the obtained mixture was concentrated. The obtained residue was mixed with 10 parts of ethyl acetate. The resultant mixture was stirred and then, supernatant solution was removed. The obtained residue was mixed with 10 parts of tert-butyl methyl ether and supernatant solution was removed. The obtained residue was dissolved in chloroform and the obtained solution was concentrated to obtain 0.25 part of a salt represented by the above-mentioned formula (I-5). This is called as salt (I-5).

MS (ESI(+) Spectrum): $M^+$ 207.1
MS (ESI(−) Spectrum): $M^-$ 85.0

Monomers used in the following Examples are following monomers A, B, C, D, E and F.

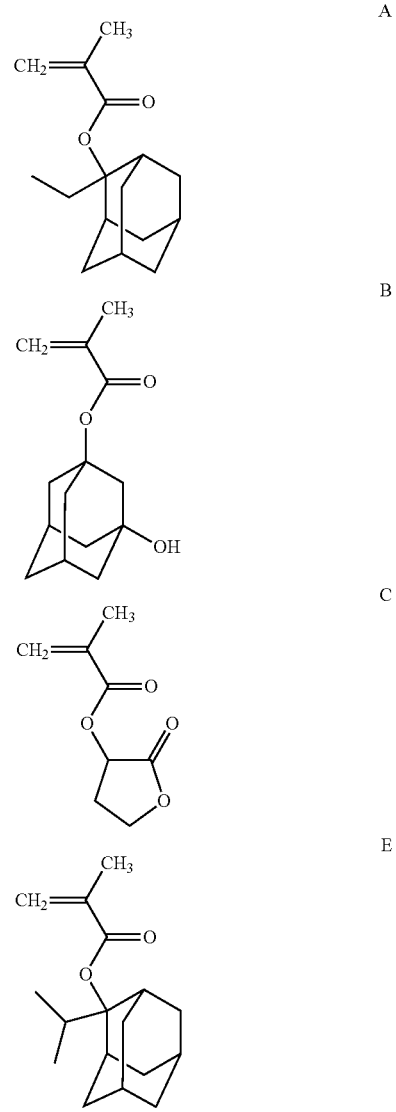

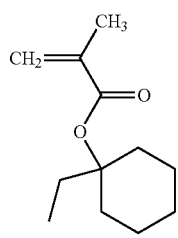

F

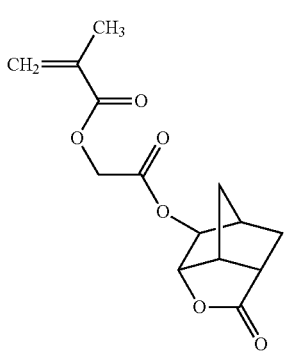

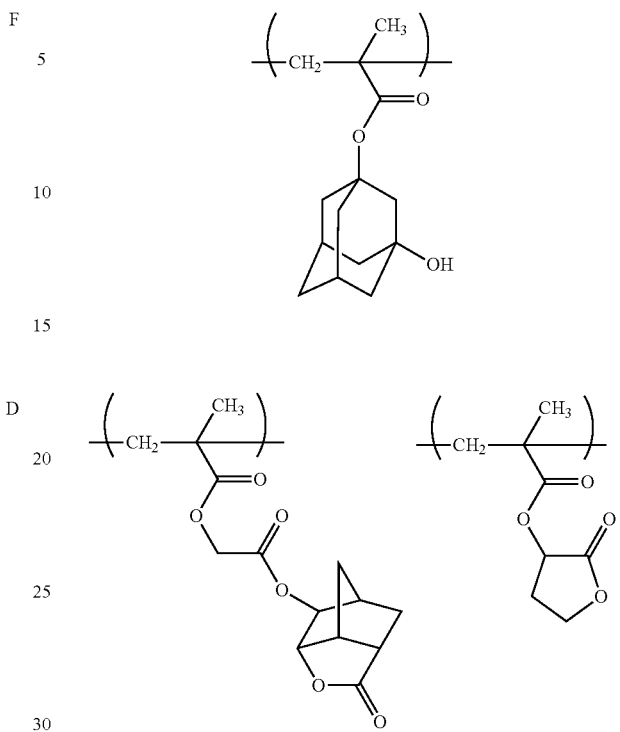

Resin Synthesis Example 1

The monomers E, F, B, D and C were mixed in a molar ratio of 28/14/6/21/31 (monomer E/monomer F/monomer B/monomer D/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a resin having a weight-average molecular weight of 8,452 was obtained in a yield of 74%. The resin had the following structural units. This is called as resin C1.

Resin Synthesis Example 2

The monomers A, B and C were mixed in a molar ratio of 50/25/25 (monomer A/monomer B/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water to cause precipitation, and this operation was repeated three times for purification. As a result, a resin having a weight-average molecular weight of about 8,000 was obtained in a yield of 60%. The resin had the following structural units. This is called as resin C2.

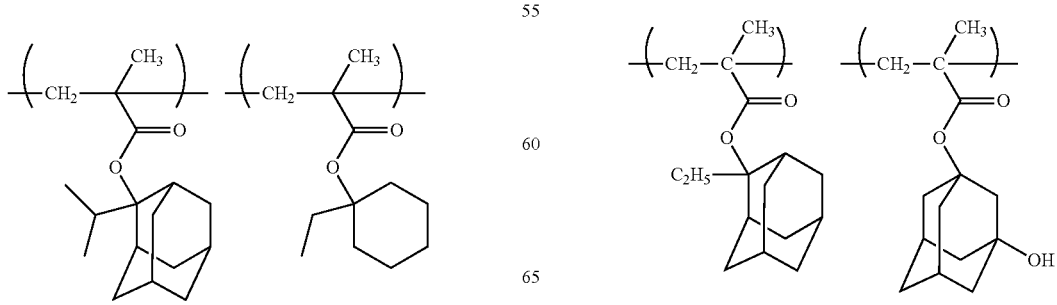

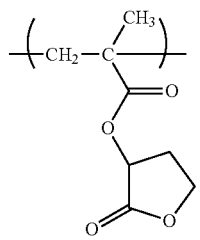

Example 6

Salt (I-1) and 1,4-dioxane in 1.5 times part based on parts of salt (I-1) were mixed to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 4,800 was obtained in a yield of 29%. The polymer had the following structural units. This is called as polymer BB1.

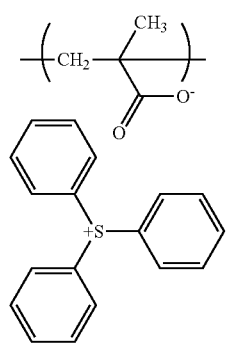

Example 7

Salt (I-2) and 1,4-dioxane in 1.5 times part based on parts of salt (I-2) were mixed to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 6,700 was obtained in a yield of 60%. The polymer had the following structural units. This is called as resin BB2.

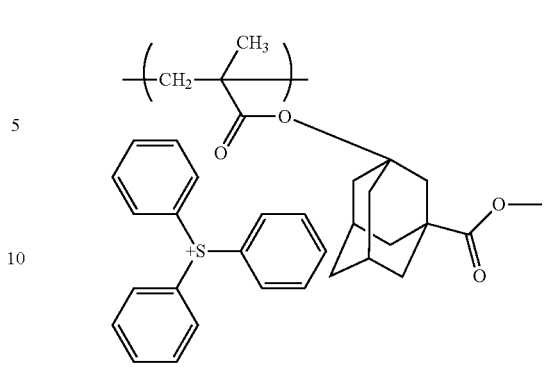

Example 8

The monomers A, B and C and salt (I-1) were mixed in a molar ratio of 40/25/25/10 (monomer A/monomer B/monomer C/salt (I-1)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2, 4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 6,000 was obtained in a yield of 42%. The polymer had the following structural units. This is called as polymer BA1.

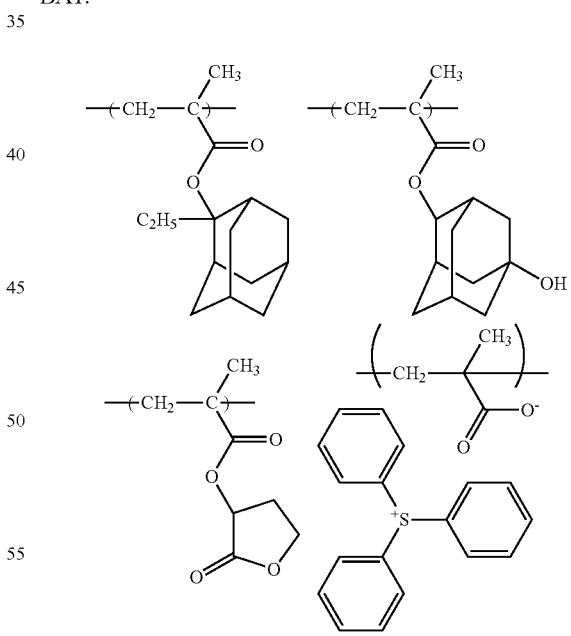

Examples 9

The monomers A, B and C and salt (I-2) were mixed in a molar ratio of 40/25/25/10 (monomer A/monomer B/monomer C/salt (I-2)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 7,000 was obtained in a yield of 62%. The polymer had the following structural units. This is called as polymer BA2.

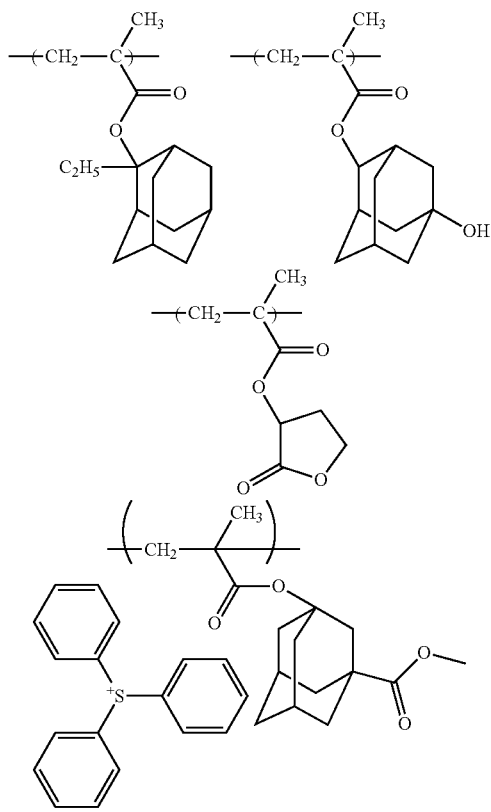

Resin Synthesis Example 3

The monomer A and p-acetoxystyrene were mixed in a molar ratio of 20/80 (monomer A/p-acetoxystyrene), and 1,4-dioxane in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with methanol in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 8,600 was obtained in a yield of 68%. The polymer had the following structural units. This is called as resin C3.

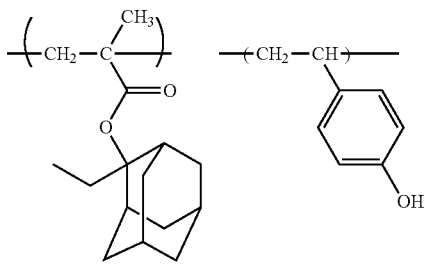

Resin Synthesis Example 4

The monomer A and p-acetoxystyrene were mixed in a molar ratio of 30/70 (monomer A/p-acetoxystyrene), and 1,4-dioxane in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with methanol in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 8,200 was obtained in a yield of 65%. The polymer had the following structural units. This is called as resin C4.

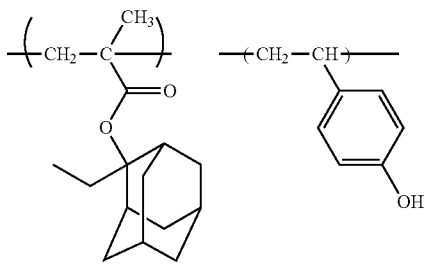

Example 10

The monomer A, p-acetoxystyrene and salt (I-2) were mixed in a molar ratio of 20/70/10 (monomer A/p-acetoxystyrene/salt (I-2)), and 1,4-dioxane in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with acetonitrile in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 7,700 was obtained in a yield of 48%. The polymer had the following structural units. This is called as polymer BA3.

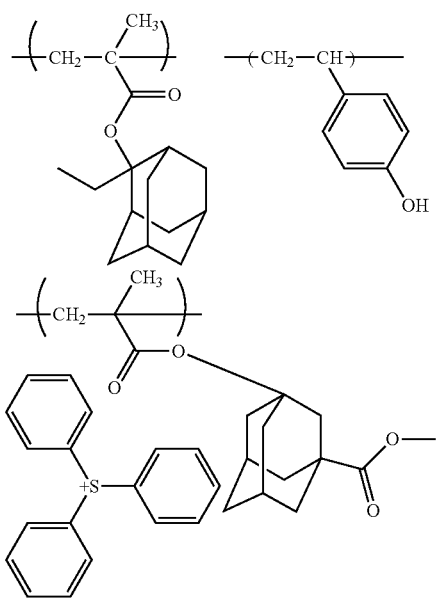

Example 11

The monomer A, p-acetoxystyrene and salt (I-2) were mixed in a molar ratio of 30/60/10 (monomer A/p-acetoxystyrene/salt (I-2)), and 1,4-dioxane in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with acetonitrile in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 7,200 was obtained in a yield of 45%. The polymer had the following structural units. This is called as polymer BA4.

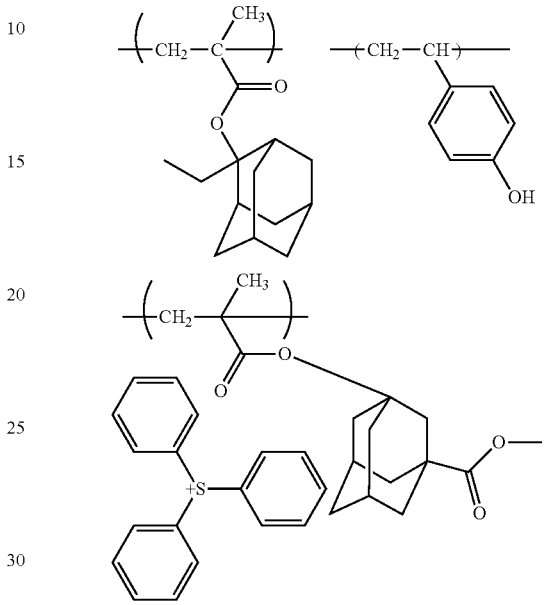

Example 12

The monomers A, B and C and salt (I-4) were mixed in a molar ratio of 40/25/25/10 (monomer A/monomer B/monomer C/salt (I-4)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 6,400 was obtained in a yield of 40%. The polymer had the following structural units. This is called as polymer BA5.

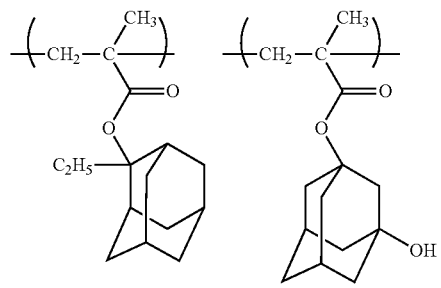

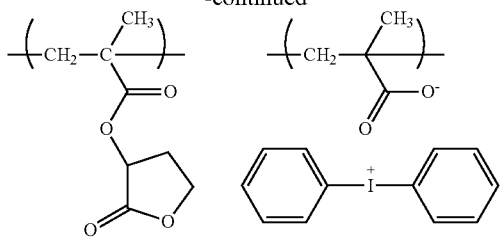

Example 13

The monomers A, B and C and salt (I-5) were mixed in a molar ratio of 40/25/25/10 (monomer A/monomer B/monomer C/salt (I-5)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a polymer having a weight-average molecular weight of about 6,900 was obtained in a yield of 48%. The polymer had the following structural units. This is called as polymer BA6.

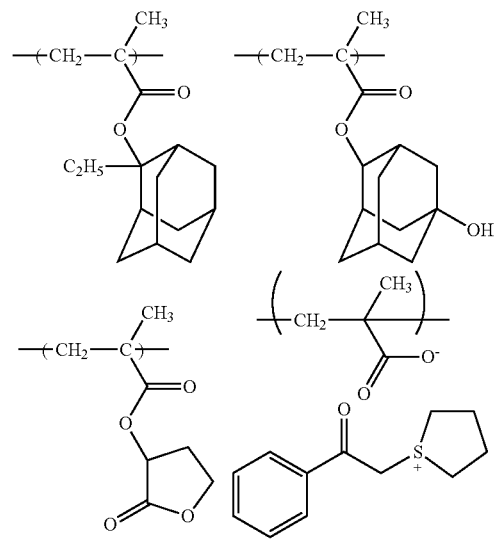

Example 14

The monomer A, p-acetoxystyrene and salt (I-3) were mixed in a molar ratio of 20/70/10 (monomer A/p-acetoxystyrene/salt (I-3)), and acetonitorile in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with acetonitrile in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 8,000 was obtained in a yield of 50%. The polymer had the following structural units. This is called as polymer BA7.

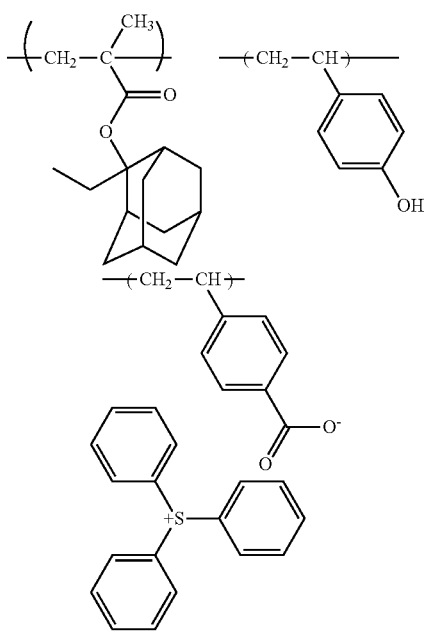

Example 15

The monomer A, p-acetoxystyrene and salt (I-3) were mixed in a molar ratio of 30/60/10 (monomer A/p-acetoxystyrene/salt (I-3)), and acetonitrile in 1.5 times part based on total parts of all monomers was added to prepare a mixture. To the mixture, dimethyl 2,2-azobis(2-methylpropionate) as an initiator in a ratio of 6 mol % based on all monomer molar amount was added, and the obtained mixture was heated at 75° C. for about 12 hours. The reaction mixture obtained was poured into a large amount of methanol to cause precipitation to obtain a copolymer. The obtained copolymer was mixed with acetonitrile in 3 times part based on part of copolymer and then, to the resultant mixture, 4-dimethylaminopyridine in 10 mol % based on all monomer used for polymerization molar amount was added. The obtained mixture was refluxed for 20 hours and then, cooled. The obtained reaction mixture was neutralized with glacial acetic acid and the resultant mixture was poured into a large amount of water to cause precipitation. The precipitate was isolated by filtration and then, dissolved in acetone. The obtained solution was poured into a large amount of water to cause precipitation. This operation was repeated three times for purification. As a result, a polymer having a weight-average molecular weight of about 7,400 was obtained in a yield of 47%. The polymer had the following structural units. This is called as polymer BA8.

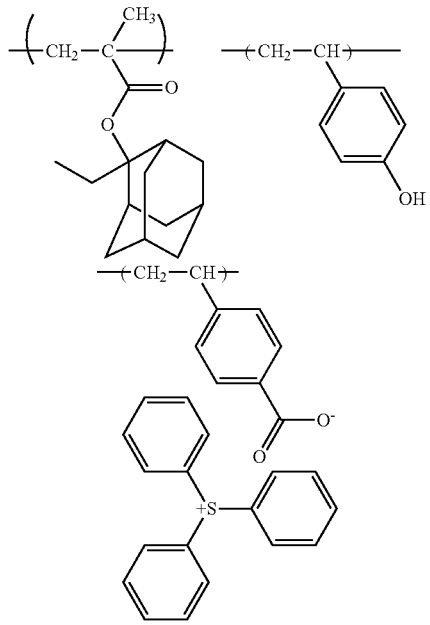

Examples 16 to 28 and Comparative Example 1

Acid Generator

A1.

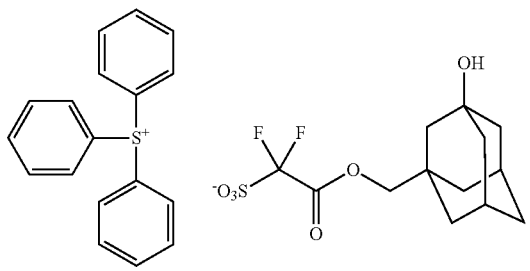

<Resin>
Resin C1, C2
<Salt>
Salt (I-1), (I-2), (I-4), (I-5)
<Polymer>
Polymer BB1, BB2, BA1, BA2, BA5, BA6
<Quencher>
Q1: 2,6-diisopropylaniline
<Solvent>

| Y1: | propylene glycol monomethyl ether acetate | 260 parts |
| | propylene glycol monomethyl ether | 20 parts |
| | γ-butyrolactone | 20 parts |

The following components were mixed and dissolved, further, filtrated through a fluorine resin filter having pore diameter of 0.2 μm, to prepare photoresist compositions.

Salt (kind and amount are described in Table 1)
Polymer (kind and amount are described in Table 1)
Resin (kind and amount are described in Table 1)
Acid generator (kind and amount are described in Table 1)
Quencher (kind and amount are described in Table 1)
Solvent Y1

TABLE 1

| Ex. No. | Salt (kind/ amount (part)) | Polymer (kind/ amount (part)) | Resin (kind/ amount (part)) | Acid Generator (kind/ amount (part)) | Quencher (kind/ amount (part)) |
| --- | --- | --- | --- | --- | --- |
| Ex. 16 | I-1/0.10 | — | C2/10 | A1/0.7 | Q1/0.065 |
| Ex. 17 | I-2/0.10 | — | C2/10 | A1/0.7 | Q1/0.065 |
| Ex. 18 | I-2/0.05 | — | C2/10 | A1/0.7 | Q1/0.065 |
| Ex. 19 | I-2/0.20 | — | C2/10 | A1/0.7 | Q1/0.065 |
| Ex. 20 | — | BB1/1 | C2/9 | A1/0.7 | Q1/0.065 |
| Ex. 21 | — | BB2/1 | C2/9 | A1/0.7 | Q1/0.065 |
| Ex. 22 | I-2/0.10 | — | C1/10 | A1/0.7 | Q1/0.065 |
| Ex. 23 | — | BA1/10 | — | A1/0.7 | Q1/0.065 |
| Ex. 24 | — | BA2/10 | — | A1/0.7 | Q1/0.065 |
| Ex. 25 | I-4/0.05 | — | C2/10 | A1/0.7 | Q1/0.065 |
| Ex. 26 | I-5/0.05 | — | C2/10 | A1/0.7 | Q1/0.065 |
| Ex. 27 | — | BA5/10 | — | A1/0.7 | Q1/0.065 |
| Ex. 28 | — | BA6/10 | — | A1/0.7 | Q1/0.065 |
| Comp. Ex. 1 | — | — | C1/10 | A1/0.7 | Q1/0.065 |

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at 95° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 95° C. for 60 seconds and then to paddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution: The photoresist pattern at the exposure dose that the line pattern and the space pattern become 1:1 after exposure through 100 nm line and space pattern mask and development was observed with a scanning electron microscope. When 85 nm line and space pattern was resolved, the resolution is good and its evaluation is marked by "○", and when 85 nm line and space pattern was not resolved or was resolved but the toppling of the patterns was observed, the resolution is bad and its evaluation is marked by "X".

Focus margin (DOF): The photoresist patterns were obtained using a 90 nm line and space pattern mask at the exposure amount where the line width of the line pattern and the space pattern became 90 nm, with the focal point distance being varied stepwise. Each of patterns developed on the organic anti-reflective coating substrate after the development were observed and the focal point distances when the patterns of which line width was 90 nm±5% (about 85.5 to 94.5 nm) were obtained were measured and the difference between the max value of the focal point distance and the minimum value of the focal point distance was calculated. When the difference is 0.60 μm or more, DOF is good and its evaluation is marked by "○", and when the difference is less than 0.60 μm, DOF is bad and its evaluation is marked by "X".

TABLE 2

| Ex. No. | Resolution | DOF |
| --- | --- | --- |
| Ex. 16 | ○ | ○ |
| Ex. 17 | ○ | ○ |
| Ex. 18 | ○ | ○ |
| Ex. 19 | ○ | ○ |
| Ex. 20 | ○ | ○ |
| Ex. 21 | ○ | ○ |
| Ex. 22 | ○ | ○ |
| Ex. 23 | ○ | ○ |
| Ex. 24 | ○ | ○ |
| Ex. 25 | ○ | ○ |
| Ex. 26 | ○ | ○ |
| Ex. 27 | ○ | ○ |
| Ex. 28 | ○ | ○ |
| Comp. Ex. 1 | X | X |

Examples 29 to 35 and Comparative Example 2

Acid Generator

A1:

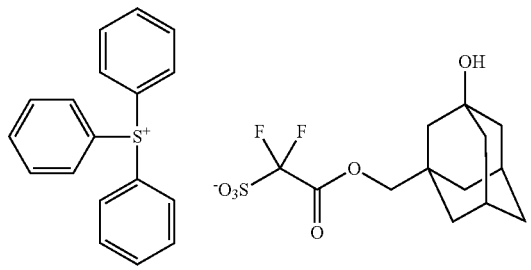

A2: triphenylsulfonium triisopropylbenzenesulfonate
A3: N-(ethylsulfonyloxy)succinimide
<Resin>
Resin C3, C4
<Salt>
Salt (I-1), (I-2), (I-3)
<Polymer>
Polymer BA3, BA4, BA7, BA8
<Quencher>
Q1: 2,6-diisopropylaniline
Q2: tetrabutylammonium hydroxide
<Solvent>

| Y1: | propylene glycol monomethyl ether acetate | 260 parts |
| --- | --- | --- |
| | propylene glycol monomethyl ether | 20 parts |
| | γ-butyrolactone | 20 parts |

The following components were mixed and dissolved, further, filtrated through a fluorine resin filter having pore diameter of 0.2 μm, to prepare photoresist compositions.
Salt (kind and amount are described in Table 3)
Polymer (kind and amount are described in Table 3)
Resin (kind and amount are described in Table 3)
Acid generator (kind and amount are described in Table 3)
Quencher (kind and amount are described in Table 3)
Solvent Y1

TABLE 3

| Ex. No. | Salt (kind/amount (part)) | Polymer (kind/amount (part)) | Resin (kind/amount (part)) | Acid Generator (kind/amount (part)) | Quencher (kind/amount (part)) |
| --- | --- | --- | --- | --- | --- |
| Ex. 29 | I-1/0.10 | — | C3/5 C4/5 | A1/0.7 | Q1/0.04 Q2/0.01 |
| Ex. 30 | I-2/0.10 | — | C3/5 C4/5 | A1/0.7 | Q1/0.04 Q2/0.01 |
| Ex. 31 | — | BA3/5 BA4/5 | — | A1/0.7 | Q1/0.04 Q2/0.01 |
| Ex. 32 | I-1/0.10 | — | C3/5 C4/5 | A2/1.0 A3/1.0 | Q1/0.055 |
| Ex. 33 | — | BA3/5 BA4/5 | — | A2/1.0 A3/1.0 | Q1/0.055 |
| Ex. 34 | I-3/0.10 | — | C3/5 C4/5 | A1/0.7 | Q1/0.04 Q2/0.01 |
| Ex. 35 | — | BA7/5 BA8/5 | — | A2/1.0 A3/1.0 | Q1/0.055 |
| Comp. Ex. 2 | — | — | C3/5 C4/5 | A2/1.0 A3/1.0 | Q1/0.055 |

TABLE 4

| Ex. No. | PB (° C.) | PEB (° C.) |
| --- | --- | --- |
| Ex. 29 | 95 | 95 |
| Ex. 30 | 95 | 95 |
| Ex. 31 | 95 | 95 |
| Ex. 32 | 110 | 110 |
| Ex. 33 | 110 | 110 |
| Ex. 34 | 95 | 95 |
| Ex. 35 | 110 | 110 |
| Comp. Ex. 2 | 110 | 110 |

Silicon wafers were each contacted with hexamethyldisilazane at 90° C. for 60 seconds on a direct hot plate and each of the resist compositions prepared as above was spin-coated over the silicon wafer to give a film thickness after drying of 60 nm. After application of each of the resist compositions, the silicon wafers thus coated with the respective resist compositions were each prebaked on a direct hotplate at the temperature shown in column of "PB" in Table 4 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at the temperature shown in column of "PEB" in Table 4 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 5.

Resolution: The photoresist pattern at the exposure dose that the line pattern and the space pattern become 1:1 after exposure through 100 nm line and space pattern mask and development was observed with a scanning electron microscope. When 80 nm line and space pattern was resolved, the resolution is good and its evaluation is marked by "○", and when 80 nm line and space pattern was not resolved or was resolved but the toppling of the patterns was observed, the resolution is bad and its evaluation is marked by "X".

Focus margin (DOF): The photoresist patterns were obtained using a 90 nm line and space pattern mask at the exposure amount where the line width of the line pattern and the space pattern became 90 nm, with the focal point distance being varied stepwise. Each of patterns developed on the organic anti-reflective coating substrate after the development were observed and the focal point distances when the patterns of which line width was 90 nm±5% (about 85.5 to 94.5 nm) were obtained were measured and the difference between the max value of the focal point distance and the minimum value of the focal point distance was calculated. When the difference is 0.60 μm or more, DOF is good and its evaluation is marked by "○", and when the difference is less than 0.60 μm, DOF is bad and its evaluation is marked by "X".

TABLE 5

| Ex. No. | Resolution | DOF |
| --- | --- | --- |
| Ex. 29 | ○ | ○ |
| Ex. 30 | ○ | ○ |
| Ex. 31 | ○ | ○ |
| Ex. 32 | ○ | ○ |
| Ex. 33 | ○ | ○ |
| Ex. 34 | ○ | ○ |
| Ex. 35 | ○ | ○ |
| Comp. Ex. 2 | X | X |

Examples 36 to 41 and Comparative Example 3

Acid Generator

A1:

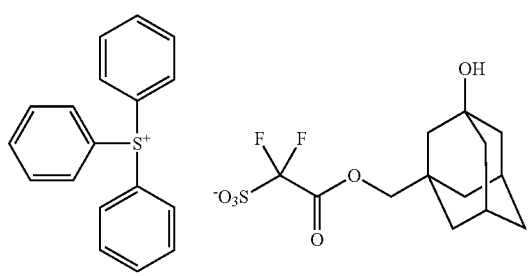

A2: triphenylsulfonium triisopropylbenzenesulfonate
A3: N-(ethylsulfonyloxy)succinimide
<Resin>
Resin C3, C4
<Salt>
Salt (I-1), (I-2), (I-3)
<Polymer>
Polymer BA3, BA4, BA5, BA7, BA8
<Quencher>
Q1: 2,6-diisopropylaniline
Q2: tetrabutylammonium hydroxide <Solvent>

| Y1: | propylene glycol monomethyl ether acetate | 260 parts |
| --- | --- | --- |
| | propylene glycol monomethyl ether | 20 parts |
| | γ-butyrolactone | 20 parts |

The following components were mixed and dissolved, further, filtrated through a fluorine resin filter having pore diameter of 0.2 μm, to prepare photoresist compositions.
Salt (kind and amount are described in Table 6)
Polymer (kind and amount are described in Table 6)
Resin (kind and amount are described in Table 6)
Acid generator (kind and amount are described in Table 6)
Quencher (kind and amount are described in Table 6)
Solvent Y1

TABLE 6

| Ex. No. | Salt (kind/amount (part)) | Polymer (kind/amount (part)) | Resin (kind/amount (part)) | Acid Generator (kind/amount (part)) | Quencher (kind/amount (part)) |
| --- | --- | --- | --- | --- | --- |
| Ex. 36 | I-1/0.10 | — | C3/5 C4/5 | A1/0.7 | Q1/0.04 Q2/0.01 |
| Ex. 37 | I-2/0.10 | — | C3/5 C4/5 | A1/0.7 | Q1/0.04 Q2/0.01 |
| Ex. 38 | — | BA4/5 BA5/5 | — | A1/0.7 | Q1/0.04 Q2/0.01 |
| Ex. 39 | — | BA3/5 BA4/5 | — | A2/1.0 A3/1.0 | Q1/0.055 |
| Ex. 40 | I-3/0.10 | — | C3/5 C4/5 | A1/0.7 | Q1/0.04 Q2/0.01 |
| Ex. 41 | — | BA7/5 BA8/5 | — | A2/1.0 A3/1.0 | Q1/0.055 |
| Comp. Ex. 3 | — | — | C3/5 C4/5 | A2/1.0 A3/1.0 | Q1/0.055 |

TABLE 7

| Ex. No. | PB (° C.) | PEB (° C.) |
| --- | --- | --- |
| Ex. 36 | 95 | 95 |
| Ex. 37 | 95 | 95 |
| Ex. 38 | 95 | 95 |
| Ex. 39 | 110 | 110 |
| Ex. 40 | 95 | 95 |
| Ex. 41 | 110 | 110 |
| Comp. Ex. 3 | 110 | 110 |

Silicon wafers were each contacted with hexamethyldisilazane at 90° C. for 60 seconds on a direct hot plate and each of the resist compositions prepared as above was spin-coated over the silicon wafer to give a film thickness after drying of 50 nm. After application of each of the resist compositions, the silicon wafers thus coated with the respective resist compositions were each prebaked on a direct hotplate at the temperature shown in column of "PB" in Table 7 for 60 seconds. Using an EUV (extreme ultraviolet) exposure system, each wafer on which the respective resist film had been thus formed was exposed to a line and space pattern, while changing stepwise the exposure quantity.

After the exposure, each wafer was subjected to post-exposure baking on a hotplate at the temperature shown in column of "PEB" in Table 7 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 8.

Resolution: The photoresist pattern at the exposure dose that the line pattern and the space pattern become 1:1 after exposure through 50 nm line and space pattern mask and development was observed with a scanning electron microscope. When 45 nm line and space pattern was resolved, the resolution is good and its evaluation is marked by "◯", and when 45 nm line and space pattern was not resolved or was resolved but the toppling of the patterns was observed, the resolution is bad and its evaluation is marked by "X".

Focus margin (DOF): The photoresist patterns were obtained using a 50 nm line and space pattern mask at the exposure amount where the line width of the line pattern and the space pattern became 50 nm, with the focal point distance being varied stepwise. Each of patterns developed on the organic anti-reflective coating substrate after the development were observed and the focal point distances when the patterns of which line width was 50 nm±5% (about 47.5 to 52.5 nm) were obtained were measured and the difference between the max value of the focal point distance and the minimum value of the focal point distance was calculated. When the difference is 0.15 μm or more, DOF is good and its evaluation is marked by "◯", and when the difference is less than 0.15 μm, DOF is bad and its evaluation is marked by "X".

TABLE 8

| Ex. No. | Resolution | DOF |
| --- | --- | --- |
| Ex. 36 | ◯ | ◯ |
| Ex. 37 | ◯ | ◯ |
| Ex. 38 | ◯ | ◯ |
| Ex. 39 | ◯ | ◯ |
| Ex. 40 | ◯ | ◯ |
| Ex. 41 | ◯ | ◯ |
| Comp. Ex. 3 | X | X |

The salt of the present invention is novel and is useful as a component of a photoresist composition, and the photoresist composition containing the salt of the present invention provides a photoresist pattern having good resolution, good LER and good focus margin, and is especially suitable for ArF excimer laser lithography, KrF excimer laser lithography, ArF immersion lithography, EUV (extreme ultraviolet) lithography, EUV immersion lithography and EB (electron beam) lithography.

What is claimed is:

1. A photoresist composition comprising a polymer comprising a structureal unit derived from a salt represented by the formula (I-Pa):

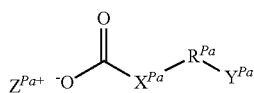

wherein $X^{Pa}$ represents a single bond or a C1-C4 alkylene group, $R^{Pa}$ represents a single bond, a C4-C36 divalent alicyclic hydrocarbon group or a C6-C36 divalent aromatic hydrocarbon group, and one or more methylene groups in the divalent alicyclic hydrocarbon group can be replaced by —O— or —CO—, $Y^{Pa}$ represents a polymerizable group, and $Z^{Pa+}$ represents an organic cation, and a salt represented by the formula (I):

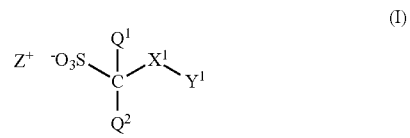

wherein $Q^1$ and $Q^2$ each independently represent a fluorine atom or a C1-C4 perfluoroalkyl group, $X^1$ represents a single bond or a C1-C17 saturated hydrocarbon group which can have one or more substituents, and one or more methylene groups in the saturated hydrocarbon group can be replaced by —O— or —CO—, $Y^1$ represents a C1-C36 aliphatic hydrocarbon group, a C3-C36 alicyclic hydrocarbon group or a C6-C24 aromatic hydrocarbon group, and the aliphatic hydrocarbon group, the alicyclic hydrocarbon group and the aromatic hydrocarbon group can have one or more substituents, and one or more methylene groups in the aliphatic hydrocarbon group and the alicyclic hydrocarbon group can be replaced by —O— or —CO—, $Z^+$ represents an organic cation.

2. A photoresist composition comprising a salt represented by the formula (I-Pa):

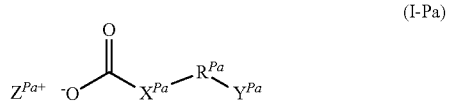

wherein $X^{Pa}$ represents a single bond or a C1-C4 alkylene group, $R^{Pa}$ represents a single bond, a C4-C36 divalent alicyclic hydrocarbon group or a C6-C36 divalent aromatic hydrocarbon group, and one or more methylene groups in the divalent alicyclic hydrocarbon group can be replaced by —O— or —CO—, $Y^{Pa}$ represents a polymerizable group, and $Z^{Pa+}$ represnts an organic cation, an acid generator and a resin comprising a structural unit having an acid-labile group and being insoluble or poorly soluble in art aqueous alkali solution but becoming soluble in an aqueous alkali solution by the action of an acid.

3. The photoresist composition according to claim 1, wherein the photoresist composition further contains a basic compound.

4. A process for producing a photoresist pattern comprising the following steps (1) to (5):

(1) a step of applying the photoresist composition according to claim 1, on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

5. A process for producing a photoresist pattern comprising the following steps (1) to (5):
  (1) a step of applying the photoresist composition according to claim 2, on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby; forming, a photoresist pattern.

6. A process for producing a photoresist pattern comprising the following steps (1) to (5):
  (1) a step of applying the photoresist composition according to claim 3, on a substrate,
  (2) a step of forming a photoresist film by conducting drying,
  (3) a step or exposing the photoresist film to radiation,
  (4) a step of baking the exposed photoresist film, and
  (5) a step of developing the baked photoresist film with an alkaline developer, thereby forming a photoresist pattern.

7. The photoresist composition according to claim 2, wherein the photoresist composition further contains a basic compound.

8. A process for producing a photoresist pattern comprising the following steps (1) to (5):
  (1) a step of applying the photoresist composition according to claim 7, on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby forming a photoresist pattern.

9. The photoresist composition according to claim 1, wherein the polymerizable group is a vinyl group, an acryloyl group, a methacryloyl group, an acryloyloxy group or a methacryloyloxy group, and the vinyl, acryloyl, methacryloyl, acryloyloxy and methacryloyloxy groups can have one or more substituents.

10. The photoresist composition according to claim 1, wherein $Z^{Pa+}$ is a cation represented by the formula (IXa):

(IXa)

wherein $P^B$, $P^C$ and $P^D$ independently each represent a C1-C10 aliphatic hydrocarbon group which can have one or more substituents, a C4-C36 alicyclic hydrocarbon group which can have one or more substituents, a C6-C36 aromatic hydrocarbon group which can have one or more substituents or a C3-C36 heterocyclic group which can have one or more substituents, and any two of $P^B$, $P^C$ and $P^D$ can be bonded to each other to form a ring, and one or more methylene groups in the aliphatic hydrocarbon group and the alicyclic hydrocarbon group can be replaced by —O— or —O—.

11. The photoresist composition according to claim 1, wherein $R^{Pa}$ is single bond or an adamantanediyl group.

* * * * *